US007098000B2

(12) United States Patent
Cheng et al.

(10) Patent No.: US 7,098,000 B2
(45) Date of Patent: Aug. 29, 2006

(54) METHOD FOR PRODUCTION OF C30-ALDEHYDE CAROTENOIDS

(75) Inventors: Qiong Cheng, Wilmington, DE (US); Luan Tao, Claymont, DE (US)

(73) Assignee: E. I. du Pont de Nemoure and Company, Wilmington, DE (US)

( * ) Notice: Subject to any disclaimer, the term of this patent is extended or adjusted under 35 U.S.C. 154(b) by 121 days.

(21) Appl. No.: 10/860,291

(22) Filed: Jun. 3, 2004

(65) Prior Publication Data

US 2004/0268436 A1 Dec. 30, 2004

Related U.S. Application Data

(60) Provisional application No. 60/475,743, filed on Jun. 4, 2003.

(51) Int. Cl.
*A01H 1/00* (2006.01)
*C12N 15/32* (2006.01)
*C12N 1/21* (2006.01)
*C12Q 1/68* (2006.01)
*C07H 21/04* (2006.01)

(52) U.S. Cl. ............................ 435/67; 435/6; 435/69.1; 435/193; 435/252.3; 435/254.2; 435/320.1; 435/419; 435/166; 435/167; 435/183; 435/325; 536/23.2

(58) Field of Classification Search .................. 435/67, 435/6, 69.1, 193, 252.3, 254.2, 320.1, 419; 536/23.2
See application file for complete search history.

(56) References Cited

U.S. PATENT DOCUMENTS

| | | | |
|---|---|---|---|
| 5,182,208 A | 1/1993 | Johnson et al. | |
| 5,429,939 A | 7/1995 | Misawa et al. | |
| 5,466,599 A | 11/1995 | Jacobson et al. | |
| 5,530,188 A | 6/1996 | Ausich et al. | |
| 5,530,189 A | 6/1996 | Ausich et al. | |
| 5,545,816 A | 8/1996 | Ausich et al. | |
| 5,656,472 A | 8/1997 | Ausich et al. | |
| 5,691,190 A | 11/1997 | Girard et al. | |
| 5,972,642 A | 10/1999 | Fleno et al. | |
| 6,015,684 A | 1/2000 | Jacobson et al. | |
| 6,124,113 A | 9/2000 | Hohmann et al. | |
| 2003/0182687 A1* | 9/2003 | Cheng et al. | 800/282 |

OTHER PUBLICATIONS

Umeno et al. Evolution of the C30 Carotenoid synthase crtM for function in a C40 pathway. Journal of Bacteriology, Dec. 2002, p. 6690-6699.*
Alex Raising . 4, 4'diaponeurosporene desaturase: Catalytic properties of an enzyme from the C30 Carotenoid☐☐pathway of *Staphylococcus aureus*. Journal of Bacteriology, Oct. 1999, p. 6184-187.*
Marshall et al, Proposed pathway of Terpenoid Carotenoid biosynthesis in *Staphylococcus aureus*: Evidence from a study of Mutants J. Bacteriol. 147 No. 3: pp. 914-919, 1981).*
Nelis and Leenheer, Microbial sources of carotenoid pigments used in foods and feeds, Appl. Bacteriol. 70: pp. 181-191, 1991.
Armstrong, Eubacteria Show Their True Colors: Genetics of Carotenoid Pigment Biosynthesis from Microbes to Plants, J. Bact. 176: pp. 4795-4802, 1994.
Armstrong, Genetics of Eubacterial Carotenoid Biosynthesis: A Colorful Tale, Annu. Rev. Microbiol. 51: pp. 629-659, 1997.
Farmer et al., Precursor Balancing for Metabolic Engineering of Lycopene Production in Escherichia coli, Biotechnol. Prog. 17: pp. 57-61, 2001.
Wang et al., Directed Evolution of Metabolically Engineered Escherichia coli for Carotenoid Production, Biotechnol. Prog. 16: pp. 922-926, 2000.
Misawa et al., Metabolic engineering for the production of carotenoids in non-carotenogenic bacteria and yeasts, J. Biotchenol. 59: pp. 169-181, 1998.
Shimada et al., Increased Carotenoid Production by the Food Yeast *Candida utilis* through Metabolic Engineering of the Isoprenoid Pathway, Appl. Environ. Microbiol. 64:pp. 2676-2680, 1998.
Albrecht et al., Metabolic Engineering of the terpenoid biosynthetic pathway of Escherichia coli for production of the carotenoids β-carotine and zeaxanthin, Biotechnol. Lett. 21: pp. 791-795, 1999.
Miura et al., Production of the Carotenoids Lycopene, β-Carotene, and Astaxanthin in the Food Yeast Candida utilis, Appl. Environ. Microbiol. 64:pp. 1226-1229.
Z. Naturforsch 34c: New $C_{30}$-Carotinoic Acid Glucosyl Esters from *Pseudomonas rhodos*, pp. 181-185, 1979.
Z. Naturforsch 37c: On the Biosynthesis of $C_{30}$-Carotenoic Acid Glucosyl Esters in *Pseudomonas rhodos*. Analysis of car-Mutants, pp. 758-760, 1982.
Taylor et al., Triterpenoid Carotenoids and Related Lipids, J. Biochem. 139: pp. 751-760, 1974.
Taylor, Bacterial Triterpenoids, Microbiol. Rev. 48: pp. 181-198, 1984.
Takaichi et al., The major carotenoid in all known species of heliobacteria is the $C_{30}$ carotenoid 4,4'-diaponeurosporene, not neurosporene, Arch. Microbiol. 168, pp. 277-281, 1997.
Marshall et al, Proposed Pathway of Triterpenoid Carotenoid Biosynthesis in *Staphylococcus aureus*: Evidence from a Study of Mutants, , J. Bacteriol. 147 No. 3: pp. 900-913, 1981.
Raisig et al.,Functional properties of diapophytoene and related desaturases of $C_{30}$ and $C_{40}$ carotenoid biosynthetic pathway, Biochim. Biophys. Acta 1533: 164-170, 2001.

(Continued)

*Primary Examiner*—Rebecca E. Prouty
*Assistant Examiner*—Kagnew Gebreyesus

(57) ABSTRACT

The present invention provides methods to engineer microorganisms for the production of $C_{30}$-aldehyde carotenoids. Specifically, various combinations of crtM, sqs, crtN and crtN2 genes from *Staphylococcus aureus* and *Methylomonas* sp. 16a can be co-expressed in transformant hosts, leading to the production of diaponeurosporene monoaldehyde, diapocarotene monoaldehyde, and/or diapocarotene dialdehyde. In a preferred embodiment, the genetically engineered pathway is introduced into a strain of *Escherichia coli* that has been engineered for the expression of carotenoids, and the $C_{30}$-carotenoid product is diapocarotene dialdehyde.

10 Claims, 6 Drawing Sheets

OTHER PUBLICATIONS

Xiong et al., Tracking molecular evolution of photosynthesis by characterization of a major photosynthesis gene cluster from *Heliobacillus mobilis*, Proc. Natl. Acad. Sci. USA 95: 14851-14856, 1998.

Takami et al., Genome sequence of *Oceanobacillus iheyensis* isolated from the Iheya Ridge and its unexpected adaptive capabilities to extreme environments, Nucleic Acids Res., 30: pp. 3927, 3935, 2002.

Marshall et al., Proposed Pathway of Triterpenoid Biosynthesis in *Staphylococcus aureus*: Evidence from a Study of Mutants, J. Bacteriol. 147:pp. 914-919, 1981.

Ingram et al., Effect of Selected Aldehydes on the Growth and Fermentation of Ethanologenic *Escherichia coli*, Biotechnol. Bioeng. 65: 24-33, 1999.

Marnett et al., Mtagenicity in *Escherichia coli* of the major DNA adduct derived from the endogenous mutagen malondialdehyde, Proc. Natl. Acad. Sci. USA 94: 8652-8657, 1997.

Mee et al., Formaldehyde is a bacterial mutagen in a range of *Salmonella* and *Escherichia* indicator strains, Mutagenesis 8: pp. 577-581, 1993.

Kawazoe et al., Mutagenic characteristics of formaldehyde on bacterial systems, Mutat. Res. 156: pp. 153-161, 1985.

\* cited by examiner

Upper Isoprenoid Pathway

C$_{40}$ Synthesis

C$_{30}$ Synthesis

Lower Carotenoid Biosynthetic Pathway diaponeurosporene monoaldehyde (or diaponeurosporene-al)

diapocarotene monoaldehyde diapocarotene dialdehyde (or diapocarotene-dial)

A

Methylomonas sp. 16a carotenoid synthesis genes

B

Staphylococcus aureus ATCC 35556 carotenoid synthesis genes

SEQUENCE LISTING

<160> NUMBER OF SEQ ID NOS: 39

<210> SEQ ID NO 1
<211> LENGTH: 1092
<212> TYPE: DNA
<213> ORGANISM: Methylomonas sp.16a

<400> SEQUENCE: 1

```
atgaacggac ctcaaccact cattaccaac ccgcaattgc tttcgcaatt atcagacgcg      60
gaactacagg cagttttact cgaaggagtc tcacggactt tgcgctcac cattccccag       120
ctgccggaga atctgtaccc tgccgttgcc aacgcctatt tgttgtgccg tatcgtcgac      180
acgatcgaag acgaaatctc gctgaacgcg aacaaaaaa acgtttttg cagcgaattc        240
atccaaatcg tcaaaacagg cgaaggtgct caagctttg ccgatgaact cgcgcctta       300
ctttcgacac aaaccattcc cgccgaacac agcctgattc atttgatccc tagggtcatt      360
gcgatcacgc acagcctgga tcgggcgcaa attgaagcct tggcttgttg cgtggaaacg      420
atggcgaacg gcatgccggt ctatcaagcc ctggacctgc gggccggcct gaaaaccatg      480
aaagacatgg atgattactg ttattacgta gccggctgcg tcggagaaat gctggccaag      540
ctgttttgtc actactcgcc gcaaatcgac gcgcatcgcg acgaattact gaagctttcc      600
gtatcattcg gccaaggctt gcaaatgacc aacattctga agacatctg ggatgatgct      660
cagcgtggcg tgtgctggct gccgcaagac attttcaccg aaaccggctt caacctggcg      720
gacttgacgc caaccaccaa cgacgaacgc tttcgcaaag gactggagca cctgatcagc      780
atcgcgcacg gtcatttgca gaacgccttg acctataccc aattactgcc tcgccacgaa      840
acgggcattc gcaacttctg cctgtgggcg ctgggcatgg cggtgttgac actgaaaaag      900
atcaagcaaa acctgagctt caacgaatcc agccaggtca agatcagccg gaatagcgtc      960
aaggccacga ttttggcctg caagctcagc gcgcgcagca acctgttact ttcattactt      1020
ttcaatctga ccagccaggg actaaagaca cctggttggc agtacttacc cgaatcgcac      1080
actggacaat aa                                                          1092
```

<210> SEQ ID NO 2
<211> LENGTH: 363
<212> TYPE: PRT
<213> ORGANISM: Methylomonas sp.16a

<400> SEQUENCE: 2

```
Met Asn Gly Pro Gln Pro Leu Ile Thr Asn Pro Gln Leu Leu Ser Gln
1               5                   10                  15

Leu Ser Asp Ala Glu Leu Gln Ala Val Leu Leu Glu Gly Val Ser Arg
            20                  25                  30

Thr Phe Ala Leu Thr Ile Pro Gln Leu Pro Glu Asn Leu Tyr Pro Ala
        35                  40                  45

Val Ala Asn Ala Tyr Leu Leu Cys Arg Ile Val Asp Thr Ile Glu Asp
    50                  55                  60

Glu Ile Ser Leu Asn Ala Glu Gln Lys Lys Arg Phe Cys Ser Glu Phe
65                  70                  75                  80
```

-continued

```
Ile Gln Ile Val Lys Thr Gly Glu Gly Ala Gln Ala Phe Ala Asp Glu
                85                  90                  95

Leu Ala Pro Leu Leu Ser Thr Gln Thr Ile Pro Ala Glu His Ser Leu
            100                 105                 110

Ile His Leu Ile Pro Arg Val Ile Ala Ile Thr His Ser Leu Asp Arg
        115                 120                 125

Ala Gln Ile Glu Ala Leu Ala Cys Cys Val Glu Thr Met Ala Asn Gly
    130                 135                 140

Met Pro Val Tyr Gln Ala Leu Asp Leu Arg Ala Gly Leu Lys Thr Met
145                 150                 155                 160

Lys Asp Met Asp Asp Tyr Cys Tyr Val Ala Gly Cys Val Gly Glu
                165                 170                 175

Met Leu Ala Lys Leu Phe Cys His Tyr Ser Pro Gln Ile Asp Ala His
            180                 185                 190

Arg Asp Glu Leu Leu Lys Leu Ser Val Ser Phe Gly Gln Gly Leu Gln
        195                 200                 205

Met Thr Asn Ile Leu Lys Asp Ile Trp Asp Asp Ala Gln Arg Gly Val
    210                 215                 220

Cys Trp Leu Pro Gln Asp Ile Phe Thr Glu Thr Gly Phe Asn Leu Ala
225                 230                 235                 240

Asp Leu Thr Pro Thr Thr Asn Asp Glu Arg Phe Arg Lys Gly Leu Glu
                245                 250                 255

His Leu Ile Ser Ile Ala His Gly His Leu Gln Asn Ala Leu Thr Tyr
            260                 265                 270

Thr Gln Leu Leu Pro Arg His Glu Thr Gly Ile Arg Asn Phe Cys Leu
        275                 280                 285

Trp Ala Leu Gly Met Ala Val Leu Thr Leu Lys Lys Ile Lys Gln Asn
    290                 295                 300

Leu Ser Phe Asn Glu Ser Ser Gln Val Lys Ile Ser Arg Asn Ser Val
305                 310                 315                 320

Lys Ala Thr Ile Leu Ala Cys Lys Leu Ser Ala Arg Ser Asn Leu Leu
                325                 330                 335

Leu Ser Leu Leu Phe Asn Leu Thr Ser Gln Gly Leu Lys Thr Pro Gly
            340                 345                 350

Trp Gln Tyr Leu Pro Glu Ser His Thr Gly Gln
        355                 360
```

<210> SEQ ID NO 3
<211> LENGTH: 1536
<212> TYPE: DNA
<213> ORGANISM: Methylomonas sp.16a

<400> SEQUENCE: 3

```
atggccaaca ccaaacacat catcatcgtc ggcgcgggtc ccggcggact ttgcgccggc      60
atgttgctga gccagcgcgg cttcaaggta tcgattttcg acaaacatgc agaaatcggc     120
ggccgcaacc gcccgatcaa catgaacggc tttaccttcg ataccggtcc gacattcttg     180
ttgatgaaag gcgtgctgga cgaaatgttc gaactgtgcg agcgccgtag cgaggattat     240
ctggaattcc tgccgctaag cccgatgtac cgcctgctgt acgacgaccg cgacatcttc     300
gtctattccg accgcgagaa catgcgcgcc gaattgcaac gggtattcga cgaaggcacg     360
gacggctacg aacagttcat ggaacaggaa cgcaaacgct tcaacgcgct gtatcccctgc    420
atcacccgcg attattccag cctgaaatcc tttttgtcgc tggacttgat caaggccctg     480
```

```
ccgtggctgg cttttccgaa aagcgtgttc aataatctcg gccagtattt caaccaggaa    540
aaaatgcgcc tggccttttg ctttcagtcc aagtatctgg gcatgtcgcc gtgggaatgc    600
ccggcactgt ttacgatgct gccctatctg gagcacgaat acggcattta tcacgtcaaa    660
ggcggcctga accgcatcgc ggcggcgatg gcgcaagtga tcgcggaaaa cggcggcgaa    720
attcacttga acagcgaaat cgagtcgctg atcatcgaaa acggcgctgc caagggcgtc    780
aaattacaac atggcgcgga gctgcgcggc gacgaagtca tcatcaacgc ggattttgcc    840
cacgcgatga cgcatctggt caaaccgggc gtcttgaaaa aatacacccc ggaaaacctg    900
aagcagcgcg agtattcctg ttcgaccttc atgctgtatc tgggtttgga caagatttac    960
gatctgccgc accataccat cgtgtttgcc aaggattaca ccaccaatat ccgcaacatt   1020
ttcgacaaca aaccctgac ggacgatttt tcgttttacg tgcaaaacgc cagcgccagc   1080
gacgacagcc tagcgccagc cggcaaatcg cgctgtacg tgctggtgcc gatgcccaac   1140
aacgacagcg gcctggactg gcaggcgcat tgccaaaacg tgcgcgaaca ggtgttggac   1200
acgctgggcg cgcgactggg attgagcgac atcagagccc atatcgaatg cgaaaaaatc   1260
atcacgccgc aaacctggga aacgacgaa cacgtttaca agggcgccac tttcagtttg   1320
tcgcacaagt tcagccaaat gctgtactgg cggccgcaca accgtttcga ggaactggcc   1380
aattgctatc tggtcggcgg cggcacgcat cccggtagcg gtttgccgac catctacgaa   1440
tcggcgcgga tttcggccaa gctgatttcc cagaaacatc gggtgaggtt caaggacata   1500
gcacacagcg cctggctgaa aaagccaaa gcctga                                1536
```

<210> SEQ ID NO 4
<211> LENGTH: 511
<212> TYPE: PRT
<213> ORGANISM: Methylomonas sp.16a

<400> SEQUENCE: 4

```
Met Ala Asn Thr Lys His Ile Ile Ile Val Gly Ala Gly Pro Gly Gly
 1               5                  10                  15

Leu Cys Ala Gly Met Leu Leu Ser Gln Arg Gly Phe Lys Val Ser Ile
            20                  25                  30

Phe Asp Lys His Ala Glu Ile Gly Gly Arg Asn Arg Pro Ile Asn Met
        35                  40                  45

Asn Gly Phe Thr Phe Asp Thr Gly Pro Thr Phe Leu Leu Met Lys Gly
    50                  55                  60

Val Leu Asp Glu Met Phe Glu Leu Cys Glu Arg Ser Glu Asp Tyr
65                  70                  75                  80

Leu Glu Phe Leu Pro Leu Ser Pro Met Tyr Arg Leu Leu Tyr Asp Asp
                85                  90                  95

Arg Asp Ile Phe Val Tyr Ser Asp Arg Glu Asn Met Arg Ala Glu Leu
            100                 105                 110

Gln Arg Val Phe Asp Glu Gly Thr Asp Gly Tyr Glu Gln Phe Met Glu
        115                 120                 125

Gln Glu Arg Lys Arg Phe Asn Ala Leu Tyr Pro Cys Ile Thr Arg Asp
    130                 135                 140

Tyr Ser Ser Leu Lys Ser Phe Leu Ser Leu Asp Leu Ile Lys Ala Leu
145                 150                 155                 160

Pro Trp Leu Ala Phe Pro Lys Ser Val Phe Asn Asn Leu Gly Gln Tyr
                165                 170                 175

Phe Asn Gln Glu Lys Met Arg Leu Ala Phe Cys Phe Gln Ser Lys Tyr
            180                 185                 190
```

```
Leu Gly Met Ser Pro Trp Glu Cys Pro Ala Leu Phe Thr Met Leu Pro
        195                 200                 205
Tyr Leu Glu His Glu Tyr Gly Ile Tyr His Val Lys Gly Gly Leu Asn
    210                 215                 220
Arg Ile Ala Ala Ala Met Ala Gln Val Ile Ala Glu Asn Gly Gly Glu
225                 230                 235                 240
Ile His Leu Asn Ser Glu Ile Glu Ser Leu Ile Ile Glu Asn Gly Ala
                245                 250                 255
Ala Lys Gly Val Lys Leu Gln His Gly Ala Glu Leu Arg Gly Asp Glu
            260                 265                 270
Val Ile Ile Asn Ala Asp Phe Ala His Ala Met Thr His Leu Val Lys
        275                 280                 285
Pro Gly Val Leu Lys Lys Tyr Thr Pro Glu Asn Leu Lys Gln Arg Glu
    290                 295                 300
Tyr Ser Cys Ser Thr Phe Met Leu Tyr Leu Gly Leu Asp Lys Ile Tyr
305                 310                 315                 320
Asp Leu Pro His His Thr Ile Val Phe Ala Lys Asp Tyr Thr Thr Asn
                325                 330                 335
Ile Arg Asn Ile Phe Asp Asn Lys Thr Leu Thr Asp Asp Phe Ser Phe
            340                 345                 350
Tyr Val Gln Asn Ala Ser Ala Ser Asp Asp Ser Leu Ala Pro Ala Gly
        355                 360                 365
Lys Ser Ala Leu Tyr Val Leu Val Pro Met Pro Asn Asn Asp Ser Gly
    370                 375                 380
Leu Asp Trp Gln Ala His Cys Gln Asn Val Arg Glu Gln Val Leu Asp
385                 390                 395                 400
Thr Leu Gly Ala Arg Leu Gly Leu Ser Asp Ile Arg Ala His Ile Glu
                405                 410                 415
Cys Glu Lys Ile Ile Thr Pro Gln Thr Trp Glu Thr Asp Glu His Val
            420                 425                 430
Tyr Lys Gly Ala Thr Phe Ser Leu Ser His Lys Phe Ser Gln Met Leu
        435                 440                 445
Tyr Trp Arg Pro His Asn Arg Phe Glu Glu Leu Ala Asn Cys Tyr Leu
    450                 455                 460
Val Gly Gly Gly Thr His Pro Gly Ser Gly Leu Pro Thr Ile Tyr Glu
465                 470                 475                 480
Ser Ala Arg Ile Ser Ala Lys Leu Ile Ser Gln Lys His Arg Val Arg
                485                 490                 495
Phe Lys Asp Ile Ala His Ser Ala Trp Leu Lys Lys Ala Lys Ala
            500                 505                 510

<210> SEQ ID NO 5
<211> LENGTH: 1593
<212> TYPE: DNA
<213> ORGANISM: Methylomonas sp.16a

<400> SEQUENCE: 5
atgacgacga tagcagccgt ctcccccactg atggccgct tgctgggaca ttttccagtc    60
agcaagccgg cgctcattca gcaacagctg acaaaatccc gccgcgccgc cctgctttgg   120
cgcgagctgc cggtcacgga acgggtcaaa cgcctgtcgc ccttgaaaaa acagctgctg   180
gataacctgg acagactctg cgaaaccatc cgcctcagca ccggcaaggt tcgcaccgag   240
gccttgctgg gggaaattta tccggtgctg gatttactgg cgtattacca aaagcgggcg   300
```

```
ccgcggattc tacgcacgcg cgccgtgtcc acctcgccgt tcgcgtttcc ggccgccacc    360
gcccgcatcg aacgccgccc ttacggcgtg gtcgcggtga tctcgccatg gaattacccg    420
tttcacctga gcgtcgcccc gctgctgacc gctttgctgg ccggcaatgc ggtaatcctg    480
aaaccctccg aactctgctt gccggtcggt cagttgatcg tcgatttgtt cgccacgctg    540
gatttgccgg acgggttggt gcaatgggtc atcggcgacg ccaaaccgg cgcggaactg     600
atagacgccc gccccgatct ggtgtttttc accggcggcc tgcagaccgg tcgggcggtc    660
atgcaacgcg ccgcccggca tccgattccg gtcatgctgg agttgggcgg taaagacacc    720
atgctggtgc tggccgacgc cgacctcaag cgcgccagcg ctgccgcgct gtacggcgcg    780
ttttgcaata gcggccaagt ctgcgtctcg gtcgaacgtc tgtacgtgca acaagcctgt    840
tttgcggaat tcctggccat gctgctgaag ggcctgtcca agctcaaggt cggccatgac    900
ccgcacggcg atgtgggagt gatgacgtcc gcccggcaaa tcgacatcgt ccaggcccat    960
tacgaggacg ccatcgccca gggcgccaag gcctccggcc cgctgctgcg cgacggcaat   1020
gtcgtgcaac ccgtggtgct ttgggacgtg caccacggca tgaaggtcat gcgcgaggaa   1080
accttcggtc cgttgctgcc ggtcatgccg ttcagcgacg aagccgaggc catcaagctc   1140
gccaacgaca gcgatctggg tctaaacgcc agcatctgga gccaggatat aatcaaggcc   1200
gagcgccttg ctggacaact agatgtcggc aactgggcga tcaacgacgt attgaaaaac   1260
gtgggccatt ccggcctgcc cttcggcggc gtcaagcaaa gcgggtttgg ccgttatcac   1320
ggcgccgaag gcttgctgaa cttcagctac ccggtatcgg gcctgaccaa tcgcagccgc   1380
ttgcccaaag aacccaactg gttcccttac agcgcatcag gctatgaaaa tttcaagggt   1440
ttcctcgatt ttatctacgg cgaagactcg atgctgcagc gcggtcgccg caatcagcaa   1500
gcgctgcaag ccttccgcga gttttccatt ttcgattgga cacaacgctg gcaaaacctg   1560
aaactgctgt tttcttggac acgggatgac taa                                1593
```

<210> SEQ ID NO 6
<211> LENGTH: 530
<212> TYPE: PRT
<213> ORGANISM: Methylomonas sp.16a

<400> SEQUENCE: 6

```
Met Thr Thr Ile Ala Ala Val Ser Pro Leu Asp Gly Arg Leu Leu Gly
1               5                  10                  15

His Phe Pro Val Ser Lys Pro Ala Leu Ile Gln Gln Gln Leu Thr Lys
            20                  25                  30

Ser Arg Arg Ala Ala Leu Leu Trp Arg Glu Leu Pro Val Thr Glu Arg
        35                  40                  45

Val Lys Arg Leu Ser Pro Leu Lys Lys Gln Leu Leu Asp Asn Leu Asp
    50                  55                  60

Arg Leu Cys Glu Thr Ile Arg Leu Ser Thr Gly Lys Val Arg Thr Glu
65                  70                  75                  80

Ala Leu Leu Gly Glu Ile Tyr Pro Val Leu Asp Leu Leu Ala Tyr Tyr
                85                  90                  95

Gln Lys Arg Ala Pro Arg Ile Leu Arg Thr Arg Ala Val Ser Thr Ser
            100                 105                 110

Pro Phe Ala Phe Pro Ala Ala Thr Ala Arg Ile Glu Arg Arg Pro Tyr
        115                 120                 125

Gly Val Val Ala Val Ile Ser Pro Trp Asn Tyr Pro Phe His Leu Ser
    130                 135                 140
```

Val Ala Pro Leu Leu Thr Ala Leu Leu Ala Gly Asn Ala Val Ile Leu
145                 150                 155                 160

Lys Pro Ser Glu Leu Cys Leu Pro Val Gly Gln Leu Ile Val Asp Leu
                165                 170                 175

Phe Ala Thr Leu Asp Leu Pro Asp Gly Leu Val Gln Trp Val Ile Gly
            180                 185                 190

Asp Gly Gln Thr Gly Ala Glu Leu Ile Asp Ala Arg Pro Asp Leu Val
        195                 200                 205

Phe Phe Thr Gly Gly Leu Gln Thr Gly Arg Ala Val Met Gln Arg Ala
    210                 215                 220

Ala Arg His Pro Ile Pro Val Met Leu Glu Leu Gly Gly Lys Asp Thr
225                 230                 235                 240

Met Leu Val Leu Ala Asp Ala Asp Leu Lys Arg Ala Ser Ala Ala Ala
                245                 250                 255

Leu Tyr Gly Ala Phe Cys Asn Ser Gly Gln Val Cys Val Ser Val Glu
                260                 265                 270

Arg Leu Tyr Val Gln Gln Ala Cys Phe Ala Glu Phe Leu Ala Met Leu
                275                 280                 285

Leu Lys Gly Leu Ser Lys Leu Lys Val Gly His Asp Pro His Gly Asp
            290                 295                 300

Val Gly Val Met Thr Ser Ala Arg Gln Ile Asp Ile Val Gln Ala His
305                 310                 315                 320

Tyr Glu Asp Ala Ile Ala Gln Gly Ala Lys Ala Ser Gly Pro Leu Leu
                325                 330                 335

Arg Asp Gly Asn Val Val Gln Pro Val Leu Trp Asp Val His His
            340                 345                 350

Gly Met Lys Val Met Arg Glu Glu Thr Phe Gly Pro Leu Leu Pro Val
            355                 360                 365

Met Pro Phe Ser Asp Glu Ala Glu Ala Ile Lys Leu Ala Asn Asp Ser
    370                 375                 380

Asp Leu Gly Leu Asn Ala Ser Ile Trp Ser Gln Asp Ile Ile Lys Ala
385                 390                 395                 400

Glu Arg Leu Ala Gly Gln Leu Asp Val Gly Asn Trp Ala Ile Asn Asp
                405                 410                 415

Val Leu Lys Asn Val Gly His Ser Gly Leu Pro Phe Gly Gly Val Lys
            420                 425                 430

Gln Ser Gly Phe Gly Arg Tyr His Gly Ala Glu Gly Leu Leu Asn Phe
        435                 440                 445

Ser Tyr Pro Val Ser Gly Leu Thr Asn Arg Ser Arg Leu Pro Lys Glu
    450                 455                 460

Pro Asn Trp Phe Pro Tyr Ser Ala Ser Gly Tyr Glu Asn Phe Lys Gly
465                 470                 475                 480

Phe Leu Asp Phe Ile Tyr Gly Glu Asp Ser Met Leu Gln Arg Gly Arg
                485                 490                 495

Arg Asn Gln Gln Ala Leu Gln Ala Phe Arg Glu Phe Ser Ile Phe Asp
            500                 505                 510

Trp Thr Gln Arg Trp Gln Asn Leu Lys Leu Leu Phe Ser Trp Thr Arg
        515                 520                 525

Asp Asp
    530

<210> SEQ ID NO 7
<211> LENGTH: 1494
<212> TYPE: DNA

<213> ORGANISM: Methylomonas sp.16a

<400> SEQUENCE: 7

```
atgaactcaa atgacaacca acgcgtgatc gtgatcggcg ccggcctcgg cggcctgtcc    60
gccgctattt cgctggccac ggccggcttt tccgtgcaac tcatcgaaaa aaacgacaag   120
gtcggcggca agctcaacat catgaccaaa gacggcttta ccttcgatct ggggccgtcc   180
attttgacga tgccgcacat cttcgaggcc ttgttcacag gggccggcaa aaacatggcc   240
gattacgtgc aaatccagaa agtcgaaccg cactggcgca atttcttcga ggacggtagc   300
gtgatcgact tgtgcgaaga cgccgaaacc cagcgccgcg agctggataa acttggcccc   360
ggcacttacg cgcaattcca gcgctttctg gactattcga aaaacctctg cacggaaacc   420
gaagccggtt acttcgccaa gggcctggac ggcttttggg atttactcaa gttttacggc   480
ccgctccgca gcctgctgag tttcgacgtc ttccgcagca tggaccaggg cgtgcgccgc   540
tttatttccg atcccaagtt ggtcgaaatc ctgaattact tcatcaaata cgtcggctcc   600
tcgccttacg atgcgcccgc cttgatgaac ctgctgcctt acattcaata tcattacggc   660
ctgtggtacg tgaaaggcgg catgtatggc atggcgcagg ccatggaaaa actggccgtg   720
gaattgggcg tcgagattcg tttagatgcc gaggtgtcgg aaatccaaaa acaggacggc   780
agagcctgcg ccgtaaagtt ggcgaacggc gacgtgctgc cggccgacat cgtggtgtcg   840
aacatggaag tgattccggc gatggaaaaa ctgctgcgca gcccggccag cgaactgaaa   900
aaaatgcagc gcttcgagcc tagctgttcc ggcctggtgc tgcacttggg cgtggacagg   960
ctgtatccgc aactggcgca ccacaatttc ttttattccg atcatccgcg cgaacatttc  1020
gatgcggtat tcaaaagcca tcgcctgtcg gacgatccga ccatttatct ggtcgcgccg  1080
tgcaagaccg acccccgccca ggcgccggcc ggctgcgaga tcatcaaaat cctgcccat   1140
atcccgcacc tcgaccccga caaactgctg accgccgagg attattcagc cttgcgcgag  1200
cgggtgctgg tcaaactcga acgcatgggc ctgacggatt tacgccaaca catcgtgacc  1260
gaagaatact ggacgccgct ggatattcag gccaaatatt attcaaacca gggctcgatt  1320
tacggcgtgg tcgccgaccg cttcaaaaac ctgggtttca aggcacctca acgcagcagc  1380
gaattatcca atctgtattt cgtcggcggc agcgtcaatc ccggcggcgg catgccgatg  1440
gtgacgctgt ccgggcaatt ggtgagggac aagattgtgg cggatttgca ataa        1494
```

<210> SEQ ID NO 8
<211> LENGTH: 497
<212> TYPE: PRT
<213> ORGANISM: Methylomonas sp.16a

<400> SEQUENCE: 8

```
Met Asn Ser Asn Asp Asn Gln Arg Val Ile Val Ile Gly Ala Gly Leu
1               5                   10                  15

Gly Gly Leu Ser Ala Ala Ile Ser Leu Ala Thr Ala Gly Phe Ser Val
            20                  25                  30

Gln Leu Ile Glu Lys Asn Asp Lys Val Gly Gly Lys Leu Asn Ile Met
        35                  40                  45

Thr Lys Asp Gly Phe Thr Phe Asp Leu Gly Pro Ser Ile Leu Thr Met
    50                  55                  60

Pro His Ile Phe Glu Ala Leu Phe Thr Gly Ala Gly Lys Asn Met Ala
65                  70                  75                  80

Asp Tyr Val Gln Ile Gln Lys Val Glu Pro His Trp Arg Asn Phe Phe
                85                  90                  95
```

```
Glu Asp Gly Ser Val Ile Asp Leu Cys Glu Asp Ala Glu Thr Gln Arg
            100                 105                 110

Arg Glu Leu Asp Lys Leu Gly Pro Gly Thr Tyr Ala Gln Phe Gln Arg
            115                 120                 125

Phe Leu Asp Tyr Ser Lys Asn Leu Cys Thr Glu Thr Glu Ala Gly Tyr
            130                 135                 140

Phe Ala Lys Gly Leu Asp Gly Phe Trp Asp Leu Leu Lys Phe Tyr Gly
145                 150                 155                 160

Pro Leu Arg Ser Leu Leu Ser Phe Asp Val Phe Arg Ser Met Asp Gln
            165                 170                 175

Gly Val Arg Arg Phe Ile Ser Asp Pro Lys Leu Val Glu Ile Leu Asn
            180                 185                 190

Tyr Phe Ile Lys Tyr Val Gly Ser Pro Tyr Asp Ala Pro Ala Leu
            195                 200                 205

Met Asn Leu Leu Pro Tyr Ile Gln Tyr His Tyr Gly Leu Trp Tyr Val
210                 215                 220

Lys Gly Gly Met Tyr Gly Met Ala Gln Ala Met Glu Lys Leu Ala Val
225                 230                 235                 240

Glu Leu Gly Val Glu Ile Arg Leu Asp Ala Glu Val Ser Glu Ile Gln
            245                 250                 255

Lys Gln Asp Gly Arg Ala Cys Ala Val Lys Leu Ala Asn Gly Asp Val
            260                 265                 270

Leu Pro Ala Asp Ile Val Val Ser Asn Met Glu Val Ile Pro Ala Met
            275                 280                 285

Glu Lys Leu Leu Arg Ser Pro Ala Ser Glu Leu Lys Lys Met Gln Arg
            290                 295                 300

Phe Glu Pro Ser Cys Ser Gly Leu Val Leu His Leu Gly Val Asp Arg
305                 310                 315                 320

Leu Tyr Pro Gln Leu Ala His His Asn Phe Phe Tyr Ser Asp His Pro
            325                 330                 335

Arg Glu His Phe Asp Ala Val Phe Lys Ser His Arg Leu Ser Asp Asp
            340                 345                 350

Pro Thr Ile Tyr Leu Val Ala Pro Cys Lys Thr Asp Pro Ala Gln Ala
            355                 360                 365

Pro Ala Gly Cys Glu Ile Ile Lys Ile Leu Pro His Ile Pro His Leu
            370                 375                 380

Asp Pro Asp Lys Leu Leu Thr Ala Glu Asp Tyr Ser Ala Leu Arg Glu
385                 390                 395                 400

Arg Val Leu Val Lys Leu Glu Arg Met Gly Leu Thr Asp Leu Arg Gln
            405                 410                 415

His Ile Val Thr Glu Glu Tyr Trp Thr Pro Leu Asp Ile Gln Ala Lys
            420                 425                 430

Tyr Tyr Ser Asn Gln Gly Ser Ile Tyr Gly Val Val Ala Asp Arg Phe
            435                 440                 445

Lys Asn Leu Gly Phe Lys Ala Pro Gln Arg Ser Ser Glu Leu Ser Asn
450                 455                 460

Leu Tyr Phe Val Gly Gly Ser Val Asn Pro Gly Gly Met Pro Met
465                 470                 475                 480

Val Thr Leu Ser Gly Gln Leu Val Arg Asp Lys Ile Val Ala Asp Leu
            485                 490                 495

Gln
```

<210> SEQ ID NO 9
<211> LENGTH: 864
<212> TYPE: DNA
<213> ORGANISM: Staphylococcus aureus

<400> SEQUENCE: 9

```
atgacaatga tggatatgaa ttttaaatat tgtcataaaa tcatgaagaa acattcaaaa      60
agcttttctt acgcttttga cttgttacca gaagatcaaa gaaaagcggt ttgggcaatt     120
tatgctgtgt gtcgtaaaat tgatgacagt atagatgttt atggcgatat tcaattttta     180
aatcaaataa agaagatat acaatctatt gaaaaatacc catatgaaca tcatcacttt     240
caaagtgatc gtagaatcat gatggcgctt cagcatgttg cacaacataa aaatatcgcc     300
tttcaatctt tttataatct cattgatact gtatataaag atcaacattt tacaatgttt     360
gaaacggacg ctgaattatt cggatattgt tatggtgttg ctggtacagt aggtgaagta     420
ttgacgccga ttttaagtga tcatgaaaca catcagacat acgatgtcgc aagaagactt     480
ggtgaatcgt tgcaattgat taatatatta agagatgtcg gtgaagattt tgacaatgaa     540
cggatatatt ttagtaagca acgattaaag caatatgaag ttgatattgc tgaagtgtac     600
caaaatggtg ttaataatca ttatattgac ttatgggaat attatgcagc tatcgcagaa     660
aaagattttc aagatgttat ggatcaaatc aaagtattta gtattgaagc acaaccaatc     720
atagaattag cagcacgtat atatattgaa atactggacg aagtgagaca ggctaactat     780
acattacatg aacgtgtttt tgtggataag aggaaaaagg caaagttgtt tcatgaaata     840
aatagtaaat atcatagaat atag                                            864
```

<210> SEQ ID NO 10
<211> LENGTH: 287
<212> TYPE: PRT
<213> ORGANISM: Staphylococcus aureus

<400> SEQUENCE: 10

```
Met Thr Met Met Asp Met Asn Phe Lys Tyr Cys His Lys Ile Met Lys
1               5                   10                  15

Lys His Ser Lys Ser Phe Ser Tyr Ala Phe Asp Leu Leu Pro Glu Asp
            20                  25                  30

Gln Arg Lys Ala Val Trp Ala Ile Tyr Ala Val Cys Arg Lys Ile Asp
        35                  40                  45

Asp Ser Ile Asp Val Tyr Gly Asp Ile Gln Phe Leu Asn Gln Ile Lys
    50                  55                  60

Glu Asp Ile Gln Ser Ile Glu Lys Tyr Pro Tyr Glu His His His Phe
65                  70                  75                  80

Gln Ser Asp Arg Arg Ile Met Met Ala Leu Gln His Val Ala Gln His
                85                  90                  95

Lys Asn Ile Ala Phe Gln Ser Phe Tyr Asn Leu Ile Asp Thr Val Tyr
            100                 105                 110

Lys Asp Gln His Phe Thr Met Phe Glu Thr Asp Ala Glu Leu Phe Gly
        115                 120                 125

Tyr Cys Tyr Gly Val Ala Gly Thr Val Gly Glu Val Leu Thr Pro Ile
    130                 135                 140

Leu Ser Asp His Glu Thr His Gln Thr Tyr Asp Val Ala Arg Arg Leu
145                 150                 155                 160

Gly Glu Ser Leu Gln Leu Ile Asn Ile Leu Arg Asp Val Gly Glu Asp
                165                 170                 175

Phe Asp Asn Glu Arg Ile Tyr Phe Ser Lys Gln Arg Leu Lys Gln Tyr
```

```
                    180              185              190
Glu Val Asp Ile Ala Glu Val Tyr Gln Asn Gly Val Asn Asn His Tyr
                195              200              205

Ile Asp Leu Trp Glu Tyr Tyr Ala Ala Ile Ala Glu Lys Asp Phe Gln
    210              215              220

Asp Val Met Asp Gln Ile Lys Val Phe Ser Ile Glu Ala Gln Pro Ile
225              230              235              240

Ile Glu Leu Ala Ala Arg Ile Tyr Ile Glu Ile Leu Asp Glu Val Arg
                245              250              255

Gln Ala Asn Tyr Thr Leu His Glu Arg Val Phe Val Asp Lys Arg Lys
                260              265              270

Lys Ala Lys Leu Phe His Glu Ile Asn Ser Lys Tyr His Arg Ile
                275              280              285

<210> SEQ ID NO 11
<211> LENGTH: 1509
<212> TYPE: DNA
<213> ORGANISM: Staphylococcus aureus

<400> SEQUENCE: 11
atgaagattg cagtaattgg tgcaggtgtc acaggattag cagcggcagc ccgtattgct      60
tctcaaggtc atgaagtgac gatatttgaa aaaataataa tgtaggcgg gcgtatgaat     120
caattaaaga aagacggctt tacatttgat atgggtccca caattgtcat gatgccagat     180
gtttataaag atgtttttac agcgtgtggt aaaaattatg aagattatat tgaattgaga     240
caattacgtt atatttacga tgtgtatttt gaccacgatg atcgtataac ggtgcctaca     300
gatttagctg aattacagca aatgctagaa agtatagaac ctggttcaac gcatggtttt     360
atgtcctttt taacggatgt ttataaaaaa tatgaaattg cacgtcgcta tttcttagaa     420
agaacgtatc gcaaaccgag tgacttttat aatatgacgt cacttgtgca aggtgctaag     480
ttaaaaacgt taaatcatgc agatcagcta attgaacatt atattgataa cgaaaagata     540
caaaagcttt tagcgtttca aacgttatac ataggaattg atccaaaacg aggcccgtca     600
ctatattcaa ttattcctat gattgaaatg atgtttggtg tgcatttta  taaaggcggt     660
atgtatggca tggctcaagg gctagcgcaa ttaaataaag acttaggcgt taatattgaa     720
ctaaatgctg aaattgagca aattattatt gatcctaaat tcaaacgggc cgatgcgata     780
aaagtgaatg gtgacataag aaaatttgat aaaattttat gtacggctga tttccctagt     840
gttgcggaat cattaatgcc agattttgca cctattaaaa agtatccacc acataaaatt     900
gcagacttag attactcttg ttcagcattt ttaatgtata tcggtataga tattgatgtg     960
acagatcaag tgagacttca taatgttatt ttttcagatg actttagagg caatattgaa    1020
gaaatatttg agggacgttt atcatatgat ccttctattt atgtgtatgt accagcggtc    1080
gctgataaat cacttgcgcc agaaggcaaa actggtattt atgtgctaat gccgacgccg    1140
gaacttaaaa caggtagcgg aatcgattgg tcagatgaag ctttgacgca caaataaag    1200
gaaattattt atcgtaaatt agcaacgatt gaagtatttg aagatataaa atcgcatatt    1260
gtttcagaaa caatctttac gccaaatgat tttgagcaaa cgtatcatgc gaaatttggt    1320
tcggcattcg gttaatgcc aactttagcg caaagtaatt attatcgtcc acaaaatgta    1380
tcgcgagatt ataagatttt atattttgca ggtgcaagta cgcatccagg tgcaggcgtt    1440
cctattgtct taacgagtgc gaaaataact gtagatgaaa tgattaaaga tattgagcgg    1500
ggcgtataa                                                            1509
```

<210> SEQ ID NO 12
<211> LENGTH: 502
<212> TYPE: PRT
<213> ORGANISM: Staphylococcus aureus

<400> SEQUENCE: 12

```
Met Lys Ile Ala Val Ile Gly Ala Gly Val Thr Gly Leu Ala Ala Ala
1               5                   10                  15

Ala Arg Ile Ala Ser Gln Gly His Glu Val Thr Ile Phe Glu Lys Asn
                20                  25                  30

Asn Asn Val Gly Gly Arg Met Asn Gln Leu Lys Lys Asp Gly Phe Thr
            35                  40                  45

Phe Asp Met Gly Pro Thr Ile Val Met Met Pro Asp Val Tyr Lys Asp
    50                  55                  60

Val Phe Thr Ala Cys Gly Lys Asn Tyr Glu Asp Tyr Ile Glu Leu Arg
65                  70                  75                  80

Gln Leu Arg Tyr Ile Tyr Asp Val Tyr Phe Asp His Asp Asp Arg Ile
                85                  90                  95

Thr Val Pro Thr Asp Leu Ala Glu Leu Gln Gln Met Leu Glu Ser Ile
                100                 105                 110

Glu Pro Gly Ser Thr His Gly Phe Met Ser Phe Leu Thr Asp Val Tyr
            115                 120                 125

Lys Lys Tyr Glu Ile Ala Arg Arg Tyr Phe Leu Glu Arg Thr Tyr Arg
    130                 135                 140

Lys Pro Ser Asp Phe Tyr Asn Met Thr Ser Leu Val Gln Gly Ala Lys
145                 150                 155                 160

Leu Lys Thr Leu Asn His Ala Asp Gln Leu Ile Glu His Tyr Ile Asp
                165                 170                 175

Asn Glu Lys Ile Gln Lys Leu Leu Ala Phe Gln Thr Leu Tyr Ile Gly
                180                 185                 190

Ile Asp Pro Lys Arg Gly Pro Ser Leu Tyr Ser Ile Ile Pro Met Ile
            195                 200                 205

Glu Met Met Phe Gly Val His Phe Ile Lys Gly Gly Met Tyr Gly Met
    210                 215                 220

Ala Gln Gly Leu Ala Gln Leu Asn Lys Asp Leu Gly Val Asn Ile Glu
225                 230                 235                 240

Leu Asn Ala Glu Ile Glu Gln Ile Ile Asp Pro Lys Phe Lys Arg
                245                 250                 255

Ala Asp Ala Ile Lys Val Asn Gly Asp Ile Arg Lys Phe Asp Lys Ile
            260                 265                 270

Leu Cys Thr Ala Asp Phe Pro Ser Val Ala Glu Ser Leu Met Pro Asp
        275                 280                 285

Phe Ala Pro Ile Lys Lys Tyr Pro Pro His Lys Ile Ala Asp Leu Asp
    290                 295                 300

Tyr Ser Cys Ser Ala Phe Leu Met Tyr Ile Gly Ile Asp Ile Asp Val
305                 310                 315                 320

Thr Asp Gln Val Arg Leu His Asn Val Ile Phe Ser Asp Asp Phe Arg
                325                 330                 335

Gly Asn Ile Glu Glu Ile Phe Glu Gly Arg Leu Ser Tyr Asp Pro Ser
            340                 345                 350

Ile Tyr Val Tyr Val Pro Ala Val Ala Asp Lys Ser Leu Ala Pro Glu
        355                 360                 365

Gly Lys Thr Gly Ile Tyr Val Leu Met Pro Thr Pro Glu Leu Lys Thr
```

```
                370             375             380
Gly Ser Gly Ile Asp Trp Ser Asp Glu Ala Leu Thr Gln Gln Ile Lys
385                 390                 395                 400

Glu Ile Ile Tyr Arg Lys Leu Ala Thr Ile Glu Val Phe Glu Asp Ile
                405                 410                 415

Lys Ser His Ile Val Ser Glu Thr Ile Phe Thr Pro Asn Asp Phe Glu
            420                 425                 430

Gln Thr Tyr His Ala Lys Phe Gly Ser Ala Phe Gly Leu Met Pro Thr
        435                 440                 445

Leu Ala Gln Ser Asn Tyr Tyr Arg Pro Gln Asn Val Ser Arg Asp Tyr
    450                 455                 460

Lys Asp Leu Tyr Phe Ala Gly Ala Ser Thr His Pro Gly Ala Gly Val
465                 470                 475                 480

Pro Ile Val Leu Thr Ser Ala Lys Ile Thr Val Asp Glu Met Ile Lys
                485                 490                 495

Asp Ile Glu Arg Gly Val
            500

<210> SEQ ID NO 13
<211> LENGTH: 1494
<212> TYPE: DNA
<213> ORGANISM: Staphylococcus aureus

<400> SEQUENCE: 13
atgactaaac atatcatcgt tattggtggt ggcttaggtg ggatttctgc agcaattcga      60
atggcacaaa gtggctattc ggtctcatta tatgaacaaa ataatcatat aggaggcaaa     120
gtgaatcgtc atgaatcaga tggctttggc tttgatttag gtccatctat tttaacgatg     180
ccttatattt ttgaaaaatt attcgaatat agcaagaagc aaatgtcaga ctacgttaca     240
atcaagcgat tgccacatca atggcgtagc ttttttccag atggaacgac atcgatttg      300 tatgaaggta ttaaagaaac aggtcagcat aatgcgatat tgtcgaaaca ggatatagag     360
gaactgcaaa attatttgaa ttatacaaga cgaatcgatc gtattactga aaaagggtat     420
ttcaactatg gtttagatac actatctcaa attattaaat ttcatgggcc attaaatgct     480
cttattaatt atgattatgt acatactatg caacaggcca tagacaagcg tatctcgaat     540
ccatacttgc gacaaatgtt aggctatttt atcaaatatg taggttcttc atcatacgat     600
gcgccagctg tattatctat gttattccat atgcaacaag agcaaggcct ttggtatgta     660
gaaggtggaa tccatcattt agccaatgcc ttggaaaagc tagcgcgtga agaaggtgtc     720
acaattcata caggtgcacg tgtggacaat attaaaacat atcaaagacg tgtgacgggt     780
gtcagattag atacaggtga gtttgtaaag gcagattata ttatttcaaa tatggaagtc     840 ataccctactt ataaatattt aattcacctt gatactcaac gattaaacaa attagagagg     900
gaatttgagc cggcaagctc aggatatgtg atgcatttag gtgttgcttg ccaatacccg     960
caattagcac atcataattt ctttttacg gaaatgcttt atctcaatta tcaacaagtt    1020
tttcatgaaa aggtattgcc agatgatccg accattatc tagtaaatac gaataaaact    1080
gatcacacac aagcgccagt aggttatgaa aatatcaaag tcttaccaca tattccatat    1140
attcaagatc agccttttac cactgaagat tatgcgaagt ttagggataa aattttggat    1200
aaattagaaa aaatgggact tactgattta agaaaacaca ttatttatga agatgtttgg    1260 acaccgagg atattgaaaa aaattatcgt tctaatcgtg gtgcaatata tggtgttgta    1320
gcagataaaa agaaaaacaa aggatttaaa tttcctaaag aaagtcagta ttttgaaaac    1380
```

-continued

```
ttgtactttg taggtggatc agtaaatcct ggtggtggca tgccaatggt tacattaagt    1440
gggcaacaag tcgcagacaa aataaacgcg cgagaagcga agaataggaa gtga          1494
```

<210> SEQ ID NO 14
<211> LENGTH: 497
<212> TYPE: PRT
<213> ORGANISM: Staphylococcus aureus

<400> SEQUENCE: 14

```
Met Thr Lys His Ile Ile Val Ile Gly Gly Gly Leu Gly Gly Ile Ser
1               5                   10                  15

Ala Ala Ile Arg Met Ala Gln Ser Gly Tyr Ser Val Ser Leu Tyr Glu
            20                  25                  30

Gln Asn Asn His Ile Gly Gly Lys Val Asn Arg His Glu Ser Asp Gly
        35                  40                  45

Phe Gly Phe Asp Leu Gly Pro Ser Ile Leu Thr Met Pro Tyr Ile Phe
    50                  55                  60

Glu Lys Leu Phe Glu Tyr Ser Lys Lys Gln Met Ser Asp Tyr Val Thr
65                  70                  75                  80

Ile Lys Arg Leu Pro His Gln Trp Arg Ser Phe Phe Pro Asp Gly Thr
                85                  90                  95

Thr Ile Asp Leu Tyr Glu Gly Ile Lys Glu Thr Gly Gln His Asn Ala
            100                 105                 110

Ile Leu Ser Lys Gln Asp Ile Glu Glu Leu Gln Asn Tyr Leu Asn Tyr
        115                 120                 125

Thr Arg Arg Ile Asp Arg Ile Thr Glu Lys Gly Tyr Phe Asn Tyr Gly
    130                 135                 140

Leu Asp Thr Leu Ser Gln Ile Ile Lys Phe His Gly Pro Leu Asn Ala
145                 150                 155                 160

Leu Ile Asn Tyr Asp Tyr Val His Thr Met Gln Gln Ala Ile Asp Lys
                165                 170                 175

Arg Ile Ser Asn Pro Tyr Leu Arg Gln Met Leu Gly Tyr Phe Ile Lys
            180                 185                 190

Tyr Val Gly Ser Ser Ser Tyr Asp Ala Pro Ala Val Leu Ser Met Leu
        195                 200                 205

Phe His Met Gln Gln Glu Gln Gly Leu Trp Tyr Val Glu Gly Gly Ile
    210                 215                 220

His His Leu Ala Asn Ala Leu Glu Lys Leu Ala Arg Glu Glu Gly Val
225                 230                 235                 240

Thr Ile His Thr Gly Ala Arg Val Asp Asn Ile Lys Thr Tyr Gln Arg
                245                 250                 255

Arg Val Thr Gly Val Arg Leu Asp Thr Gly Glu Phe Val Lys Ala Asp
            260                 265                 270

Tyr Ile Ile Ser Asn Met Glu Val Ile Pro Thr Tyr Lys Tyr Leu Ile
        275                 280                 285

His Leu Asp Thr Gln Arg Leu Asn Lys Leu Glu Arg Glu Phe Glu Pro
    290                 295                 300

Ala Ser Ser Gly Tyr Val Met His Leu Gly Val Ala Cys Gln Tyr Pro
305                 310                 315                 320

Gln Leu Ala His His Asn Phe Phe Thr Glu Asn Ala Tyr Leu Asn
                325                 330                 335

Tyr Gln Gln Val Phe His Glu Lys Val Leu Pro Asp Asp Pro Thr Ile
            340                 345                 350
```

```
Tyr Leu Val Asn Thr Asn Lys Thr Asp His Thr Gln Ala Pro Val Gly
        355                 360                 365

Tyr Glu Asn Ile Lys Val Leu Pro His Ile Pro Tyr Ile Gln Asp Gln
        370                 375                 380

Pro Phe Thr Thr Glu Asp Tyr Ala Lys Phe Arg Asp Lys Ile Leu Asp
385                 390                 395                 400

Lys Leu Glu Lys Met Gly Leu Thr Asp Leu Arg Lys His Ile Ile Tyr
                405                 410                 415

Glu Asp Val Trp Thr Pro Glu Asp Ile Glu Lys Asn Tyr Arg Ser Asn
                420                 425                 430

Arg Gly Ala Ile Tyr Gly Val Val Ala Asp Lys Lys Asn Lys Gly
            435                 440                 445

Phe Lys Phe Pro Lys Glu Ser Gln Tyr Phe Glu Asn Leu Tyr Phe Val
        450                 455                 460

Gly Gly Ser Val Asn Pro Gly Gly Met Pro Met Val Thr Leu Ser
465                 470                 475                 480

Gly Gln Gln Val Ala Asp Lys Ile Asn Ala Arg Glu Ala Lys Asn Arg
                485                 490                 495

Lys
```

<210> SEQ ID NO 15
<211> LENGTH: 27
<212> TYPE: DNA
<213> ORGANISM: Artificial Sequence
<220> FEATURE:
<223> OTHER INFORMATION: Primer crtM_F/Staphyl

<400> SEQUENCE: 15
atgacaatga tggatatgaa ttttaaa                                          27

<210> SEQ ID NO 16
<211> LENGTH: 35
<212> TYPE: DNA
<213> ORGANISM: Artificial Sequence
<220> FEATURE:
<223> OTHER INFORMATION: Primer crtM_R/Staphyl

<400> SEQUENCE: 16
ggatcctata ttctatgata tttactattt atttc                                 35

<210> SEQ ID NO 17
<211> LENGTH: 36
<212> TYPE: DNA
<213> ORGANISM: Artificial Sequence
<220> FEATURE:
<223> OTHER INFORMATION: Primer crtN_FL

<400> SEQUENCE: 17
ggtctcaaat tgcatcaacg gatcatcatg gccaac                                36

<210> SEQ ID NO 18
<211> LENGTH: 44
<212> TYPE: DNA
<213> ORGANISM: Artificial Sequence
<220> FEATURE:
<223> OTHER INFORMATION: Primer crtN_RL

<400> SEQUENCE: 18
ggtctctaat tgctagctta ttgcaaatcc gccacaatct tgtc                       44

<210> SEQ ID NO 19

```
<211> LENGTH: 23
<212> TYPE: DNA
<213> ORGANISM: Artificial Sequence
<220> FEATURE:
<223> OTHER INFORMATION: Primer Tet-1 FP

<400> SEQUENCE: 19
gggtgcgcat gatcctctag agt                                            23

<210> SEQ ID NO 20
<211> LENGTH: 28
<212> TYPE: DNA
<213> ORGANISM: Artificial Sequence
<220> FEATURE:
<223> OTHER INFORMATION: Primer crtN_R

<400> SEQUENCE: 20
ttattgcaaa tccgccacaa tcttgtcc                                       28

<210> SEQ ID NO 21
<211> LENGTH: 47
<212> TYPE: DNA
<213> ORGANISM: Artificial Sequence
<220> FEATURE:
<223> OTHER INFORMATION: Primer crtM_F/NCTC

<400> SEQUENCE: 21
gaattcagga ggaataaacc atgacaatga tggatatgaa ttttaaa                  47

<210> SEQ ID NO 22
<211> LENGTH: 29
<212> TYPE: DNA
<213> ORGANISM: Artificial Sequence
<220> FEATURE:
<223> OTHER INFORMATION: Primer crtN_R/NCTC

<400> SEQUENCE: 22
gaattcttat acgccccgct caatatctt                                      29

<210> SEQ ID NO 23
<211> LENGTH: 22
<212> TYPE: DNA
<213> ORGANISM: Artificial Sequence
<220> FEATURE:
<223> OTHER INFORMATION: Primer crtN_5'/16a

<400> SEQUENCE: 23
atggccaaca ccaaacacat ca                                             22

<210> SEQ ID NO 24
<211> LENGTH: 28
<212> TYPE: DNA
<213> ORGANISM: Artificial Sequence
<220> FEATURE:
<223> OTHER INFORMATION: Primer crtN_3'/16a

<400> SEQUENCE: 24
ggatcctcag gctttggctt ttttcagc                                       28

<210> SEQ ID NO 25
<211> LENGTH: 23
<212> TYPE: DNA
<213> ORGANISM: Artificial Sequence
<220> FEATURE:
<223> OTHER INFORMATION: Primer crtN2_F3'/16a

<400> SEQUENCE: 25
```

-continued

```
atgaactcaa atgacaacca acg                                           23

<210> SEQ ID NO 26
<211> LENGTH: 28
<212> TYPE: DNA
<213> ORGANISM: Artificial Sequence
<220> FEATURE:
<223> OTHER INFORMATION: Primer crtN2_R/16a

<400> SEQUENCE: 26
gaattctatt gcaaatccgc cacaatct                                      28

<210> SEQ ID NO 27
<211> LENGTH: 49
<212> TYPE: DNA
<213> ORGANISM: Artificial Sequence
<220> FEATURE:
<223> OTHER INFORMATION: Primer crtN_5'_2/16a

<400> SEQUENCE: 27
ggatccaagc ttaaggagga ataaaccatg gccaacacca aacacatca               49

<210> SEQ ID NO 28
<211> LENGTH: 33
<212> TYPE: DNA
<213> ORGANISM: Artificial Sequence
<220> FEATURE:
<223> OTHER INFORMATION: Primer crtN_3'_2/16a

<400> SEQUENCE: 28
ggatccaagc ttcaggcttt ggcttttttc agc                                33

<210> SEQ ID NO 29
<211> LENGTH: 51
<212> TYPE: DNA
<213> ORGANISM: Artificial Sequence
<220> FEATURE:
<223> OTHER INFORMATION: Primer crtN2_5'_2/16a

<400> SEQUENCE: 29
ggatccaagc ttaaggagga ataaaccatg aactcaaatg acaaccaacg c            51

<210> SEQ ID NO 30
<211> LENGTH: 34
<212> TYPE: DNA
<213> ORGANISM: Artificial Sequence
<220> FEATURE:
<223> OTHER INFORMATION: Primer crtN2_3'_2/16a

<400> SEQUENCE: 30
ggatccaagc ttattgcaaa tccgccacaa tctt                               34

<210> SEQ ID NO 31
<211> LENGTH: 61
<212> TYPE: DNA
<213> ORGANISM: Artificial Sequence
<220> FEATURE:
<223> OTHER INFORMATION: Primer 5'-kan(dxs)

<400> SEQUENCE: 31
tggaagcgct agcggactac atcatccagc gtaataaata acgtcttgag cgattgtgta   60
g                                                                   61

<210> SEQ ID NO 32
```

<211> LENGTH: 65
<212> TYPE: DNA
<213> ORGANISM: Artificial Sequence
<220> FEATURE:
<223> OTHER INFORMATION: Primer 5'-kan(idi)

<400> SEQUENCE: 32
tctgatgcgc aagctgaaga aaaatgagca tggagaataa tatgacgtct tgagcgattg    60
tgtag    65

<210> SEQ ID NO 33
<211> LENGTH: 60
<212> TYPE: DNA
<213> ORGANISM: Artificial Sequence
<220> FEATURE:
<223> OTHER INFORMATION: Primer 5'-kan(ispAdxs)

<400> SEQUENCE: 33
accatgacgg ggcgaaaaat attgagagtc agacattcat gtgtaggctg gagctgcttc    60

<210> SEQ ID NO 34
<211> LENGTH: 64
<212> TYPE: DNA
<213> ORGANISM: Artificial Sequence
<220> FEATURE:
<223> OTHER INFORMATION: Primer 3'-kan

<400> SEQUENCE: 34
gaagacgaaa gggcctcgtg atacgcctat ttttataggt tatatgaata tcctccttag    60
ttcc    64

<210> SEQ ID NO 35
<211> LENGTH: 50
<212> TYPE: DNA
<213> ORGANISM: Artificial Sequence
<220> FEATURE:
<223> OTHER INFORMATION: Primer 5'-T5

<400> SEQUENCE: 35
ctaaggagga tattcatata acctataaaa ataggcgtat cacgaggccc    50

<210> SEQ ID NO 36
<211> LENGTH: 70
<212> TYPE: DNA
<213> ORGANISM: Artificial Sequence
<220> FEATURE:
<223> OTHER INFORMATION: Primer 3'-T5(dxs)

<400> SEQUENCE: 36
ggagtcgacc agtgccaggg tcgggtattt ggcaatatca aaactcatag ttaatttctc    60
ctctttaatg    70

<210> SEQ ID NO 37
<211> LENGTH: 68
<212> TYPE: DNA
<213> ORGANISM: Artificial Sequence
<220> FEATURE:
<223> OTHER INFORMATION: Primer 3'-T5(idi)

<400> SEQUENCE: 37
tgggaactcc ctgtgcattc aataaaatga cgtgttccgt ttgcatagtt aatttctcct    60
ctttaatg    68

-continued

<210> SEQ ID NO 38
<211> LENGTH: 62
<212> TYPE: DNA
<213> ORGANISM: Artificial Sequence
<220> FEATURE:
<223> OTHER INFORMATION: Primer 3'-T5(ispAdxs)

<400> SEQUENCE: 38
cctgcttaac gcaggcttcg agttgctgcg gaaagtccat agttaatttc tcctctttaa     60
tg                                                                    62

<210> SEQ ID NO 39
<211> LENGTH: 6329
<212> TYPE: DNA
<213> ORGANISM: Artificial Sequence
<220> FEATURE:
<223> OTHER INFORMATION: Helper plasmid pKD46 (Datsenko and Wanner,
      PNAS. 97:6640-6645 (2000))

<400> SEQUENCE: 39
catcgattta ttatgacaac ttgacggcta catcattcac ttttcttca caaccggcac       60 ggaactcgct cgggctggcc ccggtgcatt ttttaaatac ccgcgagaaa tagagttgat     120
cgtcaaaacc aacattgcga ccgacggtgg cgataggcat ccgggtggtg ctcaaaagca     180
gcttcgcctg gctgatacgt tggtcctcgc gccagcttaa gacgctaatc cctaactgct     240
ggcggaaaag atgtgacaga cgcgacggcg acaagcaaac atgctgtgcg acgctggcga     300
tatcaaaatt gctgtctgcc aggtgatcgc tgatgtactg acaagcctcg cgtacccgat     360
tatccatcgg tggatggagc gactcgttaa tcgcttccat gcgccgcagt aacaattgct     420
caagcagatt tatcgccagc agctccgaat agcgcccttc cccttgcccg gcgttaatga     480
tttgcccaaa caggtcgctg aaatgcggct ggtgcgcttc atccgggcga aagaaccccg     540
tattggcaaa tattgacggc cagttaagcc attcatgcca gtaggcgcgc ggacgaaagt     600
aaacccactg gtgataccat tcgcgagcct ccggatgacg accgtagtga tgaatctctc     660
ctggcgggaa cagcaaaata tcacccggtc ggcaaacaaa ttctcgtccc tgatttttca     720 ccacccctg accgcgaatg gtgagattga gaatataacc tttcattccc agcggtcggt     780
cgataaaaaa atcgagataa ccgttggcct caatcggcgt taaacccgcc accagatggg     840
cattaaacga gtatcccggc agcaggggat cattttgcgc ttcagccata cttttcatac     900
tcccgccatt cagagaagaa accaattgtc catattgcat cagacattgc cgtcactgcg     960
tcttttactg gctcttctcg ctaaccaaac cggtaacccc gcttattaaa agcattctgt    1020
aacaaagcgg gaccaaagcc atgacaaaaa cgcgtaacaa agtgtctat aatcacggca     1080 gaaaagtcca cattgattat ttgcacggcg tcacactttg ctatgccata gcatttttat    1140
ccataagatt agcggatcct acctgacgct tttatcgca actctctact gtttctccat     1200
acccgttttt tgggaattc gagctctaag gaggttataa aaatggata ttaatactga     1260 aactgagatc aagcaaaagc attcactaac ccccttcct gttttcctaa tcagcccggc     1320
atttcgcggg cgatattttc acagctattt caggagttca gccatgaacg cttattacat    1380
tcaggatcgt cttgaggctc agctgggc gcgtcactac cagcagctcg cccgtgaaga     1440
gaaagaggca gaactggcag acgacatgga aaaggcctg ccccagcacc tgtttgaatc     1500
gctatgcatc gatcatttgc aacgccacgg ggccagcaaa aatccatta cccgtgcgtt    1560 tgatgacgat gttgagtttc aggagcgcat ggcagaacac atccggtaca tggttgaaac    1620
cattgctcac caccaggttg atattgattc agaggtataa aacgaatgag tactgcactc    1680

-continued

```
gcaacgctgg ctgggaagct ggctgaacgt gtcggcatgg attctgtcga cccacaggaa    1740
ctgatcacca ctcttcgcca gacggcattt aaaggtgatg ccagcgatgc gcagttcatc    1800
gcattactga tcgttgccaa ccagtacggc cttaatccgt ggacgaaaga aatttacgcc    1860
tttcctgata agcagaatgg catcgttccg gtggtgggcg ttgatggctg gtcccgcatc    1920
atcaatgaaa accagcagtt tgatggcatg gactttgagc aggacaatga atcctgtaca    1980
tgccggattt accgcaagga ccgtaatcat ccgatctgcg ttaccgaatg gatggatgaa    2040
tgccgccgcg aaccattcaa aactcgcgaa ggcagagaaa tcacggggcc gtggcagtcg    2100
catcccaaac ggatgttacg tcataaagcc atgattcagt gtgcccgtct ggccttcgga    2160
tttgctggta tctatgacaa ggatgaagcc gagcgcattg tcgaaaatac tgcatacact    2220
gcagaacgtc agccggaacg cgacatcact ccggttaacg atgaaaccat gcaggagatt    2280
aacactctgc tgatcgccct ggataaaaca tgggatgacg acttattgcc gctctgttcc    2340
cagatatttc gccgcgacat tcgtgcatcg tcagaactga cacaggccga agcagtaaaa    2400
gctcttggat tcctgaaaca gaaagccgca gagcagaagg tggcagcatg acaccggaca    2460
ttatcctgca gcgtaccggg atcgatgtga gagctgtcga acaggggat gatgcgtggc     2520
acaaattacg gctcggcgtc atcaccgctt cagaagttca aacgtgata gcaaaacccc     2580
gctccggaaa gaagtggcct gacatgaaaa tgtcctactt ccacaccctg cttgctgagg    2640
tttgcaccgg tgtggctccg gaagttaacg ctaaagcact ggcctgggga aaacagtacg    2700
agaacgacgc cagaaccctg tttgaattca cttccggcgt gaatgttact gaatccccga    2760
tcatctatcg cgacgaaagt atgcgtaccg cctgctctcc cgatggttta tgcagtgacg    2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga    2940
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaatggac gaggcactgg ctgaaattgg ttttgtattt ggggagcaat     3120
ggcgatgacg catcctcacg ataatatccg ggtaggcgca atcactttcg tctactccgt    3180
tacaaagcga ggctgggtat ttcccggcct ttctgttatc cgaaatccac tgaaagcaca    3240
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc atgggtatgg acagttttcc ctttgatatg    3420
taacggtgaa cagttgttct acttttgttt gttagtcttg atgcttcact gatagataca    3480
agagccataa gaacctcaga tccttccgta tttagccagt atgttctcta gtgtggttcg    3540
ttgttttttgc gtgagccatg agaacgaacc attgagatca tacttacttt gcatgtcact    3600
caaaaatttt gcctcaaaac tggtgagctg aattttttgca gttaaagcat cgtgtagtgt    3660
ttttcttagt ccgttacgta ggtaggaatc tgatgtaatg gttgttggta ttttgtcacc    3720
attcattttt atctggttgt tctcaagttc ggttacgaga tccatttgtc tatctagttc    3780
aacttggaaa atcaacgtat cagtcgggcg gcctcgctta tcaaccacca atttcatatt    3840
gctgtaagtg tttaaatctt tacttattgg tttcaaaacc cattggttaa gcctttttaaa   3900
ctcatggtag ttattttcaa gcattaacat gaacttaaat tcatcaaggc taatctctat    3960
atttgccttg tgagttttct tttgtgttag ttcttttaat aaccactcat aaatcctcat    4020
```

| | |
|---|---|
| agagtatttg ttttcaaaag acttaacatg ttccagatta tattttatga attttttaa | 4080 |
| ctggaaaaga taaggcaata tctcttcact aaaaactaat tctaattttt cgcttgagaa | 4140 |
| cttggcatag tttgtccact ggaaaatctc aaagcccttta accaaaggat tcctgatttc | 4200 |
| cacagttctc gtcatcagct ctctggttgc tttagctaat acaccataag catttttccct | 4260 |
| actgatgttc atcatctgag cgtattggtt ataagtgaac gataccgtcc gttctttcct | 4320 |
| tgtagggttt tcaatcgtgg ggttgagtag tgccacacag cataaaatta gcttggtttc | 4380 |
| atgctccgtt aagtcatagc gactaatcgc tagttcattt gctttgaaaa caactaattc | 4440 |
| agacatacat ctcaattggt ctaggtgatt ttaatcacta taccaattga gatgggctag | 4500 |
| tcaatgataa ttactagtcc ttttcctttg agttgtgggt atctgtaaat tctgctagac | 4560 |
| ctttgctgga aaacttgtaa attctgctag accctctgta aattccgcta gacctttgtg | 4620 |
| tgttttttt gtttatattc aagtggttat aatttataga ataagaaag aataaaaaaa | 4680 |
| gataaaaaga atagatccca gccctgtgta taactcacta ctttagtcag ttccgcagta | 4740 |
| ttacaaaagg atgtcgcaaa cgctgtttgc tcctctacaa aacagaccttt aaaaccctaa | 4800 |
| aggcttaagt agcaccctcg caagctcggt tgcggccgca atcgggcaaa tcgctgaata | 4860 |
| ttcctttttgt ctccgaccat caggcacctg agtcgctgtc tttttcgtga cattcagttc | 4920 |
| gctgcgctca cggctctggc agtgaatggg ggtaaatggc actacaggcg ccttttatgg | 4980 |
| attcatgcaa ggaaactacc cataatacaa gaaaagcccg tcacgggctt ctcagggcgt | 5040 |
| tttatggcgg gtctgctatg tggtgctatc tgacttttg ctgttcagca gttcctgccc | 5100 |
| tctgattttc cagtctgacc acttcggatt atcccgtgac aggtcattca gactggctaa | 5160 |
| tgcacccagt aaggcagcgg tatcatcaac ggggtctgac gctcagtgga acgaaaactc | 5220 |
| acgttaaggg atttttggtca tgagattatc aaaaggatc ttcacctaga tccttttaaa | 5280 |
| ttaaaaatga agttttaaat caatctaaag tatatatgag taaacttggt ctgacagtta | 5340 |
| ccaatgctta atcagtgagg cacctatctc agcgatctgt ctatttcgtt catccatagt | 5400 |
| tgcctgactc cccgtcgtgt agataactac gatacgggag gcttaccat ctggccccag | 5460 |
| tgctgcaatg ataccgcgag acccacgctc accggctcca gatttatcag caataaacca | 5520 |
| gccagccgga agggccgagc gcagaagtgg tcctgcaact ttatccgcct ccatccagtc | 5580 |
| tattaattgt tgccgggaag ctagagtaag tagttcgcca gttaatagtt tgcgcaacgt | 5640 |
| tgttgccatt gctacaggca tcgtggtgtc acgctcgtcg tttggtatgg cttcattcag | 5700 |
| ctccggttcc caacgatcaa ggcgagttac atgatccccc atgttgtgca aaaaagcggt | 5760 |
| tagctccttc ggtcctccga tcgttgtcag aagtaagttg gccgcagtgt tatcactcat | 5820 |
| ggttatggca gcactgcata attctcttac tgtcatgcca tccgtaagat gcttttctgt | 5880 |
| gactggtgag tactcaacca agtcattctg agaatagtgt atgcggcgac cgagttgctc | 5940 |
| ttgcccggcg tcaatacggg ataataccgc gccacatagc agaactttaa aagtgctcat | 6000 |
| cattggaaaa cgttcttcgg ggcgaaaact ctcaaggatc ttaccgctgt tgagatccag | 6060 |
| ttcgatgtaa cccactcgtg cacccaactg atcttcagca tcttttactt tcaccagcgt | 6120 |
| ttctgggtga gcaaaaacag gaaggcaaaa tgccgcaaaa aagggaataa gggcgacacg | 6180 |
| gaaatgttga atactcatac tcttcctttt tcaatattat tgaagcattt atcagggtta | 6240 |
| ttgtctcatg agcggataca tatttgaatg tatttagaaa aataaacaaa tagggggttcc | 6300 |
| gcgcacattt ccccgaaaag tgccacctg | 6329 |

US 7,098,000 B2

METHOD FOR PRODUCTION OF C30-ALDEHYDE CAROTENOIDS

This application claims the benefit of U.S. Provisional Application No. 60/475,743 filed Jun. 4, 2003.

FIELD OF THE INVENTION

This invention is in the field of microbiology. More specifically, this invention describes the production of $C_{30}$-aldehyde carotenoids in genetically transformed microorganisms.

BACKGROUND OF THE INVENTION

Carotenoids represent one of the most widely distributed and structurally diverse classes of natural pigments, producing pigment colors of light yellow to orange to deep red. Eye-catching examples of carotenogenic tissues include carrots, tomatoes, red peppers, and the petals of daffodils and marigolds. All photosynthetic organisms, as well as some bacteria and fungi, synthesize carotenoids. These pigments have important functions in photosynthesis, nutrition, and protection against photooxidative damage. For example, animals do not have the ability to synthesize carotenoids but must instead obtain these nutritionally important compounds through their dietary sources.

Industrially, only a few carotenoids are used for food colors, animal feeds, pharmaceuticals, and cosmetics, despite the existence of more than 600 different carotenoids identified in nature. This is largely due to difficulties in production. Presently, most of the carotenoids used for industrial purposes are produced by chemical synthesis; however, these compounds are very difficult to make chemically (Nelis and Leenheer, *Appl. Bacteriol.* 70:181–191 (1991)). Natural carotenoids can either be obtained by extraction of plant material or by microbial synthesis, but only a few plants are widely used for commercial carotenoid production and the productivity of carotenoid synthesis in these plants is relatively low. As a result, carotenoids produced from these plants are very expensive.

Structurally, the most common carotenoids are 40-carbon ($C_{40}$) terpenoids; however, carotenoids with only 30 carbon atoms ($C_{30}$; diapocarotenoids) are detected in some species. Biosynthesis of carotenoids is derived from the isoprene biosynthetic pathway and its five-carbon universal isoprene building block, isopentenyl pyrophosphate (IPP). This biosynthetic pathway can be divided into two portions: 1) the upper isoprene pathway, which leads to the formation of farnesyl pyrophosphate (FPP); and 2) the lower carotenoid biosynthetic pathway, comprising various crt genes which convert FPP into long $C_{30}$ and $C_{40}$ carotenogenic compounds characterized by a long central chain of conjugated double bonds. Both portions of this pathway are shown in FIG. 1.

The degree of the carbon backbone's unsaturation, conjugation, isomerization and functionalization determines the specific carotenoids' unique absorption characteristics and colors. This variation in properties is the result of a suite of crt genes, such as the crtE, crtX, crtY, crtI, crtB, crtZ, crtW, crtO, crtR, crtM, crtN and cdtN2 genes shown in FIG. 1. Additionally, various other crt genes are known that enable the intramolecular conversion of linear $C_{30}$ and $C_{40}$ compounds to produce numerous other functionalized carotenoid compounds by: (i) hydrogenation, (ii) dehydrogenation, (iii) cyclization, (iv) oxidation, (v) esterification/glycosylation, or any combination of these processes.

The genetics of $C_{40}$ carotenoid pigment biosynthesis has been extremely well studied in the Gram-negative pigmented bacteria of the genera *Pantoea*, formerly known as *Erwinia*. In both *E. herbicola* EHO-10 (ATCC 39368) and *E. uredovora* 20D3 (ATCC 19321), the crt genes are clustered in two genetic units, cdt Z and crt EXYIB (U.S. Pat. No. 5,656,472; U.S. Pat. No. 5,545,816; U.S. Pat. No. 5,530,189; U.S. Pat. No. 5,530,188; and U.S. Pat. No. 5,429,939) These genes have subsequently been sequenced and identified in a suite of other species of bacterial, fungal, plant and animal origin. Several reviews discuss the genetics of carotenoid pigment biosynthesis, such as those of G. Armstrong (*J. Bact.* 176: 4795–4802 (1994); *Annu. Rev. Microbiol.* 51:629–659 (1997)).

The abundant knowledge concerning the genetics of $C_{40}$ biosynthesis has permitted production of a number of natural $C_{40}$ carotenoids from genetically engineered microbial sources. Examples include:

1.) Lycopene (Farmer, W. R. and Liao, J. C., *Biotechnol. Prog.* 17: 57–61(2001); Wang, C. et al., *Biotechnol Prog.* 16: 922–926 (2000); Misawa, N. and Shimada, H., *J. Biotechnol.* 59:169–181 (1998); Shimada, H. et al. *Appl. Environ. Microbiol.* 64:2676–2680 (1998));
2.) β-carotene (Albrecht, M. et al., *Biotechnol. Lett.* 21: 791–795 (1999); Miura, Y. et al., *Appl. Environ. Microbiol.* 64:1226–1229 (1998); U.S. Pat. No. 5,691,190);
3.) Zeaxanthin (Albrecht, M. et al., supra); Miura, Y. et al., supra); and
4.) Astaxanthin (U.S. Pat Nos. 5,466,599; 6,015,684; 5,182,208; and U.S. Pat. No. 5,972,642).

Further, genes encoding various elements of the lower $C_{40}$ carotenoid biosynthetic pathway have been cloned and expressed in various microbes (e.g., U.S. Pat. Nos. 5,656,472; 5,545,816; 5,530,189; 5,530,188; 5,429,939; and U.S. Pat. No. 6,124,113).

Despite abundant knowledge and understanding of the $C_{40}$ carotenoid pathway, $C_{30}$ pigment biosynthesis is both less well-understood and less prevalent in nature. Early studies by Kleinig, H. et al. (*Z. Naturforsch* 34c: 181–185 (1979); *Z. Naturforsch* 37c: 758–760 (1982)) examined the structure and biosynthesis of $C_{30}$ carotenoic acid glucosyl esters produced in *Pseudomonas rhodos* (subsequently renamed *Methylobacterium rhodinum*) by mutational analysis. To date, presence of diapocarotenoids has been discovered in *Streptococcus faecium* (Taylor, R. F. and Davies, B. H., *J. Biochem.* 139:751–760 (1974)), *M. rhodinum* (Kleinig, H. et al., supra; Taylor, R. F. *Microbiol. Rev.* 48:181–198 (1984)), genera of the photosynthetic heliobacteria (Takaichi, S. et al., *Arch. Microbiol.* 168: 277–281 (1997)), and *Staphylococcus aureus* (Marshall, J. H. and Wilmoth, G. J., *J. Bacteriol.* 147:900–913 (1981)). All appear to have a diapophytoene precursor, from which all subsequent $C_{30}$ compounds are produced.

The relevant genes responsible for $C_{30}$ carotenoid pigment biosynthesis are known to include crtM and crtN in *Staphylococcus aureus*. The diapophytoene desaturase CrtN can function to some extent in the $C_{40}$ pathway, and the phytoene desaturase CrtI of the $C_{40}$ carotenoids can also function in the $C_{30}$ pathway (Raisig and Sandmann, *Biochim. Biophys. Acta* 1533:164–170 (2001)). Microbial genomic sequencing effort revealed several ORFs in other organisms with significant homology to crtM or crtN of *S. aureus* (Xiong et al., *Proc. Natl. Acad. Sci. USA* 95:14851–14856 (1998);Takami et al., *Nucleic Acids Res*, 30:3927–3935 (2002)). However, their roles in $C_{30}$ carotenoid synthesis have not been determined. Investigators J.

H. Marshall and G. J. Wilmonth (*J. Bacteriol.* 147:914–919 (1981)) suggested that mixed-function oxidases are responsible for the introduction of oxygen functions to produce the aldehyde and carboxylic acid of 4,4-diaponeurosporene. However, none of the genes responsible for the addition of functionality to the terminal methyl group of the linear $C_{30}$ carotenoid molecule have been identified despite characterization of the resulting carotenoids. Methods for industrial production of $C_{30}$ carotenoids are lacking. It would be desirable to develop methods to produce $C_{30}$ carotenoids (and specifically, $C_{30}$-aldehyde carotenoids such as diaponeurosporene monoaldehyde, diapocarotene monoaldehyde, and diapocarotene dialdehyde (shown in FIG. 2) to increase the number of carotenoids industrially available for use in food colors, animal feeds, pharmaceuticals, and cosmetics. Additionally, the presence of aldehyde group(s) within the $C_{30}$-aldehyde carotenoids also provides active "handles" useful for cross-linking or chemical modification of the carotenoids to facilitate desired applications.

The microbial production of $C_{30}$-aldehyde carotenoids to a significant level has not been previously reported and is especially problematic due to the toxicity of aldehydes to bacterial systems (see, for example: Ingram et al., *Biotechnol. Bioeng.* 65:24–33 (1999); Marnett et al., *Proc. Natl. Acad. Sci. USA* 94:8652–8657 (1997); Mee and O'Donovan, *Mutagenesis* 8:577–581 (1993); Kawazoe et al., *Mutat. Res.* 156:153–161(1985)). In light of these needs, the problem to be solved is to develop a system for production of $C_{30}$-aldehyde carotenoids.

Applicants have solved the stated problem by engineering microorganisms for the production of $C_{30}$-aldehyde carotenoids. Specifically, Applicants have identified two unique open reading frames encoding the enzymes CrtN and CrtN2 from a *Methylomonas* sp. and co-expressed these enzymes with the CrtM and CrtN $C_{30}$-carotenoid biosynthesis enzymes from *Staphylococcus aureus* in *Escherichia coli*. This leads to the production of diapocarotene dialdehyde. Subsequent metabolic engineering of the host demonstrated that synthesis of this $C_{30}$-carotenoid could be modified such that it would be produced in levels suitable for industrial purposes.

SUMMARY OF THE INVENTION

The invention relates to methods of producing $C_{30}$-aldehyde carotenoid compounds via the engineering of a host cell expressing genes encoding a combination of the enzymes diapophytoene synthase, diapophytoene desaturase, and an oxidase for introducing an omega-aldehyde functional group on the omega carbon of a conjugated polyene carbon skeleton.

Accordingly, the invention provides a method for the production of $C_{30}$-aldehyde carotenoid compounds comprising:

a) providing a transformed host cell comprising:
1) suitable levels of farnesyl pyrophosphate;
2) at least one isolated nucleic acid molecule encoding an enzyme having diapophytoene synthase activity under the control of suitable regulatory sequences;
3) at least one isolated nucleic acid molecule encoding an enzyme having diapophytoene desaturase activity under the control of suitable regulatory sequences; and
4) at least one isolated nucleic acid molecule encoding an enzyme having the ability to introduce an omega-aldehyde functional group on the omega carbon of a conjugated polyene carbon skeleton under the control of suitable regulatory sequences;

b) contacting the host cell of step (a) under suitable growth conditions with an effective amount of fermentable carbon substrate whereby a $C_{30}$-aldehyde carotenoid compound is produced.

Preferred diapophytoene synthases for use in the present invention are those having the amino acid sequences as set forth in SEQ ID NO:2 and SEQ ID NO:10. Preferred diapophytoene desaturases for use in the present invention are those having the amino acid sequences as set forth in SEQ ID NO:4 and SEQ ID NO:12. Preferred aldehyde-introducing oxidases for use in the present invention are those having the amino acid sequences as set forth in SEQ ID NO:8 and SEQ ID NO:14.

The invention additionally encompasses methods for the production of $C_{30}$-aldehyde carotenoid compound wherein various elements of the Upper and lower isoprenoid biosynthetic pathway are manipulated to optimize production.

BRIEF DESCRIPTION OF THE DRAWINGS, SEQUENCE DESCRIPTIONS, AND THE BIOLOGICAL DEPOSITS

Figure 3:
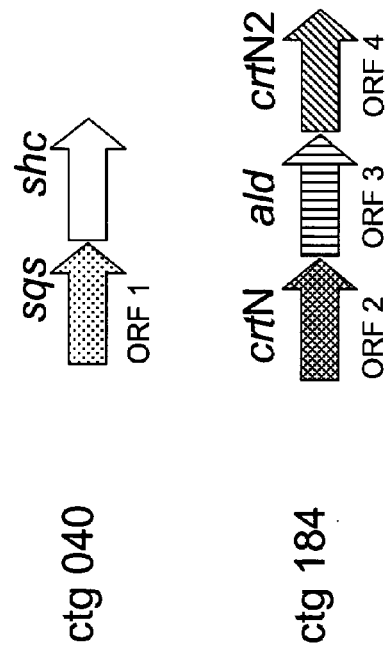
Figure 3:
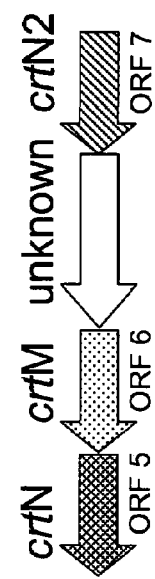

FIGS. 3A and 3B schematically illustrates the organization of the crtN gene clusters in *Methylomonas* sp. 16a and *Staphylococcus aureus* NCTC 8325 (ATCC 35556).

Figure 4:
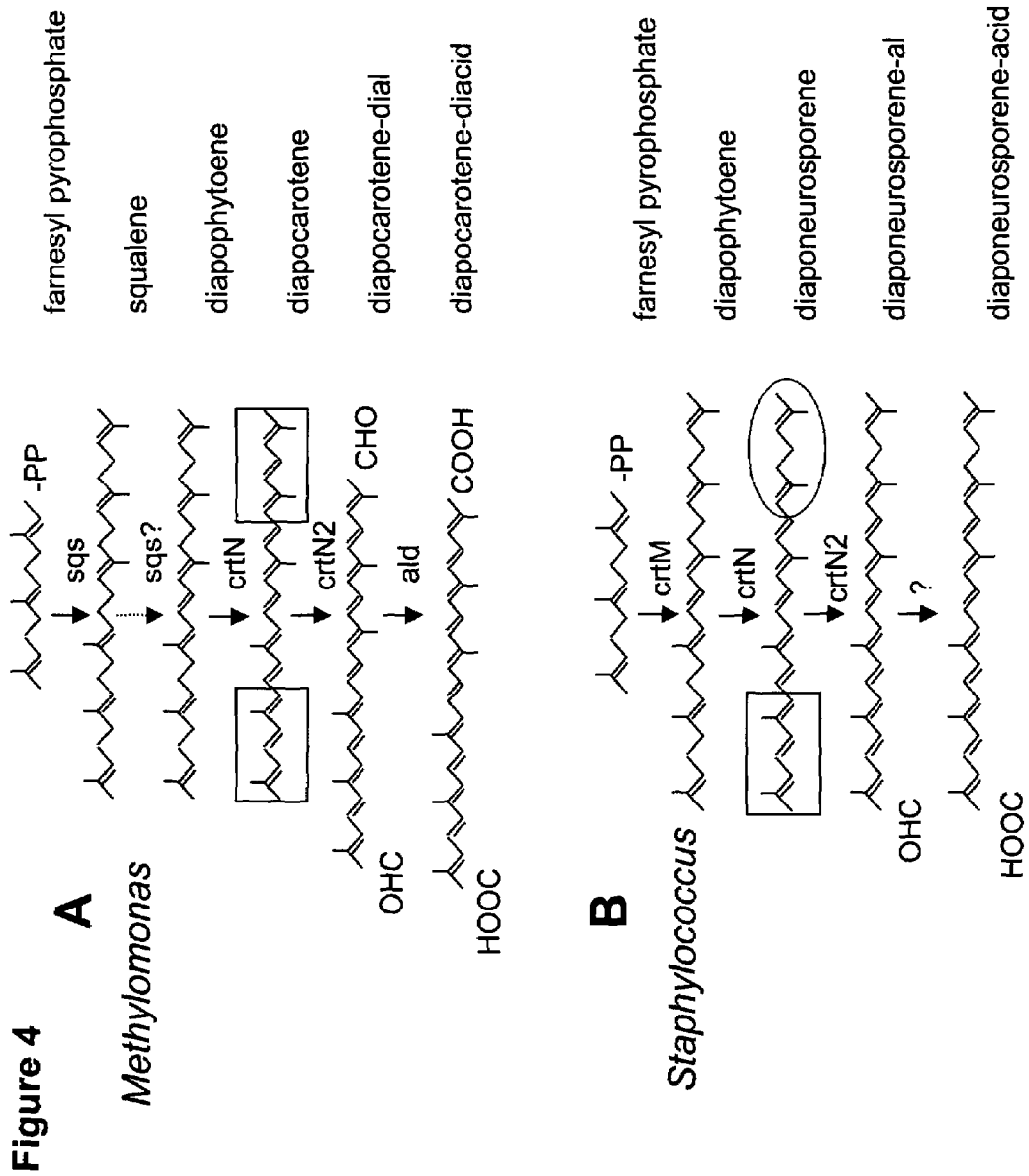

FIG. 4A shows the proposed pathway for $C_{30}$ carotenoid biosynthesis in *Methylomonas* sp. 16a, while FIG. 4B shows the proposed pathway for $C_{30}$ carotenoid biosynthesis in *Staphylococcus aureus*.

Figure 5:
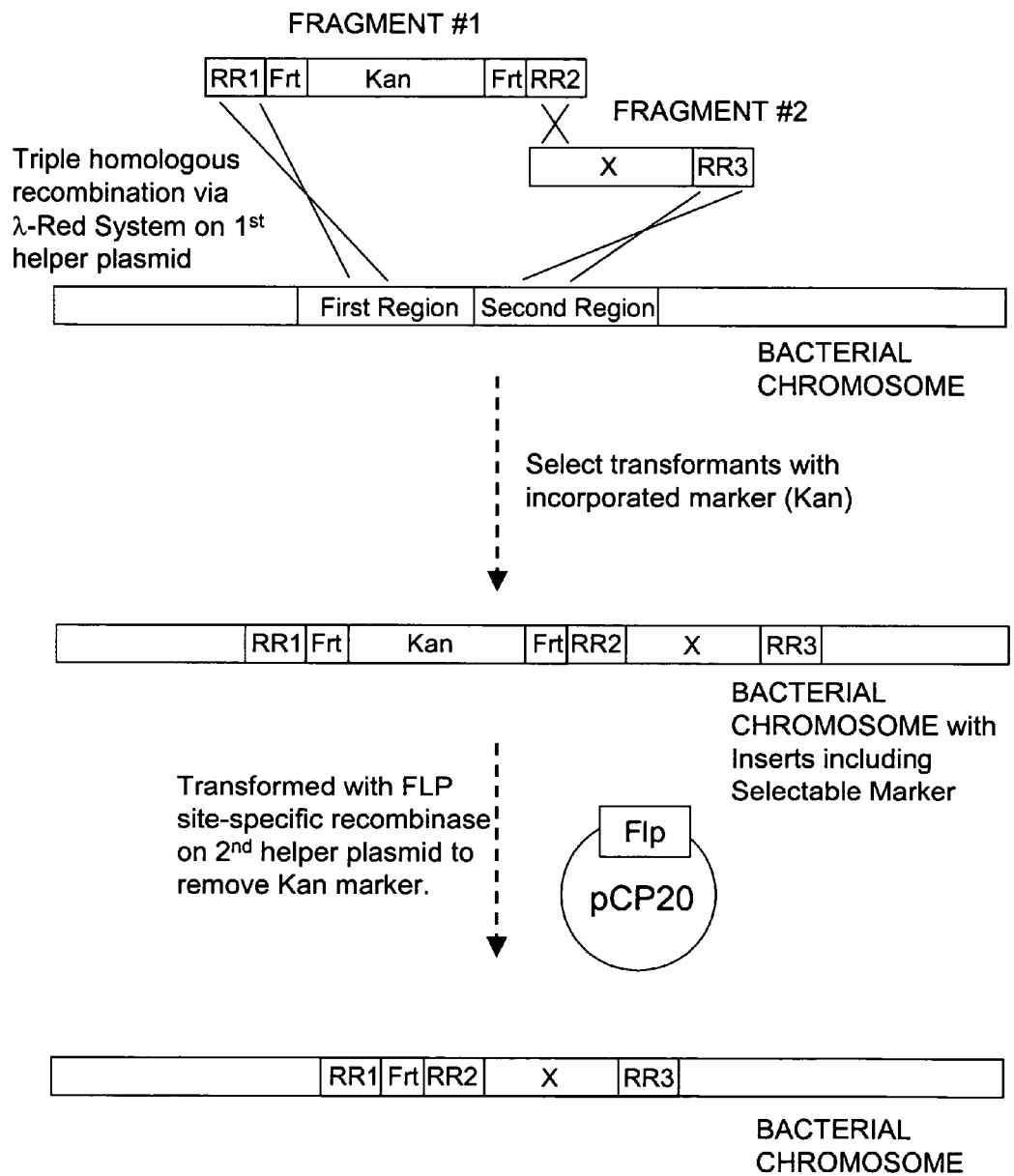

FIG. 5 shows the strategy for chromosomally engineering promoters in *E. coli*, using the two linear PCR fragment method for triple homologous recombination.

Figure 6:
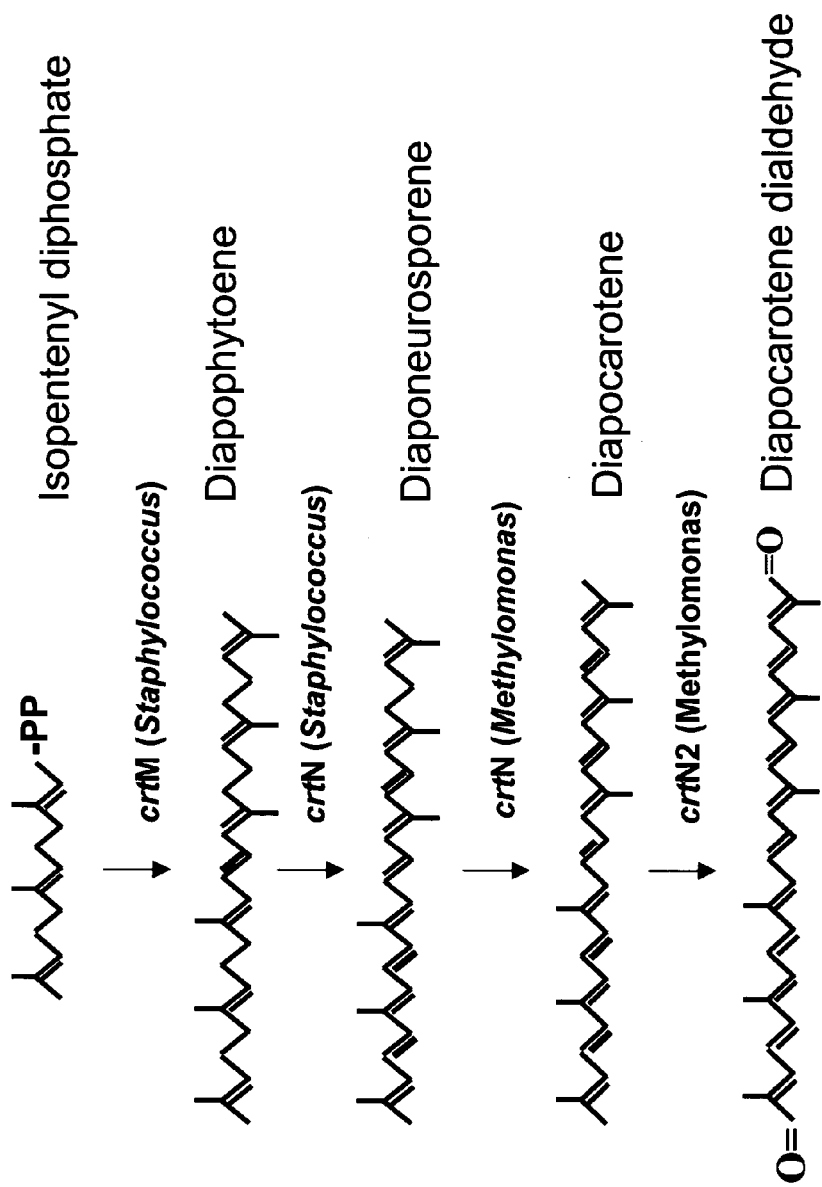

FIG. 6 shows the engineered pathway for $C_{30}$ dialdehyde carotenoid synthesis using a combination of genes derived from both *Staphylococcus* and *Methylomonas*.

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST 0.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs: 1–14 are full-length genes or proteins as identified in the following table.

TABLE 1

Summary of Gene and Protein SEQ ID Numbers

| Description | Organism | SEQ ID NO: Nucleic acid | SEQ ID NO: Peptide |
|---|---|---|---|
| Sqs | *Methylomonas* sp. 16a | 1 | 2 |
| CrtN | *Methylomonas* sp. 16a | 3 | 4 |
| Ald | *Methylomonas* sp. 16a | 5 | 6 |
| CrtN2 | *Methylomonas* sp. 16a | 7 | 8 |

TABLE 1-continued

Summary of Gene and Protein SEQ ID Numbers

| Description | Organism | SEQ ID NO: Nucleic acid | SEQ ID NO: Peptide |
|---|---|---|---|
| CrtM | *Staphylococcus aureus* | 9 | 10 |
| CrtN | *Staphylococcus aureus* | 11 | 12 |
| CrtN2 | *Staphylococcus aureus* | 13 | 14 |

SEQ ID NOs: 15 and 16 are the nucleotide sequences of primers crtM_F/Staphyl and crtM_R/Staphyl used for amplification of crtM from *S. aureus*.

SEQ ID NOs: 17 and 18 are the nucleotide sequences of primers crtN_FL and crtN_RL used for amplification of the crtN-ald-crtN2 gene cluster from *Methylomonas* 16a.

SEQ ID NOs: 19 and 20 are the nucleotide sequences of primers Tet-1 FP and crtN_R used for screening transposon insertions in pDCQ155.

SEQ ID NOs: 21 and 22 are the nucleotide sequences of primers crtM_F/NCTC and crtN_R/NCTC used for amplification of the crtM-crtN gene cluster of *S. aureus*.

SEQ ID NOs: 23 and 24 are the nucleotide sequences of primers crtN__5'/16a and crtN__3'/16a used for amplification of the *Methylomonas* 16a crtN gene.

SEQ ID NOs: 25 and 26 are the nucleotide sequences of primers crtN2_F3/16a and crtN2_R/16a used for amplification of the *Methylomonas* 16a crtN2 gene.

SEQ ID NOs: 27 and 28 are the nucleotide sequences of primers crtN__5'__2/16a and crtN__3'__2/16a used for amplification of the *Methylomonas* 16a crtN gene with a RBS.

SEQ ID NOs: 29 and 30 are the nucleotide sequences encode primers crtN2_5'__2/16a and crtN2_3'__2/16a for amplification of the *Methylomonas* 16a crtN2 gene with a RBS.

SEQ ID NOs: 31–38 are the nucleotide sequences of the primers used for insertion of the T5 promoter upstream from *E. coli* isoprenoid genes via the two-fragment-PCR method for triple homologous recombination.

SEQ ID NOs: 39 is the nucleotide sequence of plasmid pKD46.

Applicants made the following biological deposit under the terms of the Budapest Treaty on the International Recognition of the Deposit of Microorganisms for the Purposes of Patent Procedure:

| Depositor Identification Reference | International Depository Designation | Date of Deposit |
|---|---|---|
| *Methylomonas* 16a | ATCC PTA 2402 | Aug. 22, 2000 |
| Plasmid pCP20 | ATCC PTA 4455 | Jun. 13, 2002 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present method is useful for the creation of recombinant organisms that have the ability to produce $C_{30}$-aldehyde carotenoids. Microbial production of carotenoid compounds are favored, as these compounds are very difficult to make chemically (Nelis and Leenheer, *Appl. Bacteriol.* 70:181–191 (1991) and many of these carotenoids have potent antioxidant properties and are used as dietary supplements.

Nucleic acid fragments encoding the CrtN and CrtN2 enzymes have been isolated from *Methylomonas* 16a. Additionally, a gene homologous to crtN2 has been identified and characterized from *Staphylococcus aureus*. The instant genes, as well as a previously characterized crtM and crtN from *S. aureus*, have been expressed in *Escherichia coli* for high-level production of $C_{30}$-aldehyde carotenoids, in particular a $C_{30}$-dialdehyde identified as diapocarotene dialdehyde.

Definitions

In this disclosure, a number of terms and abbreviations are used. The following definitions are provided.

"Open reading frame" is abbreviated ORF.

"Polymerase chain reaction" is abbreviated PCR.

"Farnesyl pyrophosphate" is abbreviated FPP.

"Ribosomal binding site" is abbreviated RBS.

The term "isoprenoid compound" refers to compounds formally derived from isoprene (2-methylbuta-1,3-diene; $CH_2=C(CH_3)CH=CH_2$), the skeleton of which can generally be discerned in repeated occurrence in the molecule. These compounds are produced biosynthetically via the isoprenoid pathway beginning with isopentenyl pyrophosphate (IPP) and formed by the head-to-tail condensation of isoprene units, leading to molecules which may be—for example—of 5, 10, 15, 20, 30, or 40 carbons in length.

The term "Dxs" refers to the enzyme D-1-deoxyxylulose 5-phosphate encoded by the dxs gene which catalyzes the condensation of pyruvate and D-glyceraldehyde 3-phosphate to D-1-deoxyxylulose 5-phosphate (DOXP).

The terms "Dxr" or "IspC" refer to the enzyme DOXP reductoisomerase encoded by the dxr or ispC gene that catalyzes the simultaneous reduction and isomerization of DOXP to 2-C-methyl-D-erythritol-4-phosphate. The names of the gene, dxr or ispC, are used interchangeably in this application. The names of gene product, Dxr or IspC are used interchangeably in this application.

The term "YgbP" or "IspD" and refers to the enzyme encoded by the ygbB or ispD gene that catalyzes the CTP-dependent cytidylation of 2-C-methyl-D-erythritol-4-phosphate to 4-diphosphocytidyl-2C-methyl-D-erythritol. The names of the gene, ygbP or ispD, are used interchangeably in this application. The names of gene product, YgbP or IspD are used interchangeably in this application.

The term "YchB" or "IspE" and refers to the enzyme encoded by the ychB or ispE gene that catalyzes the ATP-dependent phosphorylation of 4-diphosphocytidyl-2C-methyl-D-erythritol to 4-diphosphocytidyl-2C-methyl-D-erythritol-2-phosphate. The names of the gene, ychB or ispE, are used interchangeably in this application. The names of gene product, YchB or IspE are used interchangeably in this application.

The term "YgbB" or "IspF" refers to the enzyme encoded by the ybgB or ispF gene that catalyzes the cyclization with loss of CMP of 4-diphosphocytidyl-2C-methyl-D-erythritol to 4-diphosphocytidyl-2C-methyl-D-erythritol-2-phosphate to 2C-methyl-D-erythritol-2,4-cyclodiphosphate. The names of the gene, ygbB or ispF, are used interchangeably in this application. The names of gene product, YgbB or IspF are used interchangeably in this application.

The term "GcpE" or "IspG" refers to the enzyme encoded by the gcpE or ispG gene that is involved in conversion of 2C-methyl-D-erythritol-2,4-cyclodiphosphate to 1-hydroxy-2-methyl-2-(E)-butenyl 4-diphosphate. The names of the gene, gcpE or ispG, are used interchangeably in this application. The names of gene product, GcpE or IspG are used interchangeably in this application.

The term "LytB" or "IspH" refers to the enzyme encoded by the lytB or ispH gene and is involved in conversion of 1-hydroxy-2-methyl-2-(E)-butenyl 4-diphosphate to isopentenyl diphosphate (IPP) and dimethylallyl diphosphate (DMAPP). The names of the gene, lytB or ispH, are used interchangeably in this application. The names of gene product, LytB or IspH are used interchangeably in this application.

The term "Idi" refers to the enzyme isopentenyl diphosphate isomerase encoded by the idi gene that converts isopentenyl diphosphate to dimethylallyl diphosphate.

The term "IspA" refers to the enzyme farnesyl pyrophosphate (FPP) synthase encoded by the ispA gene.

The term "IspB" refers to the enzyme octaprenyl diphosphate synthase, which supplies the precursor of the side chain of the isoprenoid quinones encoded by the ispB gene.

The term "PyrG" refers to the enzyme CTP synthase, encoded by the pyrG gene.

The term "crt gene cluster from *Methylomonas* 16a" refers to an open reading frame comprising crtN, ald, and crtN2, that is active in the native carotenoid biosynthetic pathway of *Methylomonas* sp. 16a.

The term "CrtN" refers to the enzyme diapophytoene desaturase (encoded by the crtN gene) responsible for desaturating diapophytoene. "CrtN" is optionally referred to as "CrtN1". The "crtN" gene is optionally referred to as the "crtNI" gene.

The term "pKD46" refers to the plasmid (Datsenko and Wanner, supra) having GenBank® Accession number AY048746. Plasmid pKD46 expresses the components of the λ-Red Recombinase system.

The term "carotenoid biosynthetic pathway" refers to those genes comprising members of the upper isoprenoid pathway and/or lower carotenoid pathway, as defined below.

Figure 1:
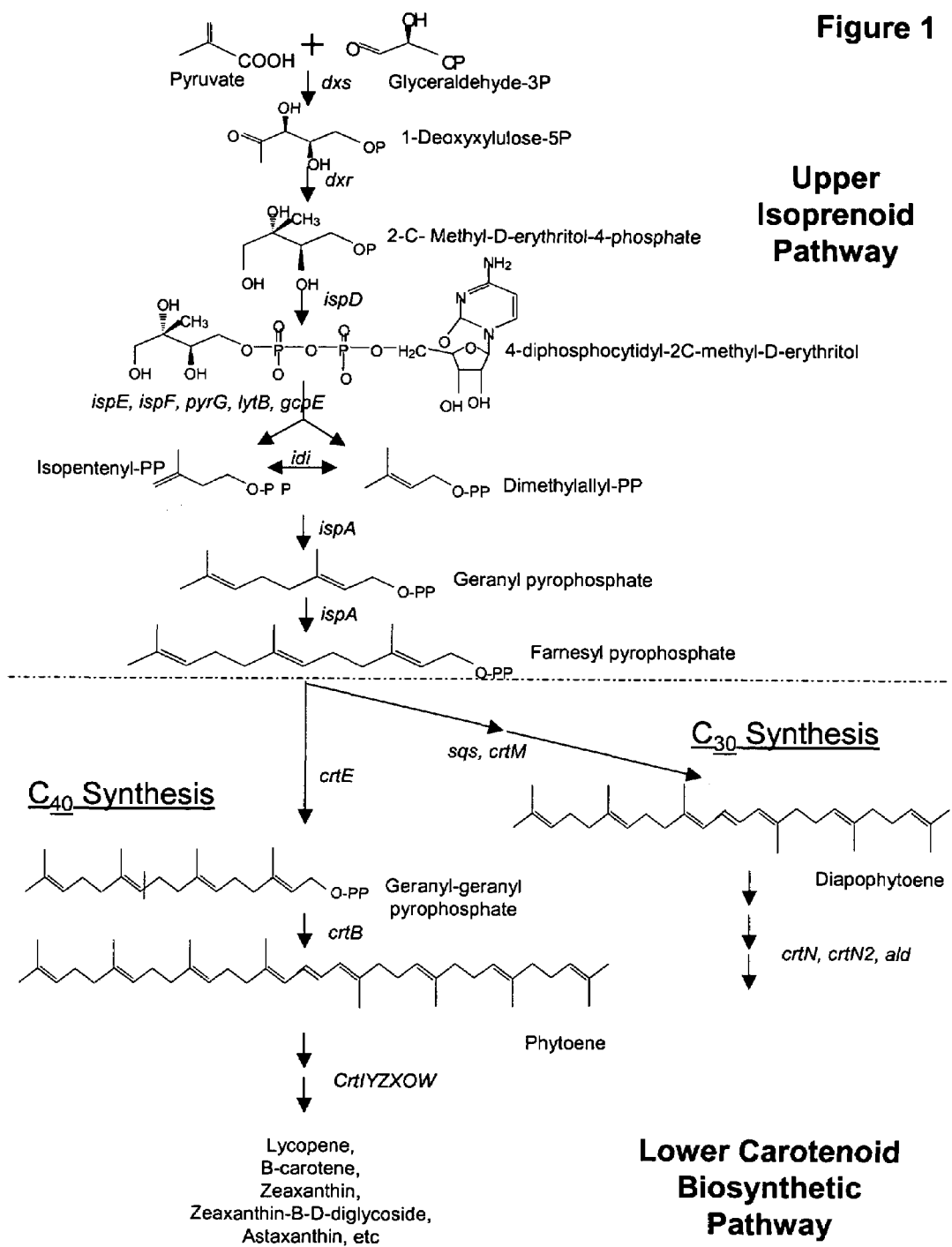
FIG. 1 illustrates the upper isoprene pathway and lower carotenoid pathway.

The terms "upper isoprenoid pathway" and "upper pathway" will be use interchangeably and will refer to the enzymes involved in converting pyruvate and glyceraldehyde-3-phosphate to farnesyl pyrophosphate (FPP). These enzymes include, but are not limited to: the "dxs" gene (encoding 1-deoxyxylulose-5-phosphate synthase); the "dxr" gene (encoding 1-deoxyxylulose-5-phosphate reductoisomerase); the "ispD" gene (encoding a 2C-methyl-D-erythritol cytidyltransferase enzyme; also known as ygbP); the "ispE" gene (encoding 4-diphosphocytidyl-2-C-methyl-erythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "lytB" gene involved in the formation of dimethylallyl diphosphate; the "gcpE" gene involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway (FIG. 1).

The terms "lower carotenoid biosynthetic pathway" and "lower pathway" will be used interchangeably and refer to those enzymes which convert FPP to a suite of carotenoids. These include those genes and gene products that are involved in the immediate synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$–$C_{40}$ carotenoids are included within the lower carotenoid biosynthetic pathway (FIG. 1). These genes and gene products comprise the carotenoid biosynthesis genes including, but not limited to:sqs, ald, crtM, crtN, crtN2, crtE, crtX, crtY, crtI, crtB, crtZ, crtR, crtO, and crtW. Finally, the term "carotenoid biosynthetic enzyme" is an inclusive term referring to any and all of the enzymes in the present pathway including, but not limited to: Ald, Sqs, CrtM, CrtN, CrtN2, CrtE, CrtX, CrtY, CrtI, CrtB, CrtZ, CrtR, CrtW, and CrtO.

For the present application, the term "carotenoid compound" or "carotenoid" is defined as a class of hydrocarbons having a conjugated polyene carbon skeleton formally derived from isoprene, which is composed of triterpenes ($C_{30}$ diapocarotenoids) and tetraterpenes ($C_{40}$ carotenoids) and their oxygenated derivatives. These molecules typically have strong light absorbing properties and may range in length in excess of $C_{200}$. Other "carotenoid compounds" are known which are $C_{35}$, $C_{50}$, $C_{60}$, $C_{70}$ and $C_{80}$ in length, for example. Carotenoids can be produced either synthetically or naturally.

"Tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure (Formula I below), having a long central chain of conjugated double bonds, by (i) hydrogenation, (ii) dehydrogenation, (iii) cyclization, (iv) oxidation, (v) esterification/glycosylation, or any combination of these processes. This class also includes certain compounds that arise from rearrangements of the carbon skeleton (Formula I), or by the (formal) removal of part of this structure.

(I)

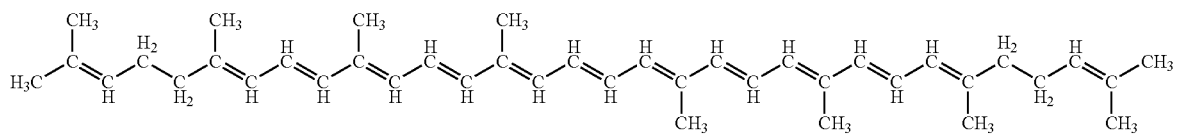

Formula I

For convenience, carotenoid formulae are often written in a shorthand form as shown below in Formula IA:

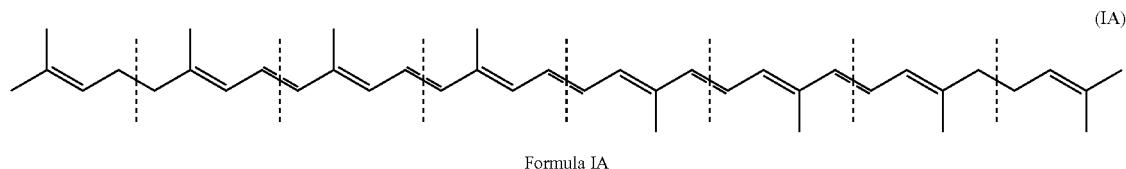

Formula IA where the broken lines indicate formal division into isoprenoid units.

"Triterpenes" or "$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure (Formula II below, hereinafter referred to as "diapophytoene" or "dehydrosqualene"), having a long central chain of conjugated double bonds, by (i) hydrogenation (ii) dehydrogenation, (iii) cyclization, (iv) oxidation, (v) esterification/glycosylation, or any combination of these processes.

The following table defines a suite of genes used within the present application, as well as the names of the enzymes that each gene encodes and a description of the enzyme's biochemical functionality.

TABLE 2

Genes and Enzymes Used in the Present Application

| Gene Name | Enzyme Name | Enzyme Functionality |
|---|---|---|
| sqs | Sqs or Squalene synthase | Converts FPP to squalene; has partial diapophytoene synthase activity |

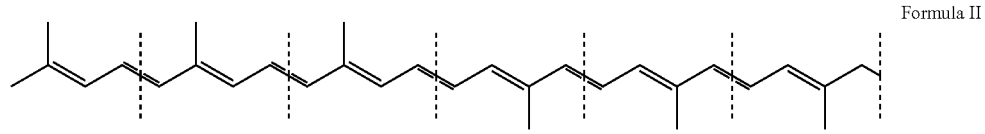

Formula II

The terms "diapolycopene" and "diapocarotene" are used interchangeably to refer to the fully unsaturated $C_{30}$ carotenoid backbone, which may be derived from diapophytoene via dehydrogenation.

Figure 2:
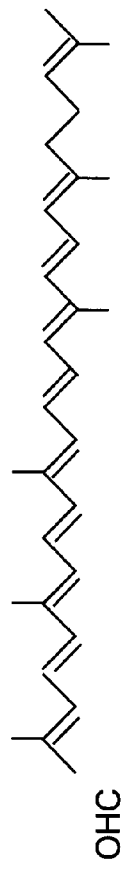
FIG. 2 shows the chemical structures of the $C_{30}$-aldehyde carotenoids: diaponeurosporene monoaldehyde, diapocarotene monoaldehyde, and diapocarotene dialdehyde.
Figure 2:
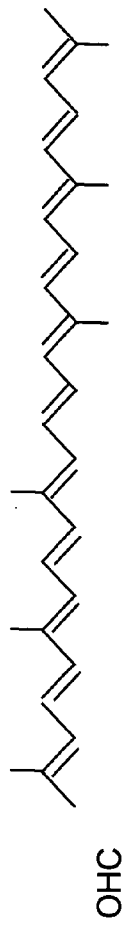
Figure 2:
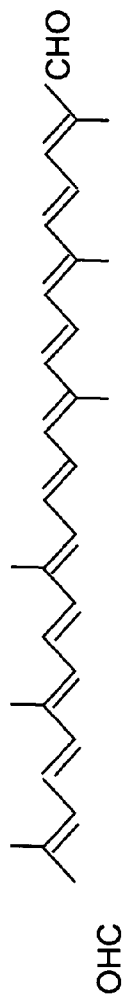

The terms "$C_{30}$ aldehyde" or "$C_{30}$-aldehyde carotenoid" will refer to any carotenoids which contain at least one omega-aldehyde functional group (i,.e., RC(=O)H) on the omega (i.e., end) carbon of the conjugated $C_{30}$ carotenoid backbone. Examples of these types of carotenoids are diaponeurosporene monoaldehyde (or diaponeurosporene-al), diapocarotene monoaldehyde, and diapocarotene dialdehyde (or diapocarotene-dial), as shown in FIG. 2. Additionally, functional derivatives thereof are also included within the present definition of $C_{30}$-aldehyde carotenoids (e.g., β, ψ-diapocarotene-aldehyde).

The term "functionalized" or "functionalization" refers to the (i) hydrogenation, (ii) dehydrogenation, (iii) cyclization, (iv) oxidation, or (v) esterification/glycosylation of any portion of the carotenoid backbone. This backbone is defined as the long central chain of conjugated double bonds. Functionalization may also occur by any combination of the above processes. The specific functionalization discussed in the present application refers to creation of aldehydes (compounds containing RC(=O)H, in which a carbonyl group is bonded to one hydrogen atom and to one R group).

TABLE 2-continued

Genes and Enzymes Used in the Present Application

| Gene Name | Enzyme Name | Enzyme Functionality |
|---|---|---|
| crtM | CrtM or Diapophytoene synthase | Converts FPP to diapophytoene |
| crtN | CrtN, Diapophytoene dehydrogenase, or Diapophytoene desaturase | Introduces additional double bonds to the $C_{30}$ carotenoid precursor diapophytoene |
| crtN2 | CrtN2 or Aldehyde-introducing enzyme | Introduces an omega-aldehyde functional group on the omega carbon(s) of a conjugated polyene carbon skeleton |
| ald | Ald or Aldehyde dehydrogenase | Oxidizes an omega-aldehyde group to an omega-carboxyl functional group on the omega carbon(s) of a conjugated polyene carbon skeleton |

The term "*Methylomonas* 16a" or "*Methylomonas* sp. 16a" is used interchangeably and refers to the *Methylomonas* sp. 16a strain ATCC PTA-2402.

The term "*Staphylococcus aureus*" is used interchangeably with "*S. aureus*" or "*Staphylococcus*" for the purposes of this application and is used to describe *Staphylococcus aureus* strain ATCC 35556.

The term "E. coli" refers to Escherichia coli strain K-12 derivatives, such as MG1655 (ATCC 47076) and MC1061 (ATCC 53338).

The term "triple homologous recombination" or "the two-fragment PCR method" each refers to a genetic recombination between two linear DNA fragments and the target chromosome via their homologous sequences, resulting in chromosomal integration of two linear DNA fragments into the target of chromosome. This method can optionally be used to stack multiple genetic traits into one E. coli host using bacteriophage P1 transduction in combination with a site-specific recombinase system for removal of selection markers (FIG. 5). Use of the two-fragment PCR method for chromosomally engineering changes to carotenoid production in E. coli has previously been reported (U.S. Ser. No. 10/734,936, hereby incorporated by reference). Use of the bacteriophage P1 transduction system for stacking multiple genetic traits in E. coli has also been previously reported (U.S. Ser. No. 10/734,778 and U.S. Ser. No. 10/735,442).

The terms "P1 donor cell" and "donor cell" are used interchangeably in the present invention and refer to a bacterial strain susceptible to infection by a bacteriophage or virus, and which serves as a source for the nucleic acid fragments packaged into the transducing particles. Typically the genetic make up of the donor cell is similar or identical to the "recipient cell" which serves to receive P1 lysate containing transducing phage or virus produced by the donor cell.

The terms "P1 recipient cell" and "recipient cell" are used interchangeably in the present invention and refer to a bacterial strain susceptible to infection by a bacteriophage or virus and which serves to receive lysate containing transducing phage or virus produced by the donor cell.

The term "homology arm" refers to a nucleotide sequence which enables homologous recombination between two nucleic acids having substantially the same nucleotide sequence in a particular region of two different nucleic acids. The preferred size range of the nucleotide sequence of the homology arm is from about 10 to about 50 nucleotides.

The terms "stacking", "combinatorial stacking", "chromosomal stacking", and "trait stacking" are used interchangeably and refer to the repeated process of stacking multiple genetic traits into one E. coli host using the bacteriophage P1 in combination with the site-specific recombinase system for removal of selection markers.

The term "fermentable carbon substrate" refers to a carbon source capable of being metabolized by host organisms of the present invention and particularly carbon sources selected from the group consisting of monosaccharides, disaccharides, polysaccharides, one-carbon substrates (methane, methanol, formate and the like), and/or mixtures thereof.

The term "recombinase" refers to one or more enzymes, which either work alone or in combination to stimulate homologous recombination. The "λ-Red recombinase", "λ-Red recombination system", and "λ-Red system" are used interchangeably to describe a group of enzymes encoded by the bacteriophage λ genes exo, bet, and gam. The enzymes encoded by the three genes work together to increase the rate of homologous recombination in E. coli, an organism generally considered to have a relatively low rate of homologous recombination, especially when using linear recombination elements (Datsenko and Wanner, Proc. Natl. Acad. Sci. USA 97:6640–6645 (2000)).

The terms "site-specific recombinase system" and "site-specific recombinase" and "recombinase" are used interchangeably in the present invention to describe a system comprised of one or more enzymes which recognize specific nucleotide sequences (recombination target sites) and which catalyze recombination between the recombination target sites. Site-specific recombination provides a method to rearrange, delete, or introduce exogenous DNA. Examples of site-specific recombinases and their associated recombination target sites are flippase (FLP/FRT), Cre-lox, R/RS, Gin/gix, Xer/dif, and Int/att. In the present invention the Applicants illustrate the use of a site-specific recombinase to remove selectable markers. Antibiotic resistance markers, flanked on both sides by FRT recombination target sites, are removed by expression of the FLP site-specific recombinase. This method is used so that the numbers of chromosomal modifications necessary for microbial pathway engineering is not limited to the number of available selection markers (Huang et al., J. Bacteriol., 179(19): 6076–6083. (1997)).

The term "homology" as applied to recombination regions and corresponding regions on a bacterial chromosome means nucleotide sequences sharing identical or nearly identical sequences. Complementary sequences between regions on the bacterial chromosome and recombination regions can associate and undergo homologous recombination in the presence of a recombinase system. Preferred recombination regions, or "homology arms", are those having identical sequences to the corresponding regions on the bacterial chromosome and that are from about 10–50 bp in length.

The terms "$P_{T5}$ promoter", "$P_{T5}$", and "T5 promoter" refer to the nucleotide sequence that comprises the −10 and −35 consensus sequences from phage T5, lactose operator (lacO), and ribosomal binding site (RBS) from E. coli.

The term "helper plasmid" refers to either pKD46 encoding the λ-Red recombinase system or pCP20 encoding the FLP site-specific recombinase (Datsenko and Wanner, supra).

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2$^{nd}$ ed., Cold Spring Harbor Laboratory: Cold Spring Harbor, N.Y. (1989), particularly Chapter 11 and Table 11.1 therein (hereinafter "Maniatis"). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C.

Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Maniatis, supra, 9.50–9.51). For hybridizations with shorter nucleic acids (i.e., oligonucleotides), the position of mismatches becomes more important and the length of the oligonucleotide determines its specificity (see Maniatis, supra, 11.7–11.8). In one embodiment, the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences, as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., ed.) Oxford University: NY (1988); 2.) *Biocomputing: Informatics and Genome Projects* (Smith, D. W., ed.) Academic: NY (1993); 3.) *Computer Analysis of Sequence Data, Part I* (Griffin, A. M., and Griffin, H. G., eds.) Humania: NJ (1994); 4.) *Sequence Analysis in Molecular Biology* (von Heinje, G., ed.) Academic (1987); and 5.) *Sequence Analysis Primer* (Gribskov, M. and Devereux, J., eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp, CABIOS 5:151–153 (1989)) with default parameters (GAP PENALTY=10, GAP LENGTH PENALTY=10). Default parameters for pairwise alignments using the Clustal method were: KTUPLE=1, GAP PENALTY=3, WINDOW=5 and DIAGONALS SAVED=5.

Suitable nucleic acid fragments (isolated polynucleotides of the present invention) encode polypeptides that are at least about 70% identical, and preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the present invention relates to any nucleic acid fragment that encodes all or a substantial portion of the amino acid sequence encoding the instant microbial polypeptides as set forth in SEQ ID NOs: 2, 4, 8, 10, 12 and 14. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to and derived from mRNA. "Sense" RNA refers to an RNA transcript that includes the mRNA and so can be translated into protein by the cell. "Antisense RNA" refers to an RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic", "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequences into a cell. "Transformation cassette" refers to a specific vector containing a foreign gene and having elements in addition to the foreign gene(s) that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); 4.) the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Plenum: New York, N.Y.); and 5.) the Vector NTI programs version 7.0 (Informax, Inc., Bethesda, Md.). Within the context of this application it will be understood that where sequence analysis software is used for analysis, the results of the analysis will be based on the "default values" of the program referenced, unless otherwise specified. As used herein "default values" will mean any set of values or parameters (set by the software manufacturer) which originally load with the software when first initialized.

Standard recombinant DNA and molecular cloning techniques used herein are well known in the art and are described by Maniatis (supra); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Genes Involved in Carotenoid Production

The enzyme pathway involved in the biosynthesis of carotenoid compounds can be conveniently viewed in two parts, the upper isoprenoid pathway (providing for the conversion of pyruvate and glyceraldehyde-3-phosphate to farnesyl pyrophosphate) and the lower carotenoid biosynthetic pathway (which provides for the synthesis of either diapophytoene or phytoene and all subsequently produced carotenoids) (FIG. 1). The upper pathway is ubiquitous in many microorganisms and in these cases it will only be necessary to introduce genes that comprise the lower pathway for biosynthesis of the desired carotenoid. The division between the two pathways concerns the synthesis of farnesyl pyrophosphate (FPP). Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. Where FPP synthesis is not provided by the host cell, it will be necessary to introduce the genes necessary for the production of FPP. Where FPP is synthesized at an unsuitable level in the host cell, it will be necessary to engineer modifications to genes involved in isoprenoid production. Examples of the genetic modifications include, but are not limited to, up-regulating expression of isoprenoid genes and/or down-regulating genes that divert carbon flow away from FPP synthesis. Each of these pathways will be discussed below in detail.

The Upper Isoprenoid Pathway

Isoprenoid biosynthesis occurs through either of two pathways, generating the common $C_5$ isoprene subunit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.* 111:135–140 (1993); Rohmer et al., *Biochem.* 295: 517–524 (1993); Schwender et al., *Biochem.* 316: 73–80 (1996); and Eisenreich et al., *Proc. Natl. Acad. Sci. USA* 93: 6431–6436 (1996)).

Many steps in the mevalonate-independent isoprenoid pathway are known. For example, the initial steps of the alternate pathway leading to the production of IPP have been studied in *Mycobacterium tuberculosis* by Cole et al. (*Nature* 393:537–544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol4-phosphate. One of the enzymes involved in the isomerization and reduction process is D-1-deoxyxylulose-5-phosphate reductoisomerase (DXR), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP (Cole et al., supra). Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). Finally, the product of the ygbB gene converts 4-diphosphocytidyl-2C-methyl-D-erythritol 2-phosphate to 2C-methyl-D-erythritol 2,4-cyclodiphosphate in a CTP-dependent manner. This gene has also been recently renamed, and belongs to the isp gene cluster. Specifically, the new name for the ygbB gene is ispF (SwissProtein Accession #P36663). The product of the pyrG gene is important in these reactions, as a CTP synthase.

The enzymes encoded by the lytB and gcpE genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene; however, this enzyme is not essential for survival and may be absent in some bacteria using the 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate (DMAPP). This reaction is followed by a sequence of two prenyltransferase reactions catalyzed by IspA, leading to the creation of geranyl pyrophosphate (GPP; a 10-carbon molecule) and farnesyl pyrophosphate (FPP; a 15-carbon molecule).

Genes encoding elements of the upper pathway are known from a variety of plant, animal, and bacterial sources, as shown in Table 3.

TABLE 3

Sources of Genes Encoding the Upper Isoprene Pathway

| Gene | GenBank Accession Number and Source Organism |
|---|---|
| dxs (D-1-deoxyxylulose 5-phosphate synthase) | AF035440, *Escherichia coli*<br>Y18874, *Synechococcus* PCC6301<br>AB026631, *Streptomyces* sp. CL190<br>AB042821, *Streptomyces griseolosporeus*<br>AF111814, *Plasmodium falciparum*<br>AF143812, *Lycopersicon esculentum*<br>AJ279019, *Narcissus pseudonarcissus*<br>AJ291721, *Nicotiana tabacum* |
| dxr (ispC) (1-deoxy-D-xylulose 5-phosphate reductoisomerase) | AB013300, *Escherichia coli*<br>AB049187, *Streptomyces griseolosporeus*<br>AF111813, *Plasmodium falciparum*<br>AF116825, *Mentha x piperita*<br>AF148852, *Arabidopsis thaliana*<br>AF182287, *Artemisia annua*<br>AF250235, *Catharanthus roseus*<br>AF282879, *Pseudomonas aeruginosa*<br>AJ242588, *Arabidopsis thaliana*<br>AJ250714, *Zymomonas mobilis* strain ZM4<br>AJ292312, *Klebsiella pneumoniae*,<br>AJ297566, *Zea mays* |
| ygbP (ispD) (2-C-methyl-D-erythritol 4-phosphate cytidylyltransferase) | AB037876, *Arabidopsis thaliana*<br>AF109075, *Clostridium difficile*<br>AF230736, *Escherichia coli*<br>AF230737, *Arabidopsis thaliana* |
| ychB (ispE) (4-diphosphocytidyl-2-C-methyl-D-erythritol kinase) | AF216300, *Escherichia coli*<br>AF263101, *Lycopersicon esculentum*<br>AF288615, *Arabidopsis thaliana* |
| ygbB (ispF) (2-C-methyl-D-erythritol 2,4-cyclodiphosphate synthase) | AB038256, *Escherichia coli* mecs gene<br>AF230738, *Escherichia coli*<br>AF250236, *Catharanthus roseus* (MECS)<br>AF279661, *Plasmodium falciparum*<br>AF321531, *Arabidopsis thaliana* |
| gcpE (ispG) (1-hydroxy-2-methyl-2-(E)-butenyl 4-diphosphate synthase) | O67496, *Aquifex aeolicus*<br>P54482, *Bacillus subtilis*<br>Q9pky3, *Chlamydia muridarum*<br>Q9Z8H0, *Chlamydophila pneumoniae*<br>O84060, *Chlamydia trachomatis*<br>P27433, *Escherichia coli*<br>P44667, *Haemophilus influenzae*<br>Q9ZLL0, *Helicobacter pylori* J99<br>O33350, *Mycobacterium tuberculosis*<br>S77159, *Synechocystis* sp.<br>Q9WZZ3, *Thermotoga maritima*<br>O83460, *Treponema pallidum*<br>Q9JZ40, *Neisseria meningitidis*<br>Q9PPM1, *Campylobacter jejuni*<br>Q9RXC9, *Deinococcus radiodurans*<br>AAG07190, *Pseudomonas aeruginosa*<br>Q9KTX1, *Vibrio cholerae* |
| lytB (ispH) | AF027189, *Acinetobacter* sp. BD413<br>AF098521, *Burkholderia pseudomallei*<br>AF291696, *Streptococcus pneumoniae*<br>AF323927, *Plasmodium falciparum* gene<br>M87645, *Bacillus subtillis*<br>U38915, *Synechocystis* sp.<br>X89371, *C. jejunisp* O67496 |
| IspA (FPP synthase) | AB003187, *Micrococcus luteus*<br>AB016094, *Synechococcus elongatus*<br>AB021747, *Oryza sativa* FPPS1 gene for farnesyl diphosphate synthase<br>AB028044, *Rhodobacter sphaeroides*<br>AB028046, *Rhodobacter capsulatus*<br>AB028047, *Rhodovulum sulfidophilum*<br>AF112881 and AF136602, *Artemisia annua*<br>AF384040, *Mentha x piperita*<br>D00694, *Escherichia coli*<br>D13293, *B. stearothermophilus*<br>D85317, *Oryza sativa*<br>X75789, *A. thaliana*<br>Y12072, *G. arboreum*<br>Z49786, *H. brasiliensis*<br>U80605, *Arabidopsis thaliana* farnesyl diphosphate |

TABLE 3-continued

Sources of Genes Encoding the Upper Isoprene Pathway

| Gene | GenBank Accession Number and Source Organism |
|---|---|
| | synthase precursor (FPS1) mRNA, complete cds |
| | X76026, *K. lactis* FPS gene for farnesyl diphosphate synthetase, QCR8 gene for bc1 complex, subunit VIII |
| | X82542, *P. argentatum* mRNA for farnesyl diphosphate synthase (FPS1) |
| | X82543, *P. argentatum* mRNA for farnesyl diphosphate synthase (FPS2) |
| | BC010004, *Homo sapiens*, farnesyl diphosphate synthase (farnesyl pyrophosphate synthetase, dimethylallyltranstransferase, geranyltranstransferase), clone MGC 15352 IMAGE, 4132071, mRNA, complete cds |
| | AF234168, *Dictyostelium discoideum* farnesyl diphosphate synthase (Dfps) |
| | L46349, *Arabidopsis thaliana* farnesyl diphosphate synthase (FPS2) mRNA, complete cds |
| | L46350, *Arabidopsis thaliana* farnesyl diphosphate synthase (FPS2) gene, complete cds |
| | L46367, *Arabidopsis thaliana* farnesyl diphosphate synthase (FPS1) gene, alternative products, complete cds |
| | M89945, Rat farnesyl diphosphate synthase gene, exons 1–8 |
| | NM_002004, *Homo sapiens* farnesyl diphosphate synthase (farnesyl pyrophosphate synthetase, dimethylallyltranstransferase, geranyltranstransferase) (FDPS), mRNA |
| | U36376, *Artemisia annua* farnesyl diphosphate synthase (fps1) mRNA, complete cds |
| | XM_001352, *Homo sapiens* farnesyl diphosphate synthase (farnesyl pyrophosphate synthetase, dimethylallyltranstransferase, geranyltranstransferase) (FDPS), mRNA |
| | XM_034497, *Homo sapiens* farnesyl diphosphate synthase (farnesyl pyrophosphate synthetase, dimethylallyltranstransferase, geranyltranstransferase) (FDPS), mRNA |
| | XM_034498, *Homo sapiens* farnesyl diphosphate synthase (farnesyl pyrophosphate synthetase, dimethylallyltranstransferase, geranyltranstransferase) (FDPS), mRNA |
| | XM_034499, *Homo sapiens* farnesyl diphosphate synthase (farnesyl pyrophosphate synthetase, dimethylallyltranstransferase, geranyltranstransferase) (FDPS), mRNA |
| | XM_0345002, *Homo sapiens* farnesyl diphosphate synthase (farnesyl pyrophosphate synthetase, dimethylallyltranstransferase, geranyltranstransferase) (FDPS), mRNA |

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the Applicants consider the first step in the lower carotenoid biosynthetic pathway to begin with the conversion of farnesyl pyrophosphate (FPP) to compounds that lead to the formation of either $C_{30}$ diapocarotenoids or $C_{40}$ carotenoids (FIG. 1).

The $C_{40}$ Lower Carotenoid Biosynthetic Pathway

Within the $C_{40}$ pathway, the first step in the biosynthetic pathway begins with the prenyltransferase reaction converting FPP to geranylgeranyl pyrophosphate (GGPP). The gene crtE, encoding GGPP synthetase, is responsible for this prenyltransferase reaction, leading to the synthesis of phytoene. This reaction adds IPP to FPP to produce a 20-carbon molecule, geranylgeranyl pyrophosphate (GGPP).

Finally, a condensation reaction of two molecules of GGPP occurs to form phytoene (PPPP), the first 40-carbon molecule of the lower carotenoid biosynthesis pathway. This reaction is catalyzed by phytoene synthase (encoded by the gene crtB).

From the compound phytoene, a spectrum of $C_{40}$ carotenoids is produced by subsequent hydrogenation, dehydrogenation, cyclization, oxidation, or any combination of these processes. For example, lycopene, which imparts a "red"-colored spectra, is produced from phytoene through four sequential dehydrogenation reactions by the removal of eight atoms of hydrogen, catalyzed by the gene crtI (encoding phytoene desaturase). Lycopene cyclase (crtY) converts lycopene to β-carotene. β-carotene is converted to zeaxanthin via a hydroxylation reaction resulting from the activity of β-carotene hydroxylase (encoded by the crtZ gene). These examples are not limiting and many other carotenoid genes and products (e.g., crtX, crtW/O) exist within this $C_{40}$ lower carotenoid biosynthetic pathway.

The $C_{30}$ Lower Carotenoid Biosynthetic Pathway

Within the $C_{30}$ pathway, the first unique step in the biosynthetic pathway begins with the conversion of FPP to diapophytoene.

This pathway is well-studied in *Staphylococcus aureus*. The first committed reaction is the head-to-head condensation of two molecules of farnesyl diphosphate ($C_{15}$) by CrtM, forming dehydrosqualene (Wieland, B. et al., *J. Bacteriol*. 176(24): 7719–7726 (1994)). Subsequently, dehydrosqualene desaturase (CrtN) is successively dehydrogenated in three steps to produce 4,4'-diaponeurosporene (Wieland et al., supra). However, at present time public databases include only one single gene (GenBank® Accession Number X73889) and 4 genomic sequences (NC002745, NC002758, AP003137, and AP003365) of crtN and crtM, isolated from *S. aureus* strains N315 and Mu5O. A single report exists concerning the heterologous overexpression of crtN from *S. aureus* in *E. coli* (Raisig, A., and Sandmann, G., *J. Bacteriol.*, 181(19):6184–6187 (1999)). Based on the identification of the carotenoid compounds produced, it is known that the next stages in the $C_{30}$ metabolic pathway for *S. aureus* involve introduction of oxygen functions on the terminal methyl group to produce aldehyde and carboxylic acid forms of the carotenoid (Marshall, J. H., and Wilmoth, G. J., *J. Bacteriol*. 147: 900–913 (1981) and 147: 914–919 (1981)). We have recently identified genes (crtN2)which perform this function (U.S. Ser. No. 10/358,917 and corresponding WO 03/068917). *Methylomonas* 16a is a pink-pigmented methanotrophic prokaryote capable of utilizing methane as its sole carbon substrate (described in WO 02/20728 and WO 02/18617). Identification of genes crtN,crtN2 and ald contributed to the detailed understanding of the carotenoid synthesis pathway of conversion of FPP to a naturally-occurring $C_{30}$ pigment produced by the organism.

Sequence Identification of Novel Genes from the $C_{30}$ Lower Carotenoid Biosynthetic Pathway.

A variety of nucleotide sequences have been isolated from *Methylomonas* 16a encoding gene products involved in the native $C_{30}$ lower carotenoid pathway (U.S. Ser. No. 10/358917). ORF's 1–4, for example, encode enzymes in the lower carotenoid biosynthetic pathway (see FIGS. 3A and 4A). Specifically:

Comparison of the sqs nucleotide base and deduced amino acid sequences (ORF 1) to public databases reveals that the most similar known sequences range from about 60% identical to the amino acid sequence of Sqs reported herein over a length of 363 amino acids using a Smith-Waterman alignment algorithm (W. R. Pearson, supra).

Comparison of the crtN nucleotide base and deduced amino acid sequences (ORF 2) to public databases reveals that the most similar known sequences range from about 34% identical to the amino acid sequence of CrtN reported herein over a length of 511 amino acids using a Smith-Waterman alignment algorithm (W. R. Pearson, supra).

Comparison of the ald nucleotide base and deduced amino acid sequences (ORF 3) to public databases reveals that the most similar known sequences range from about 33% identical to the amino acid sequence of Aid reported herein over a length of 530 amino acids using a Smith-Waterman alignment algorithm (W. R. Pearson, supra).

Comparison of the crtN2 nucleotide base and deduced amino acid sequences (ORF 4) to public databases reveals that the most similar known sequences range from about 51% identical to the amino acid sequence of CrtN2 reported herein over a length of 497 amino acids using a Smith-Waterman alignment algorithm (W. R. Pearson, supra).

For each of the enzymes described above (i.e., Sqs, CrtN, Ald, and CrtN2), more preferred amino acid fragments are at least about 70%–80% identical to the sequences herein, where about 80%–90% is preferred. Most preferred are nucleic acid fragments that are at least 95% identical to the amino acid fragments reported herein.

Similarly, preferred nucleic acid sequences corresponding to the instant ORF's are those encoding active proteins and which are at least 80% identical to the nucleic acid sequences reported herein. More preferred sqs, citN, ald, and crtN2 nucleic acid fragments are at least 90% identical to the sequences herein. Most preferred are nucleic acid fragments that are at least 95% identical to the nucleic acid fragments reported herein.

In addition to the nucleotide sequences isolated from *Methylomonas* 16a, a hypothetical protein in *Staphylococcus aureus* (ATCC 35556) was determined to encode a crtN2 gene. Comparison of the nucleotide base and deduced amino acid sequences (ORF 7; FIG. 3B) to public databases reveals that the most similar known sequences range from about 55% identical to the amino acid sequence of CrtN2 reported herein over a length of 497 amino acids using a Smith-Waterman alignment algorithm (W. R. Pearson, supra). Additionally, this gene has 51% identity and 68% similarity to the CrtN2 of 16a. More preferred amino acid fragments are at least about 70%–80% identical to the sequences herein, where about 80%–90% is preferred. Most preferred are nucleic acid fragments that are at least 95% identical to the amino acid fragments reported herein. Similarly, preferred crtN2 encoding nucleic acid sequences corresponding to the instant ORF are those encoding active proteins and which are at least 80% identical to the nucleic acid sequences of reported herein. More preferred crtN2 nucleic acid fragments are at least 90% identical to the sequences herein. Most preferred are crtN2 nucleic acid fragments that are at least 95% identical to the nucleic acid fragments reported herein.

Isolation of $C_{30}$ Lower Carotenoid Biosynthetic Pathway Homologs

Each of the nucleic acid fragments of the $C_{30}$ lower carotenoid biosynthetic pathway (crtM, sqs, crtN, aid and crtN2) may be used to isolate genes encoding homologous proteins from the same or other microbial (or plant) species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies (e.g., polymerase chain reaction (PCR), Mullis et al., U.S. Pat. No. 4,683,202; ligase chain reaction (LCR), Tabor, S. et al., *Proc. Natl. Acad. Sci. USA* 82:1074 (1985); or strand displacement amplification (SDA), Walker et al., *Proc. Natl. Acad. Sci. USA*, 89: 392 (1992)); and 3.) methods of library construction and screening by complementation.

For example, genes encoding similar proteins or polypeptides to those of the $C_{30}$ lower carotenoid biosynthetic pathway, as described herein, could be isolated directly by using all or a portion of the instant nucleic acid fragments as DNA hybridization probes to screen libraries from any desired bacteria using methodology well known to those skilled in the art (wherein those bacteria producing $C_{30}$ carotenoids would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation, or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33–50 IRL: Herndon, V A; and Rychlik, W., *In Methods in Molecular Biology*, White, B. A. (Ed.), (1993) Vol.15, pp 31–39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *Proc. Natl. Acad. Sci. USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL, Gaithersburg, Md.), specific 3' or 5' cDNA fragments can be isolated (Ohara et al., *Proc. Natl. Acad. Sci. USA* 86:5673 (1989); Loh et al., *Science* 243:217 (1989)).

Alternatively, the instant sequences of the $C_{30}$ lower carotenoid biosynthetic pathway may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers (e.g., sodium citrate, Tris-HCl, PIPES or HEPES (pH range about 6–9)), about 0.05 to 0.2% detergent (e.g., sodium dodecylsulfate), or between 0.5–20 mM EDTA, FICOLL (Pharmacia Inc.) (about 300–500 kdal), polyvinylpyrrolidone (about 250–500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis, supra).

Enzyme Functionality Of $C_{30}$ Lower Carotenoid Biosynthetic Genes

The hypothesized pathway for $C_{30}$ carboxy-carotenoid synthesis in *Methylomonas* 16a and *Staphylococcus aureus* can be compared in FIGS. 4A and 4B. Both pathways require FPP as a precursor molecule; however, different genes are responsible for the formation of diapophytoene. Experimental studies (U.S. Ser. No. 10/358,917) confirmed that FPP is directly converted to diapophytoene in *S. aureus* (FIG. 4B), a reaction catalyzed by the well-known crtM gene encoding dehydrosqualene synthase (Wieland et al., *J. Bacteriol.* 176:7719–7726 (1994)). In contrast, the crtM homolog of diapophytoene synthase could not be identified in *Methylomonas* (FIG. 4A). In *Methylomonas* 16a, the condensation of FPP is catalyzed by the enzyme encoded by the sqs gene, to yield squalene. Sqs was also observed to produce low amount of diapophytoene in addition to squalene. This biosynthetic process whereby squalene acts as a key intermediate corresponds with that proposed by Kleinig, H. and R. Schmitt for *Pseudomonas rhodos* (*Z. Naturforsch* 37c: 758–760 (1982)).

The common substrate diapophytoene is then successively desaturated by a diapophytoene desaturase (CrtN) to form either diapocarotene in *Methylomonas* 16a, or 4,4'-diaponeurosporene in *S. aureus*. The subsequent reaction on each of these substrates appears to be catalyzed by the enzymes encoded by the crtN2 genes. As described in U.S. Ser. No. 10/358,917 and herein, crtN2 genes have been identified in both *Methylomonas* 16a and *S. aureus* (ATCC 35556) that possess great homology to one another (51% identity and 68% similarity, based on amino acid sequence comparison of the CrtN2 proteins). Previously, the crtN2 gene of *S. aureus* had been identified as a hypothetical protein.

Although the crtN2 gene acts on different natural substrates, careful analysis of its function revealed that both crtN2 genes possess the ability to produce omega-aldehyde functional groups on those carotenoid compounds which possess a 7-8 or 7'-8' desaturated ψ group (wherein the term "ψ group" will refer to the end group of a carotenoid molecule possessing a $C_9H_{15}$ structure, as shown by the circled portion of the diaponeurosporene molecule in FIG. 4B; in contrast, a "desaturated ψ group" will refer to an end group, as represented by the formula $C_9H_{13}$ and shown as the boxed structure in FIGS. 4A and 4B). Diapocarotene is converted to diapocarotene-dial in 16a, while in *S. aureus* the CrtN2 enzyme is responsible for the conversion of diaponeurosporene to diaponeurosporene-al. The interchangeability of these genes, due to their common functionality, has been proven by studies that demonstrated that the *Methylomonas* crtN2 and *Staphylococcus* crtN2 genes both catalyzed the synthesis of diaponeurosporene-al from diaponeurosporene, and synthesis of diapocarotene-dial from diapocarotene in *E. coli* (U.S. Ser. No. 10/358,917; corresponding to WO 03/068917).

Finally, functional analysis of the *Methylomonas* aldehyde dehydrogenase gene (ald) confirmed that this enzyme was responsible for catalyzing the oxidation of the diapocarotene-dial aldehyde to its corresponding carboxylic acid (diapocarotene-diacid) (FIG. 4A), by formation of an omega-carboxyl functional group on the 7–8 and 7'-8' desaturated ψ group of the conjugated polyene carbon skeleton of the carotenoid substrate. Although a similar chemical reaction occurs in the *S. aureus* $C_{30}$ pathway, whereby carboxylation of diaponeurosporene-al occurs to produce diaponeurosporene-acid, the gene catalyzing this particular reaction has not yet been identified.

Construction of a Genetic Pathway Suitable for Producing $C_{30}$-Aldehyde Carotenoids Based on the above analyses of enzyme functionality of the $C_{30}$ lower carotenoid biosynthetic genes sqs, crtM, crtN, crtN2, and ald from these two diverse microorganisms, an engineered pathway was designed that would enable production of $C_{30}$-aldehyde carotenoids in a variety of host organisms which possess suitable levels of FPP as a precursor (of course, FPP synthesis can be engineered into the host by the introduction of the upper pathway isoprene genes). Specifically, this engineered pathway comprises a series of reactions catalyzed by the following enzymes:

1. An enzyme(s) capable of converting FPP to diapophytoene (e.g., *Staphylococcus* CrtM (SEQ ID NO:10) or *Methylomonas* Sqs (SEQ ID NO:2) or a homologous enzyme thereof having similar enzymatic activity and functionality);
2. An enzyme(s) capable of desaturating diapophytoene (e.g., *Staphylococcus* CrtN (SEQ ID NO:12) or *Methylomonas* CrtN (SEQ ID NO:4) or a homologous enzyme thereof having similar enzymatic activity and functionality);
3. An enzyme(s) capable of introducing an omega-aldehyde functional group on the omega carbon of the conjugated polyene carbon skeleton of the carotenoid compound produced by the CrtN enzyme described above (e.g., the *Staphylococcus* CrtN2 (SEQ ID NO:14) or the *Methylomonas* CrtN2 (SEQ ID NO:8) or a homologous enzyme thereof having similar enzymatic activity and functionality).

The specific $C_{30}$-aldehyde carotenoid that one desires to produce will affect the choice of enzyme encoding each of the functions described above when creating an engineered pathway. For example, synthesis of diaponeurosporene-monoaldehyde would require use of the *Staphylococcus* CrtN, as opposed to the *Methylomonas* CrtN (since the *Staphylococcus* CrtN catalyzes a single desaturation step, to convert diapophytoene to diaponeurosporene). In contrast, for production of either the $C_{30}$ diapocarotene monoaldehyde or diapocarotene dialdehyde, the *Methylomonas* CrtN must be utilized (since this enzyme catalyzes one additional desaturation step on diapophytoene [relative to the *Staphylococcus* CrtN] to form diapocarotene); however, if may also be desirable to include both the *Staphylococcus* CrtN and the *Methylomonas* CrtN, since this may increase desaturase activity for $C_{30}$ diapocarotene aldehyde synthesis.

In a preferred embodiment, wherein the desired carotenoid product is $C_{30}$ diapocarotene dialdehyde, the engineered pathway comprises the *Staphylococcus* CrtM (SEQ ID NO:10), both the *Staphylococcus* CrtN (SEQ ID NO:12) and the *Methylomonas* CrtN (SEQ ID NO:4), and the *Methylomonas* CrtN2 (SEQ ID NO:8).

Traditional Methods for Genetically Engineering Production of $C_{30}$-Aldehyde Carotenoids in Recombinant Microorganisms Methods for introduction of genes encoding the appropriate upper isoprene pathway genes (if necessary) and the lower carotenoid biosynthetic pathway genes of the engineered pathway for $C_{30}$-aldehyde carotenoid synthesis into a suitable microbial host are common.

Microbial expression systems and expression vectors containing regulatory sequences that direct high-level expression of foreign proteins are well known to those skilled in the art. Any of these could be used to construct chimeric genes for production of $C_{30}$-aldehyde carotenoids using the gene products of the present sequences. These chimeric genes could then be introduced into appropriate microorganisms via transformation to provide high-level expression of the enzymes.

Vectors or cassettes useful for the transformation of suitable host cells are well known in the art. Typically the vector or cassette contains sequences directing transcription and translation of the relevant gene(s), a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the instant ORF's in the desired host cell are numerous and familiar to those skilled in the art. Virtually any promoter capable of driving these genes is suitable for the present invention including, but not limited to: CYC1, HIS3, GAL1, GAL10, ADH1, PGK, PHO5, GAPDH, ADC1, TRP1, URA3, LEU2, ENO, TP1 (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*. Additionally, the deoxy-xylulose phosphate synthase or methanol dehydrogenase operon promoter (Springer et al., FEMS *Microbiol Lett* 160:119–124 (1998)), the promoter for polyhydroxyalkanoic acid synthesis (Foellner et al., *Appl. Microbiol. Biotechnol.* 40:284–291 (1993)), promoters identified from native plasmids in methylotrophs (EP 296484), Plac (Toyama et al., *Microbiology* 143:595–602 (1997); EP 62971), Ptrc (Brosius et al., *Gene* 27:161–172 (1984)), promoters identified from methanotrophs (PCT/US03/33698), and promoters associated with antibiotic resistance [e.g., kanamycin (Springer et al., FEMS *Microbiol Lett* 160:119–124 (1998); Ueda et al., *Appl. Environ. Microbiol.* 57:924–926 (1991)) or tetracycline (U.S. Pat. No. 4,824,786)] are suitable for expression.

It is necessary to include an artificial ribosomal binding site ("RBS") upstream of a gene to be expressed, when the RBS is not provided by the vector. This is frequently required for the second, third, etc. gene(s) of an operon to be expressed, when a single promoter is driving the expression of a first, second, third, etc. group of genes. Methodology to determine the preferred sequence of a RBS in a particular host organism will be familiar to one of skill in the art, as are means for creation of this synthetic site.

Termination control regions may also be derived from various genes native to the preferred hosts. Optionally, a termination site may be unnecessary; however, it is most preferred if included.

Merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: 1.) the nature of the relevant transcriptional promoter and terminator sequences; 2.) the strength of the ribosome binding site; 3.) the number of copies of the cloned gene and whether the gene is plasmid-borne or integrated into the genome of the host cell; 4.) the final cellular location of the synthesized foreign protein; 5.) the efficiency of translation in the host organism; 6.) the intrinsic stability of the cloned gene protein within the host cell; and 7.) the codon usage within the cloned gene, such that its frequency approaches the frequency of preferred codon usage of the host cell. Each of these types of modifications are encompassed in the present invention, as means to further optimized expression of $C_{30}$-aldehyde carotenoids.

Insertion of the present genes into the appropriate host cell will be sufficient for the production of $C_{30}$-aldehyde carotenoids, provided however that the host cell comprises suitable levels of the substrate farnesyl pyrophosphate. As discussed above, farnesyl pyrophosphate is the end product of the upper isopreoid pathway and, in the present invention, is converted by the action of enzymes encoded by the sqs, crt N2 and crtN genes to the desired $C_{30}$-aldehyde carotenoids of the invention. "Suitable levels" of farnesyl pyrophosphate may be provided by an endogenous upper isoprenoid pathway which is ubiquitous in many microorganisms and plants. Alternatively, the genes of the upper isoprenoid pathway are well know and highly characterized and the essential elements of the pathway could be introduced into a host cell for the production of farnesyl pyrophosphate. Finally, where no enzymatic system is available for the production of farnesyl pyrophosphate, it can be added directly to the medium of a cell culture or other growth system. The skilled person will appreciate that the levels of farnesyl pyrophosphate required will depend on a number of factors including the efficiency of the expression of the downstream pathways and the metabolic and physiological nature of the host cell.

Finally, to promote accumulation of $C_{30}$-aldehyde carotenoids, it may be necessary to reduce or eliminate the expression of certain genes in the target pathway or in competing pathways that may serve as sinks for energy or carbon. Alternatively, it may be useful to over-express various genes upstream of desired carotenoid intermediates to enhance production. Methods of manipulating genetic pathways for the purposes described above are common and well known in the art.

For example, once a key genetic pathway has been identified and sequenced, specific genes may be up-regulated to increase the output of the pathway. For example, additional copies of the targeted genes may be introduced into the host cell on multicopy plasmids such as pBR322. Optionally, one or more targeted genes may be chromosomally-integrated into the host cell. Alternatively, the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, U.S. Pat. No. 5,565,350; Zarling et al., PCT/US93/03868).

Alternatively, where sequence of the gene to be disrupted is known, one of the most effective methods for gene down-regulation is targeted gene disruption, where foreign DNA is inserted into a structural gene so as to disrupt transcription. This can be effected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.* 171:4617–4622 (1989); Balbas et al., *Gene* 136:211–213 (1993); Gueldener et al., *Nucleic Acids Res.* 24:2519–2524 (1996); and Smith et al., *Methods Mol. Cell. Biol.* 5:270–277(1996)).

Antisense technology is another method of down-regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA encoding the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36: 227–234 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see, for example: The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wiss., based upon the Tn5 bacterial transposable element).

Within the context of the present invention, it may be useful to modulate the expression of the carotenoid biosynthetic pathway by any one of the methods described above. For example, the present invention provides methods leading to the production of $C_{30}$-aldehyde carotenoids. In addition to over-expressing the sqs, crtM, crtN, and crtN2 genes to promote increased production of $C_{30}$-aldehyde carotenoids, it may also be useful to up-regulate the initial condensation of 3-carbon compounds (pyruvate and D-glyceraldehyde 3-phosphate) to increase the yield of the 5-carbon compound D-1-deoxyxylulose-5-phosphate (mediated by the dxs gene). This would increase the flux of carbon entering the carotenoid biosynthetic pathway and permit increased production of $C_{30}$-aldehyde carotenoids. Alternatively (or in addition to), it may be desirable to knockout the crtE genes leading to the synthesis of $C_{40}$ carotenoids, if the microbial host is capable of synthesizing these types of compounds.

Triple Homologous Recombination Methods for Genetically Engineering Production of $C_{30}$-Aldehyde Carotenoids in Recombinant Microorganisms U.S. Ser. No. 10/734,936 teaches a method of targeted in vivo chromosomal engineering using triple homologous recombination to rapidly insert strong promoters upstream of desired elements for gene up-regulation (see FIG. 5). This methodology was used to increase $C_{40}$ carotenoid (i.e., β-carotene) production in *E. coli* (U.S. Ser. No. 10/734,778 and U.S. Ser. No. 10/735,442).

This method requires use of: 1.) a recombinant proficient bacterial host (i.e., containing the phage λ-Red recombination system); and 2.) two linear, double-stranded, PCR-generated DNA fragments, wherein homologous recombination produces an "integration cassette" whose general structure is as follows: 5'-RR1-RS-SM-RS-X-RR3-3', wherein: (i) RR1 is a first homology arm of about 10 to 50 bases having homology to an upstream portion (or first region) of a donor cell chromosome; (ii) RS is a recombination site (e.g., Frt) responsive to a site-specific recombinase (e.g., Flp); (iii) SM is a DNA fragment encoding a selectable marker (e.g., Kan); (iv) X is a first expressible DNA fragment; and (v) RR3 is a third homology arm, having homology to a downstream portion (or second region) of a donor cell chromosome (FIG. 5). Multiple genetic traits can be introduced into one host in a parallel combinatorial fashion, using the bacteriophage P1 in combination with a site-specific recombinase system for removal of selection markers (U.S. Ser. No. 10/734,778).

Expressible DNA fragments are those that will be useful in the genetic engineering of pathways. For example, it may be useful to engineer a strong promoter in place of a native promoter in certain pathways. Alternatively, different coding regions may be introduced downstream of existing native promoters, to thereby introduce new coding regions comprising a biosynthetic pathway to complete or enhance a pathway already in existence in the host cell. Thus, the phage T5 strong promoter is used in the present invention to replace endogenous promoters that modulate the activity of the native dxs, idi, and ispAdxs genes in *E. coli*, increasing overall carotenoid production.

Integration Cassettes

As used in the present invention, "integration cassettes" are the linear double-stranded DNA fragments chromosomally integrated by homologous recombination via two PCR-generated linear fragments as seen in FIG. 5. The integration cassette comprises a nucleic acid integration fragment that is a promoter and/or gene, a selectable marker bounded by specific recombinase sites responsive to a recombinase, and homology arms having homology to different portions of a donor cell chromosome. The homology arms, generally about 10 to 50 base pairs in length, are chosen so have homology with either a specific sequence on the bacterial chromosome or a specific sequence on another recombination element.

The native promoter of the isoprenoid genes is replaced with the phage T5 strong promoter in combination with a selection marker by using two linear, double-stranded DNA (dsDNA), PCR-generated fragments (FIG. 5).

Integration cassettes may contain one or more genes or coding sequences. These genes may be natural or foreign to the host cell and may include those that have undergone previous modification, such as transposon disruption. In the present method, genes useful in optimization of isoprenoid/carotenoid production are used.

Integration cassettes can include selectable markers, preferably flanked by site-specific recombination sequences, allowing for easy removal of the markers after selection. The selectable marker is selected from the group consisting of antibiotic resistance markers, enzymatic markers wherein the expressed marker catalyzes a chemical reaction creating a measurable difference in phenotypic appearance, and amino acid biosynthesis enzymes which enable a normally auxotrophic bacteria to grow without the exogenously supplied amino acid; the amino acid synthesized by the amino acid biosynthesis enzyme.

λ-Red Recombinase System

The terms "recombinase" or "recombinase system" refer to one or more enzymes, which either work alone or in combination to stimulate homologous recombination. The "λ-Red recombinase", "λ-Red recombination system", and "λ-Red system" are used interchangeably to describe a group of enzymes encoded by the bacteriophage λ genes exo, bet, and gam. The enzymes encoded by the three genes work together to increase the rate of homologous recombination in *E. coli*, an organism generally considered to have a relatively low rate of homologous recombination; especially when using linear recombination elements.

Bacteriophage P1 Transduction System

Transduction is a phenomenon in which bacterial DNA is transferred from one bacterial cell (the donor) to another (the recipient) by a phage particle containing bacterial DNA. When a population of donor bacteria is infected with a phage, the events of the phage lytic cycle may be initiated. During lytic infection, the enzymes responsible for packaging viral DNA into the bacteriophage sometimes accidentally package host DNA. The resulting particle is called a transducing particle. Upon lysis of the cell these particles, called P1 lysate, are released along with normal virions, and so the lysate contains a mixture of normal virions and transducing particles. When this lysate is used to infect a population of recipient cells, most of the cells become infected with normal virus. However, a small proportion of the population receives transducing particles that inject the DNA they received from the previous host bacterium. This DNA can now undergo genetic recombination with the DNA of the another host. Conventional P1 transduction can move only one genetic trait (i.e. gene) at a time from one to another host. The Applicants used this method for stacking multiple genetic traits into one *E. coli* host in a parallel fashion using the bacteriophage P1 mixtures in combination with the site-specific recombinase system for removal of selection markers.

Preferred Microbial Hosts

Preferred heterologous host cells for expression of the $C_{30}$ lower carotenoid biosynthetic pathway genes (i.e., crtM, sqs, crtN, crtN2) are microbial hosts that can be found broadly within the fungal or bacterial families and which grow over a wide range of temperature, pH values, and solvent tolerances. For example, it is contemplated that any bacteria, yeast, and filamentous fungi will be suitable hosts for expression of the present nucleic acid fragments. Because transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and/or saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, and carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of host strains include, but are not limited to: fungal or yeast species such as *Aspergillus, Trichoderma, Saccharomyces, Pichia, Phaffia, Candida, Rhodotorula, Rhodosporidium, Hansenula*; or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Methylobacterium, Alcaligenes, Synechocystis, Synechococcus, Anabaena, Thiobacillus, Methanobacterium, Klebsiella, Myxococcus*, and *Staphylococcus*.

In a preferred embodiment, *E. coli* is used as a host for heterologous carotenoid production since genes of the $C_{30}$ lower carotenoid biosynthetic pathway can be functionally expressed in this organism, many genetic tools are available for use, and the organism is often used as a production host for large-scale bioprocesses.

Engineering *E. coli* for increased carotenoid production has frequently focused on overexpression of key isoprenoid pathway genes from multi-copy plasmids; however, engineering the supply of isoprenoid precursors for increased production of exogenous carotenoids is often necessary. It has been shown that a rate-limiting step in carotenoid biosynthesis is the isomerization of IPP to DMAPP (Kajiwara et al., *Biochem. J.* 423: 421–426 (1997)). It was also found that the conversion from FPP to GGPP is the first functional limiting step for the production of $C_{40}$ carotenoids in *E. coli* (Wang et al., *Biotchnol. Prog.* 62: 235–241 (1999)). Transformation of *E. coli* with the genes for overexpression of isopentenyl diphosphate isomerase (idi), deoxy-D-xylulose-5-phosphate (DXP) synthase (dxs), and DXP reductoisomerase (dxr) from various sources was found to increase production of carotenoids by a factor of 3.5 (Albrecht et al., *Biotechnol. Lett.* 21:791–795 (1999)). Thus, numerous modifications via metabolic engineering are possible to increase the production of carotenoids in this host.

Industrial Production of $C_{30}$-Aldehyde Carotenoids in a Recombinant Microbial Host Where commercial production of the instant $C_{30}$-aldehyde carotenoid compounds are desired, a variety of culture methodologies may be applied. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur (while adding nothing to the system). Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase, where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art; examples may be found in Brock (supra) or Deshpande (supra).

Commercial production of the instant carotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products, or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art of industrial microbiology and a variety of methods are detailed by Brock, supra.

Fermentation media in the present invention must contain suitable fermentable carbon substrates. Suitable substrates may include, but are not limited to: monosaccharides (e.g., glucose and fructose), disaccharides (e.g., lactose or sucrose), polysaccharides (e.g., starch or cellulose or mixtures thereof), and unpurified mixtures from renewable feedstocks (e.g., cheese whey permeate, cornsteep liquor, sugar beet molasses, and barley malt). Additionally, the carbon substrate may also be one-carbon (single carbon) substrates such as carbon dioxide, methane or methanol for which metabolic conversion into key biochemical intermediates has been demonstrated. In addition to one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), pp 415–32. Murrell, J. Collin and Don P. Kelly, Eds. Intercept: Andover, UK). Similarly, various species of *Candida* will metabolize alanine or oleic acid (Sulter et al., *Arch. Microbiol.* 153: 485–489 (1990)). Hence it is contemplated that the source of carbon utilized in the present invention may encompass a wide variety of carbon-containing substrates and will only be limited by the choice of organism.

In vitro Bio-Conversion of Carotenoids

Alternatively, it is possible to carry out the bioconversions of the present application in vitro. Where substrates for the crtM, sqs, crtN and crtN2 enzymes are not synthesized endogenously by the host cell, it will be possible to add the substrate exogenously. In this embodiment the suitable carotenoid substrate may be solubilized with mild detergent (e.g., DMSO) or mixed with phospholipid vesicles. To assist in transport into the cell, the host cell may optionally be permeabilized with a suitable solvent such as toluene. Methods for this type of in-vitro bio-conversion of carotenoid substrates has basis in the art (see for example: Hundle, B. S., et al., *FEBS* 315:329–334 (1993); and Bramley, P. M., et al., *Phytochemistry* 26:1935–1939 (1987)).

Genetically Engineered Recombinant Plants for Production of $C_{30}$-Aldehyde Carotenoids Plants and algae are also known to produce carotenoid compounds. The nucleic acid fragments of the $C_{30}$ lower carotenoid biosynthetic pathway (i.e., crtM, sqs, crtN, and crtN2) may be used to create transgenic plants having the ability to express these genes for the production of $C_{30}$-aldehyde carotenoids.

Preferred plant hosts will be any variety that will support a high production level of the instant carotenoids. Thus, suitable green plants will include, but are not limited to: soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp.), barley (*Hordeum vulgare*), oats (*Avena sativa*, L), sorghum (*Sorghum bicolor*), rice (*Oryza sativa*), Arabidopsis, cruciferous vegetables (e.g., broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, marigold flower and forage grasses. Algal species include, but are not limited to commercially significant hosts such as *Spirulina, Haemotacoccus*, and *Dunalliela*.

Overexpression of $C_{30}$-aldehyde carotenoid compounds in these hosts may be accomplished by first constructing chimeric genes of the present invention in which the coding regions are operably linked to promoters capable of directing expression of a gene in the desired plant tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences of the present invention should be capable of promoting expression of the present gene product(s). High-level plant promoters that may be used in this invention, for example, include the promoter of the small subunit (ss) of the ribulose-1,5-bisphosphate carboxylase from soybean (Berry-Lowe et al., *J. Molecular and App. Gen.*, 1:483–498 1982)) and the promoter of the chlorophyll a/b binding protein. These two promoters are known to be light-induced in plant cells (see, for example, *Genetic Engineering of Plants, an Agricultural Perspective*, A. Cashmore, Plenum: N.Y. (1983), pp 29–38; Coruzzi, G. et al., *J. Biol. Chem.* 258:1399 (1983); and Dunsmuir, P. et al., *J. Mol. Appl. Genetics* 2:285 (1983)).

Plasmid vectors comprising the instant chimeric genes can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene. For example, techniques of transformation include: 1.) transformation with DNA employing *A. tumefaciens* or *A. rhizogenes* as the transforming agent; 2.) direct uptake of foreign DNA constructs (see EP 295959); 3.) techniques of electroporation (see Fromm et al., *Nature* (London) 319:791 (1986)); or 4.) high-velocity ballistic bombardment with metal particles coated with the nucleic acid constructs (see Kline et al., *Nature* (London) 327:70 (1987); U.S. Pat. No. 4,945,050). Once transformed, the cells can be regenerated by those skilled in the art. This typically requires the transgenic plant cells to be placed in an appropriate selective medium for selection of transgenic cells that are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will allow for selection of transformed cells as compared to cells lacking the DNA that has been introduced.

The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus multiple events must be screened in order to obtain lines displaying the desired expression level and pattern. Such screening may be accomplished by Southern analysis of DNA blots (Southern, *J. Mol. Biol.* 98:503 (1975)), Northern analysis of mRNA expression (Kroczek, *J. Chromatogr. Biomed. Appl.* 618 (1–2):133–145 (1993)), Western analysis of protein expression, or phenotypic analysis.

For some applications it will be useful to direct the instant proteins to different cellular compartments. It is thus envisioned that the chimeric genes encoding enzymes of the $C_{30}$ lower carotenoid biosynthetic pathway may be further supplemented by altering the coding sequences to encode the enzymes with appropriate intracellular targeting sequences such as transit sequences (Keegstra, K., *Cell* 56:247–253 (1989)), signal sequences, sequences encoding endoplasmic reticulum localization (Chrispeels, J. J., *Ann. Rev. Plant Phys. Plant Mol. Biol.* 42:21–53 (1991)), or nuclear localization signals (Raikhel, N., *Plant Phys.* 100: 1627–1632 (1992)) added and/or with targeting sequences that are already present removed. While the references cited give examples of each of these, the list is not exhaustive and more targeting signals of utility may be discovered in the future that will be useful in the invention.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Maniatis (supra), Silhavy et al. (supra), and Ausubel et al. (supra).

Materials and methods suitable for the maintenance and growth of bacterial cultures are well known in the art. Techniques suitable for use in the following examples may be found as set out in: *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); Brock (supra); or by Deshpande (supra). All reagents, restriction enzymes and materials used for the growth and maintenance of bacterial cells were obtained from Aldrich Chemicals (Milwaukee, Wiss.), DIFCO Laboratories (Detroit, Mich.), GIBCO/BRL (Gaithersburg, Md.), or Sigma Chemical Company (St. Louis, Mo.), unless otherwise specified.

Manipulations of genetic sequences were accomplished using the suite of programs available from the Vector NTI version 7.0 (Informax, Inc., Bethesda, Md.) which default values were used.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmol" mean micromole(s), "g" means gram(s), "μg" means microgram(s), "ng" means nanogram(s), "U" means unit(s), "bp" means base pair(s), and "kB" means kilobase(s).

Additionally, antibiotics used for selection of microbial strains will be abbreviated as follows: "Kan" means kanamycin, "Amp" means ampicillin, "Tet" means tetracycline, and "Cam" means chloramphenicol.

Plasmids

For ease of understanding, the following plasmids were used in these studies.

TABLE 4

Plasmids Used in this Application

| Plasmid | Backbone | Expressed gene(s) and Organism[1] |
|---|---|---|
| pDCQ150 | pCR2.1-TOPO | crtN1 (16a)-ald (16a)-crtN2 (16a) |
| pDCQ153 | pTrcHis2-TOPO | crtM (S. aureus) |
| pDCQ155 | pTrcHis2-TOPO | crtM (S. aureus)-crtN (16a)-ald (16a)-crtN2 (16a) |
| pDCQ155::Tn5 p33 | pTrcHis2-TOPO | crtM (S. aureus)-crtN (16a)-[ald (16a)]*-crtN2 (16a) *ald(16a) knock-out |
| pDCQ165 | pTrcHis2-TOPO | crtM (S. aureus)-crtN (S. aureus) |
| pDCQ166 | pBHR1[2] | crtM (S. aureus)-crtN (S. aureus) |
| pDCQ167 | pTrcHis2-TOPO | crtN2 (16a) |
| pDCQ174 | pTrcHis2-TOPO | crtN (16a) |
| pDCQ175 | pTrcHis2-TOPO | crtN (16a) with artificial ribosome binding site |
| pDCQ176 | pTrcHis2-TOPO | crtN2 (16a) with artificial ribosome binding site |
| pDCQ177 | pTrcHis2-TOPO | crtN (16a)-crtN2 (16a) |
| pDCQ178 | pTrcHis2-TOPO | crtN2 (16a)-crtN (16a) |

[1]Organism refers to that from which the gene was isolated (16a = *Methylomonas* 16a; *S. aureus* = *Staphylococcus aureus*).
[2]MoBiTec (Goettingen, Germany)

Microbial Cultivation for *Methylomonas* sp. 16a

The conditions described in published U.S. patent application US 2003003528 (herein incorporated by reference) were used throughout the experimental Examples for treatment of *Methylomonas* 16a, unless conditions were specifically mentioned to be different. Briefly, this involved growing *Methylomonas* 16a in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking. The standard gas phase for cultivation contained 25% methane in air.

Nitrate liquid medium, also referred to herein as "defined medium" or "BTZ-3" medium was comprised of various salts mixed with Solution 1 as indicated below (Tables 5 and 6) or where specified the nitrate was replaced with 15 mM ammonium chloride. Solution 1 provides the composition for 100-fold concentrated stock solution of trace minerals.

TABLE 5

Solution 1*

|  | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to an end volume of 1 L. Keep refrigerated.

TABLE 6

Nitrate liquid medium (BTZ-3)**

|  | MW | Conc. (mM) | g per L |
|---|---|---|---|
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7) | 238.3 |  | 50 mL |
| Solution 1 |  |  | 10 mL |

**Dissolve in 900 mL $H_2O$. Adjust to pH = 7, and add $H_2O$ to give 1 L. For agar plates: Add 15 g of agarose in 1 L of medium, autoclave, let cool down to 50° C., mix, and pour plates.

HPLC Analysis of Carotenoid Content

The following HPLC protocol was used for carotenoid analysis, unless otherwise indicated. A Beckman System Gold® HPLC with Beckman Gold Nouveau Software (Columbia, Md.) was used for the study, along with a 125×4 mm RP8 (5 μm particles) column with corresponding guard column (Hewlett-Packard, San Fernando, Calif.). The spectral data was collected by a Beckman photodiode array detector (Model 168).

For analysis of carotenoid content, the following HPLC parameters were used: flow rate: 1 mL/min; solvent program: 0–11.5 min linear gradient from 40% water/60% methanol to 100% methanol, 11.5–20 min 100% methanol, 20–30 min 40% water/60% methanol.

Example 1

Native Carotenoid of *Methylomonas* 16a

HPLC analysis of acetone extracts of the native carotenoids produced by *Methylomonas* 16a confirmed that one major carotenoid (net retention volume at about 6 mL) is responsible for the pink coloration of the wild-type *Methylomonas* 16a cells.

Specifically, for carotenoid determination, *Methylomonas* 16a was grown in 100 mL BTZ-3 medium under methane (25%) for three days to stationary phase. Cells were spun down, washed with distilled water, and freeze-dried (lyophilizer: Virtis, Gardiner, N.Y.) for 24 hr in order to determine dry-weights. After the dry-weight of each culture was determined, cells were extracted.

First, cells were welled with 0.4 mL of water and let stand for 15 min. After 15 min, 4 mL of acetone was added and thoroughly vortexed to homogenize the sample. The samples were then shaken at 30° C. for 1 h, and then centrifuged. Pink coloration was observed in the supernatant. The supernatant was collected and pellets were extracted again with 0.3 mL of water and 3 mL of acetone. The supernatants from the second extraction were lighter pink in color. The supernatants of both extractions were combined. Their volumes were measured and analyzed spectrophotometrically.

A crude acetone extract from *Methylomonas* 16a cells has a typical absorption spectrum 460 nm, 491 nm, 522 nm measured by spectrophotometer (Amersham Pharmacia Biotech, Piscataway, N.J.).

In order to confirm the structure of this major carotenoid, *Methylobacterium rhodinum* (formerly *Pseudomonas rhodos*; ATCC 14821) of which $C_{30}$-carotenoid was identified was used as a reference strain (Kleinig et al., *Z. Naturforsch* 34c:181–185 (1979); Kleinig and Schmitt, *Z. Naturforsch* 37c:758–760 (1982)). A saponified extract of *Methylobacterium rhodinum* and of *Methylomonas* 16a were compared by HPLC analysis under the same conditions as described above. The results are shown as follows:

Saponified *M. rhodinum*:
  Absorption maxima: 460 nm, 487 nm, 517 nm
  Net retention volume=1.9 mL Saponified *Methylomonas* 16a:
  Absorption maxima: 460 nm, 488 nm, 518 nm
  Net retention volume=2.0 mL HPLC analysis results suggested that the carotenoid from *Methylomonas* 16a has the same $C_{30}$ carotenoic acid backbone as that from *Methylobacterium rhodinum*. Chemical reduction experiments were also performed to verify the carboxylation of the 16a carotenoid. The carotenoid carboxylic acids or their esters can only be reduced by $LiAlH_4$ to their primary corresponding carotenols. The carbonyl function of carotenoid aldehydes or ketones can be reduced by $NaBH_4$ or $LiAlH_4$ to alcohol.

Experiments showed that the 16a native carotenoid was reduced by $LiAlH_4$ as indicated by color change from pink to yellow (as well as the HPLC analysis). However, it could not be reduced by $NaBH_4$. The results were consistent with the presence of a carboxylic acid or ester in the native 16a carotenoid.

Example 2

Identification and Characterization of Bacterial Genes from *Methylomonas*

Genomic DNA was isolated from *Methylomonas* 16a, prepared and used for library construction and shotgun sequencing, according to the procedures described in WO 02/18617.

Subsequently, all sequences were identified by conducting BLAST (Basic Local Alignment Search Tool; Altschul, S. F., et al., *J. Mol. Biol.* 215:403–410 (1993); see also www.ncbi.nlm.nih.gov/BLAST/) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J., *Nature Genetics* 3:266–272 (1993)) provided by the NCBI. All comparisons were done using either the BLASTNnr or BLASTXnr algorithm.

The results of these BLAST comparisons are given below in Table 7 for genes of the present invention. Table 7 summarizes the sequence to which each *Methylomonas* gene has the most similarity (presented as % similarities, % identities, and expectation values). The table displays data based on the BLASTXnr algorithm with values reported in Expect values. The Expect value estimates the statistical significance of the match, specifying the number of matches, with a given score, that are expected in a search of a database of this size absolutely by chance.

Two carotenoid biosynthesis gene clusters were identified in the genomic sequence of *Methylomonas* sp. 16a, as shown in FIG. 3A. The first gene cluster was identified containing 2 genes. The gene sqs (ORF 1) encodes a putative squalene synthase with the highest BLAST hit to squalene synthase from *Methylococcus capsulatus* (60% identity and 73% similarity). The second gene was identified as a squalene-hopene cyclase (Shc) encoded by the shc gene. Shc catalyzes the complex cyclization of squalene to the pentacyclic triterpene skeleton of hopanoids, a pathway that is not related to the lower carotenoid pathway.

In a second operon, three genes were encoded on this cluster (FIG. 3A). The first gene (designated crtN; ORF 2) encodes a putative diapophytoene dehydrogenase with the highest BLAST hit to a diapophytoene dehydrogenase from *Heliobacillus mobilis* (34% identity and 58% similarity). The middle gene (designated ald; ORF 3) encodes a putative aldehyde dehydrogenase with the highest BLAST hit to a betaine aldehyde dehydrogenase from *Arabidopsis thaliana* (33% identity and 50% similarity). The third gene (designated crtN2; ORF 4) also encodes a putative diapophytoene dehydrogenase with the highest BLAST hit to a hypothetical protein of a phytoene dehydrogenase family from *Staphylococcus aureus* (51% identity and 67% similarity).

TABLE 7

Identification of *Methylomonas* sp. 16a Genes Based on Sequence Homology

| ORF Name | Gene Name | Similarity Identified | SEQ ID | SEQ ID peptide | % Identity [a] | % Similarity [b] | E-value [c] | Citation |
|---|---|---|---|---|---|---|---|---|
| 1 | sqs | emb\|CAA71097.1 squalene synthase [*Methylococcus capsulatus*] | 1 | 2 | 60 | 73 | e–109 | Tippelt, A. et al., Biochim. Biophys. Acta 1391(2): 223–232 (1998) |
| 2 | crtN | pir\|T31463\|CrtN diapophytoene dehydrogenase [*Heliobacillus mobilis*] | 3 | 4 | 34 | 58 | e–93 | Xiong, J. et al., P.N.A.S. 95(6685): 14851–14856(1998) |

TABLE 7-continued

Identification of *Methylomonas* sp. 16a Genes Based on Sequence Homology

| ORF Name | Gene Name | Similarity Identified | SEQ ID | SEQ ID peptide | % Identity [a] | % Similarity [b] | E-value [c] | Citation |
|---|---|---|---|---|---|---|---|---|
| 3 | ald | gb\|AAG50992.1\|AC036 106_5 betaine aldehyde dehydrogenase [*Arabidopsis thaliana*] | 5 | 6 | 33 | 50 | 4e–66 | Lin, X. et al., Unpublished |
| 4 | crtN2 | dbj\|BAB43655.1\| hypothetical protein ORF SA2351 [*Staphylococcus aureus*] | 7 | 8 | 51 | 67 | e–133 | Kuroda, M. et al., Lancet 397(9264): 1225–1240(1998) |

[a] % Identity is defined as percentage of amino acids that are identical between the two proteins.
[b] % Similarity is defined as percentage of amino acids that are identical or conserved between the two proteins.
[c] Expect value. The Expect value estimates the statistical significance of the match, specifying the number of matches, with a given score, that are expected in a search of a database of this size absolutely by chance.
% Identity, % similarity, and e-values are all reported according to BLAST analysis.

Example 3

Preliminary Synthesis of Diapocarotene Dialdehyde in Recombinant *E. coli*

The *Methylomonas* 16a carotenoid gene cluster crtN-ald-crtN2, in conjunction with the *Staphylococcus aureus* crtM, was expressed in an *E. coli* strain (*E. coli* is naturally able to synthesize FPP using the upstream isoprenoid pathway shown in FIG. 1). Upon disruption of the ald gene by transposon mutagenesis, diapocarotene dialdehyde was detected in the transformed host.

Synthesis of Plasmid pDCQ153 (Comprising *Staphylococcus* crtM)

First, the *staphylococcal* crtM gene (SEQ ID NO:9) was shown to encode a dehydrosqualene synthase (Wieland, et al., *J. Bacteriol.* 176:7719–7726 (1994)). Primers crtM_F/Staphyl (SEQ ID NO:15) and crtM_R/Staphyl (5'-ggatcctatattctatgatatttactatttatttc-3'; SEQ ID NO:16) (incorporated BamHI site is underlined) were used to amplify the 869 bp crtM gene from *Staphylococcus aureus* ATCC 35556. The amplified gene product was cloned into the pTrcHis2-TOPO expression vector (Invitrogen, Carlsbad, Calif.) and the resulted construct, with crtM gene in the forward orientation, was designated as pDCQ153 (Table 4).

Synthesis of Plasmid pDCQ155 (comprising the *Methylomonas* crtN-ald-crtN2 gene cluster) and Analysis of *E. coli* Transformants Then, primers crtN_FL (5'-GGTCTCAAATTGCATCMCGGATCATC ATGGCCMC-3'; SEQ ID NO:17) and crtN_RL (5'-GGTCTCTAATTGCTAGCTTA TTGCA MTCCGCCAC-MTCTTGTC-3'; SEQ ID NO:18) (incorporated BsaI sites are underlined) were used to amplify the 4668 bp crtN-ald-crtN2 gene cluster from *Methylomonas* 16a. The amplified product was first cloned into the pCR2.1-TOPO vector (Invitrogen) to form pDCQ150. The BsaI fragment of pDCQ150 containing the crtN-ald-crtN2 cluster was then cloned into the EcoRI site downstream of the staphylococcal crtM gene in pDCQ153. The resulting construct, pDCQ155, contained the ciM gene and the crtN-ald-crtN2 genes in the same orientation and under the control of the trc promoter from the pTrcHis2-TOPO vector (Invitrogen).

HPLC analysis of the *E. coli* pink transformants of pDCQ155 showed the presence of a carotenoid with the same absorption spectra (465 nm, 489–491 nm, 518–520 nm) as the 16a native carotenoid, suggesting that $C_{30}$ carboxy-carotenoid was produced in the recombinant *E. coli* strain. The retention time of the carotenoid from *E. coli* (11.4 min) was different from that of the 16a native carotenoid (12.7 min); however, this most likely resulted from the lack of ester formation in *E. coli*.

Transposon Mutagenesis of PDCQ155

The $C_{30}$ dialdehyde carotenoid ("diapocarotene dialdehyde") accumulated in *E. coli* following disruption of the aldehyde dehydrogenase (ald) gene by a transposon in pDCQ155. This was achieved as follows: in vitro transposon mutagenesis was performed on pDCQ155 DNA using EZ:: TN™ <TET-1>Insertion Kit (Epicentre, Madison, Wiss.). The transposon treated pDCQ155 DNA was transformed into *E. coil TOP*10 competent cells (Invitrogen). Cells containing transposon insertions were selected on LB plates with 10 μg/mL tetracycline. Transposon mutations were screened by PCR and further sequenced to confirm the insertion sites. Primers for screening included Tet-1 FP (SEQ ID NO:19) and crtN_R (SEQ ID NO:20). *E. coli* cells carrying various transposon insertions in pDCQ155 were cultured in 200 mL LB medium with 100 μg/mL Amp or 10 μg/mL Tet at 30° C. for 2 days. Cells were pelleted by centrifugation at 4000 g for 15 min. Carotenoids were extracted from the cell pellets with 10 mL methanol followed by 10 mL acetone, then dried under nitrogen and redissolved in 1 mL of methanol. Each sample of 100 μL was analyzed via HPLC as described in the General Methods.

Mutant p33, with a transposon insertion in the ald gene, produced the 4,4'-diapocarotene dialdehyde (round-shaped absorption at 507 nm) as well as the precursor, diapophytoene (maxima: 286 nm, 298 nm). $NaBH_4$ was added to the red-pigmented solution, causing a reduction to a yellow-pigmented solution whose pigment showed the absorption spectra of 442 nm, 468 nm, 498 nm. Reduction by $NaBH_4$ suggested that the red pigment produced in mutant p33 is an aldehyde carotenoid and not a carboxyl-carotenoid.

Example 4

Assembly of an Engineered Pathway to Increase $C_{30}$ Dialdehyde Synthesis in *E. coli*

Although the previous example demonstrated production of diapocarotene dialdehyde using the *Staphylococcus* crtM and the *Methylomonas* crtN-ald-crtN2 gene cluster, it was desirable to develop an engineered pathway to maximize production of the $C_{30}$ dialdehyde. Since two sets of genes could conceivably be used to synthesize $C_{30}$-aldehyde carotenoids in *E. coli* (derived from *Methylomonas* sp. 16a and/or *Staphylococcus aureus*), initial experimentation focused on determining which combinations of *Staphylococcus* and *Methylomonas* genes would permit maximal $C_{30}$-dialdehyde production in *E. coli*.

The conversion of FPP to diapophytoene could be achieved with the *Staphylococcus* CrtM (SEQ ID NO: 10). The *Methylomonas* sqs (SEQ ID NO:1) encodes a squalene synthase that converts FPP mainly to squalene, although a small amount of diapophytoene may also be produced based on the enzyme's partial diapophytoene synthase activity.

*Staphylococcus* CrtN (SEQ ID NO: 12) catalyzes desaturation of diapophytoene to form diaponeurosporene. *Methylomonas* CrtN (SEQ ID NO:4) catalyzes one additional desaturation step on diapophytoene to form diapocarotene. Thus, for synthesis of the $C_{30}$ monoaldehyde, the *Staphylococcus* CrtN is preferred. In contrast, synthesis of the $C_{30}$ dialdehyde requires the *Methylomonas* CrtN. Despite this rationale, since the crtN genes from *Staphylococcus* (SEQ ID NO:11) and *Methylomonas* (SEQ ID NO:3) shared only 57% identity at the nucleotide level, both crtN genes were included in the engineered pathway to increase desaturase activity for $C_{30}$ dialdehyde synthesis.

Finally, the conversion of diapocarotene to diapocarotene dialdehyde could be achieved with either the *Methylomonas* CrtN2 (SEQ ID NO:8) or the *Staphylococcus* CrtN2 (SEQ ID NO:14). In the preferred embodiment, the *Methylomonas* CrtN2 was used for the aldehyde group addition.

Thus, the *Staphylococcus* crtM gene (SEQ ID NO:9), *Staphylococcus* crtN gene (SEQ ID NO:11), *Methylomonas* crtN (SEQ ID NO:3) and *Methylomonas* crtN2 (SEQ ID NO:7) genes were chosen for the assembly of the engineered pathway, as shown in FIG. 6. Following determination of the "set" of genes which it would be desirable to express in *E. coli* for synthesis of the $C_{30}$ dialdehyde, the engineered pathway was then created, as described below.

Synthesis of Plasmid PDCQ166 (Comprising the *Staphylococcus* crtM-crtN gene cluster)

First, the crtM-crtN gene cluster from *Staphylococcus* was PCR amplified from genomic DNA of *Staphylococcus aureus* NCTC 8325 (ATCC 35556) using forward primer crtM_F/NCTC (5'-gaattcaggaggaataaaccatgacaatgatggatatgaattttaaa-3'; SEQ ID NO:21) and reverse primer crtN_R/NCTC (5'-gaattcttatacgccccgctcaatatctt-3'; SEQ ID NO:22). Underlined in the primers are the incorporated EcoRI sites and the bold text indicates an artificial ribosome binding site. The 2410 bp PCR product was first cloned in the pTrcHis2-TOPO (Invitrogen) cloning vector, resulting in pDCQ165.

The 2.4 kb EcoRI fragment from pDCQ165 containing the *Staphylococcus* crtM and crtN genes was ligated into the EcoRI site of vector pBHR1 (MoBiTec, Goettingen, Germany) to create pDCQ166, in which the crtM and crtN genes are expressed under the control of the chloramphenicol resistant gene promoter.

Synthesis of Plasmids pDCQ177 and pDCQ178 (Comprising *Methylomonas* crtN-crtN2 Gene Clusters)

crtN and crtN2 from *Methylomonas* were first individually cloned with and without an artificial ribosomal binding site (RBS) in pTrcHis2-TOPO (Invitrogen) resulting in pDCQ174, pDCQ167, pDCQ175 and pDCQ176, respectively. The 1542 bp crtN was amplified from 16a genomic DNA using primers crtN_5'/16a (SEQ ID NO:23) and crtN_3'/16a (5'-ggatcctcaggctttggcttttttcagc-3'; SEQ ID NO:24). The 1499 bp crtN2 was amplified using primers crtN2_F3/16a (SEQ ID NO:25) and crtN2_R/16a (5'-gaattctattgcaaatccgccacaatct-3'; SEQ ID NO:26). The 1574 bp crtN with RBS was amplified using primers crtN_5'_2/16a (5'-ggatccaagcttaaggaggaataaacc atggccaacaccaaacacatca-3'; SEQ ID NO:27) and crtN_3'_2/16a (5'-ggatccaagcttcaggctttggcttttttcagc-3'; SEQ ID NO:28). The 1531 bp crtN2 with RBS was amplified using primers crtN2_5'_2/16a (5'-ggatccaagcttaaggaggaataaaccatgaactcaaatgacaaccaacgc-3'; SEQ ID NO:29) and crtN2_3'_2/16a (5'-ggatccaagcttattgcaaatccgccacaatctt-3'; SEQ ID NO:30). Underlined in the primers are incorporated restriction sites and the bold text indicates an artificial ribosome binding site (RBS).

The *Methylomonas* crtN and crtN2 were then strung together by subcloning. Specifically, the approximately 1.5 kb HindIII fragment from pDCQ176 or pDCQ175, containing the crtN2 or crtN gene with an artificial ribosome binding site, was subcloned into the unique HindIII site in pDCQ174 and pDCQ167, resulting in plasmids pDCQ177 and pDCQ178, respectively. pDCQ177 carries the crtN-crtN2 construct, in which crtN was closer to the trc promoter on the vector; in contrast, pDCQ178 carries the crtN2-crtN construct, in which crtN2 was closer to the trc promoter.

*E. coli* MG1655 cells were co-transformed with pDCQ166 (containing *Staphylococcus* crtM-citN genes) and either pDCQ177 or pDCQ178 (each containing the *Methylomonas* crtN-crtN2 genes). This co-transformation completed the assembly of the engineered pathway.

Example 5

Analysis of Carotenoids Produced from *E. coli* Carrying the Engineered Pathway

*E. coli* cells containing pDCQ166+pDCQ177 and *E. coli* cells containing pDCQ166+pDCQ178 were grown in 100 mL LB (Luria Broth) or TB (Terrific Broth) medium with 50 µg/mL Kan and 100 µg/mL Amp at 37° C. for 1 day and harvested by centrifugation. As a control, *E. coli* MG1655 (pDCQ155::Tn5 p33) cells were grown under the same conditions (except with 100 µg/mL Amp). Carotenoids were extracted from the cell pellets with 3 volumes of 20 mL of methanol for 30 min at room temperature each time. The extracted pigments were dried under nitrogen and dissolved in 1 mL methanol. A volume of 0.1 mL of each sample was used for HPLC analysis, as described in the General Methods.

In each sample, the diapocarotene dialdehyde product eluted at 12.3 min with an absorption maximum of 506 nm. The *E. coli* MG1655 (pDCQ166/pDCQ177) trace indicated a minor intermediate was formed that eluted at 12.0 min with an absorption maximum of 469 nm. The *E. coli* MG1655 (pDCQ166/pDCQ178) trace indicated a minor intermediate was formed that eluted at 14.2 min with an absorption maximum of 413, 436, and 465 nm, corresponding to the diaponeurosporene absorption maxima.

The $C_{30}$-dialdehyde production was compared in each strain grown in LB and TB media by integration of the pigment peak from the HPLC traces. Subsequently, the normalized relative pigment yield per gram of cell paste was calculated for each culture (Table 8).

TABLE 8

Comparison of the $C_{30}$-dialdehyde pigment production in
E. coli Grown in Various Media

| E. coli MG1655 Strain | In LB Pigment/ g cell paste | In LB Cell paste (g) | In TB Pigment/ g cell paste | In TB Cell paste (g) |
|---|---|---|---|---|
| pDCQ155::Tn5 p33 | 1.0 | 0.55 | 2.4 | 2.42 |
| pDCQ166/pDCQ177 | 23.4 | 0.51 | 47.1 | 2.12 |
| pDCQ166/pDCQ178 | 15.0 | 0.44 | 24.8 | 2.01 |

As demonstrated in the Table 8 above, E. coli carrying the engineered pathway showed an approximately 20-fold increase in $C_{30}$-dialdehyde production, as compared to the transposon mutant p33 (E. coli MG1655 (pDCQ155::Tn5 p33)). Cells grown in TB showed an approximately 2-fold higher level of $C_{30}$-dialdehyde production per gram of cells, as compared to cells growing in LB. Since TB medium also produced an approximately 4-fold greater cell paste than LB medium, the total $C_{30}$-dialdehyde produced in cells grown in TB was approximately 8-fold greater than that from the same strain grown in LB. The E. coli MG1655 (pDCQ166/pDCQ177) strain was also observed to be more stable than E. coli MG1655 (pDCQ166/pDCQ178). Thus, the pDCQ166/pDCQ177 combination was chosen for further optimization in E. coli, for the production of the $C_{30}$-dialdehyde.

Example 6

Construction Of Optimized E. coli Host Strains WS100 and WS101

The native promoters of the E. coli isoprenoid genes dxs, idi, and ispAdxs (wherein ispAdxs is an operon comprising the ispA and dxs genes) were replaced with the phage T5 ($P_{T5}$) strong promoter using a two PCR-fragment chromosomal integration method (U.S. Ser. No. 10/734,936). This occurred in a multi-step process, as shown below:

1. First, using the two PCR fragment method, the kanamycin selectable marker and phage T5 promoter (kan-$P_{T5}$) were integrated upstream of the dxs, idi, and ispAdxs genes, yielding E. coli kan-$P_{T5}$-dxs, E. coli kan-$P_{T5}$-idi, and E. coli kan-$P_{T5}$-ispAdxs, respectively.
2. The optimized host strain WS101 (E. coli MG1655 $P_{T5}$-ispAdxs) was created by preparation of P1 lysate from E. coli kan-$P_{T5}$-ispAdxs and infection of E. coli MG1655. The kanamycin selectable marker was then removed from the transformed recipient host cells, using a FLP recombinase expression system.
3. The optimized host strain WS100 (E. coli MG1655 $P_{T5}$-dxs $P_{T5}$-idi) was created by transducing P1 lysate from E. coli kan-$P_{T5}$-dxs into E. coli MG1655, removing the kanamycin selectable marker, subsequently transducing P1 lysate from E. coli kan-$P_{T5}$-idi into the resultant bacteria, and removing the kanamycin selectable marker.

Triple Homologous Recombination Using the Two PCR Fragment Method to Create E. coli Kan-$P_{T5}$-dxs, E. coli Kan-$P_{T5}$-idi, and E. coli Kan-$P_{T5}$-ispAdxs The method of promoter replacement, described in FIG. 5, is based on homologous recombination via the λ-Red recombinase, which is encoded on a helper plasmid pKD46 (Datsenko and Wanner, supra). Recombination occurs between the E. coli chromosome and two PCR fragments that contain 20–50 bp homology patches at both ends of each PCR fragment. In the present example, the two PCR fragments included:

1.) a linear DNA fragment (1489 bp) containing a kanamycin selectable marker flanked by site-specific recombinase target sequences (FRT); and
2.) a linear DNA fragment (154 bp) containing $P_{T5}$, the −10 and −35 consensus promoter sequences, a lac operator (lacO), and a ribosomal binding site (RBS).

The 1489 bp linear DNA fragment containing a kanamycin selectable marker was synthesized by PCR from plasmid pKD4 (Datsenko and Wanner, supra) using the primer pairs shown below in Table 9.

TABLE 9

Primers for Amplification of the Kanamycin Selectable Marker

| Primer Name | Primer Sequence | SEQ ID NO: |
|---|---|---|
| 5'-kan(dxs) | <u>TGGAAGCGCTAGCGGACTACATCATCCAGCGTAATAA ATAA</u>CGTCTTGAGCGATTGTGTAG[1] | 31 |
| 5'-kan(idi) | <u>TCTGATGCGCAAGCTGAAGAAAAATGAGCATGGAGAA TAATATGA</u>CGTCTTGAGCGATTGTGTAG[1] | 32 |
| 5'- kan(ispAdxs) | <u>ACCATGACGGGGCGAAAAATATTGAGAGTCAGACATT CATGTGTAGGCTGGAGCTGCTTC</u>[1] | 33 |
| 3'-kan | GAAGACGAAAGGGCCTCGTGATACGCCTATTTTTATA GGTTATATGAATATCCTCC1TAGTTCC[2] | 34 |

[1]The underlined sequences illustrate each respective homology arm (chosen to match sequences in the upstream region of the chromosomal integration site), while the remainder is the priming sequence.
[2]The sequences shown in bold illustrate the homology arm chosen to match sequences in the 5'-end region of the T5 promoter DNA fragment.

The 154 bp linear DNA fragment containing $P_{T5}$ was synthesized by PCR from pQE30 (QIAGEN, Inc. Valencia, Calif.) with the primer pairs shown in Table 10.

Construction of Optimized Host Strain WS101 (*E. coli* MG1655 $P_{T5}$-ispA/dxs)

TABLE 10

Primers for Amplification of the T5 Promoter

| Primer Name | Primer Sequence | SEQ ID NO: |
|---|---|---|
| 5'-T5 | CTAAGGAGGATATTCATATAACCTATAAAAATAGGCGTATCACGAGGCCC[1] | 35 |
| 3'-T5(dxs) | GGAGTCGACCAGTGCCAGGGTCGGGTATTTGGCAATATCAAAACTCATAGTTAATTTCTCCTCTTTAATG[2] | 36 |
| 3'-T5(idi) | TGGGAACTCCCTGTGCATTCAATAAAATGACGTGTTCCGTTTGCATAGTTAATTTCTCCTCTTTAATG[2] | 37 |
| 3'-T5(ispAdxs) | CCTGCTTAACGCAGGCTTCGAGTTGCTGCGGAAAGTCCATAGTTAATTTCTCCTCTTTAATG[2] | 38 |

[1] The sequences in bold text illustrate the homology arm chosen to match sequences in the 3'-end region of the kanamycin DNA fragment.
[2] The underlined sequences illustrate each respective homology arm chosen to match sequences in the downstream region of the chromosomal integration site.

Standard PCR conditions were used to amplify the linear DNA fragments with AmpliTaq Gold polymerase (Applied Biosystems, Foster City, Calif.). Specifically, PCR reaction mixtures were prepared comprising: 0.5 µL plasmid DNA, 5 µL 10× PCR buffer, 1 µL dNTP mixture (10 mM), 1 µL 5'-primer (20 µM), 1 µL 3'-primer (20 µM), 0.5 µL AmpliTaq Gold polymerase, and 41 µL sterilized distilled $H_2O$. Amplification was carried out as follows: initial denaturation at 94° C. for 3 min, followed by 30 cycles of the following: 93° C. for 30 sec, 55° C. for 1 min, 72° C. for 3 min. A final extension cycle of 72° C. for 5 min was carried out.

After completing the PCR reactions, 50 µL of each PCR reaction mixture was run on a 1% agarose gel and the PCR products were purified using the QIAquick Gel Extraction Kit™, per the manufacturer's instructions (Cat. #28704, QIAGEN Inc., Valencia, Calif.). The PCR products were eluted with 10 µL of distilled water. The DNA Clean & Concentrator™ kit (Zymo Research, Orange, Calif.) was used to further purify the PCR product fragments. Subsequently, the PCR products were eluted with 6–8 µL of distilled water to a concentration of 0.5–1.0 mg/mL.

The host strain utilized for chromosomal integration of the PCR fragments described above was constructed by transforming *E. coli* strain MC1061 with the λ-Red recombinase expression plasmid, pKD46 (amp$^R$) (Datsenko and Wanner, supra; SEQ ID NO:39). Transformants were selected on 100 µg/mL of Amp LB plates at 30° C.

For triple homologous recombination, electroporation into the ampicillin resistant *E. coli* strain MC1061 transformants was performed using 5–10 µg of the purified PCR products carrying the kanamycin marker and $P_{T5}$. Approximately one-half of the cells transformed were spread on LB plates containing 25 µg/mL Kan. After incubating the plates at 37° C. overnight, antibiotic-resistance transformants were selected as follows: 10 colonies of *E. coli* kan-$P_{T5}$-dxs, 12 colonies of *E. coli* kan-$P_{T5}$-idi, and 19 colonies of *E. coli* kan-$P_{T5}$-ispAdxs.

P1 lysate of the *E. coli* kan-$P_{T5}$-ispAdxs strain was prepared as follows: The *E. coli* kan-$P_{T5}$-ispAdxs strain was inoculated in 4 mL LB medium with 25 µg/mL Kan, grown at 37° C. overnight, and then sub-cultured with 1:100 dilution of an overnight culture in 10 mL LB medium containing 5 mM $CaCl_2$. After 20–30 min of growth at 37° C., $10^7$ P1$_{vir}$ phages were added. The cell-phage mixture was aerated for 2–3 h at 37° C. until lysed, several drops of chloroform were added and the mixture was vortexed for 30 sec and incubated for an additional 30 min at room temperature. The mixture was then centrifuged for 10 min at 4500 rpm, and the supernatant transferred into a new tube to which several drops of chloroform were added.

The P1 lysate produced from *E. coli* kan-$P_{T5}$-ispAdxs was transduced into the recipient strain, *E. coli* MG1655. Specifically, the *E. coli* MG1655 recipient cells were grown to mid-log phase ($1-2\times10^8$ cells/mL) in 4 mL LB medium at 37° C. Cells were spun down for 10 min at 4500 rpm and resuspended in 2 mL of 10 mM $MgSO_4$ and 5 mM $CaCl_2$. Recipient cells (100 mL) were mixed with 1 mL, 10 mL, or 100 mL of P1 lysate stock ($10^7$ pfu/mL) made from the *E. coli* kan-$P_{T5}$-ispAdxs strain and incubated at 30° C. for 30 min. The recipient cell-lysate mixture was spun down at 6500 rpm for 30 sec, resuspended in 100 mL of LB medium with 10 mM of sodium citrate, and incubated at 37° C. for 1 h. Cells were plated on LB plates containing 25 µg/mL Kan in order to select for kanamycin-resistant transductants, and incubated at 37° C. for 1–2 days. Kanamycin-resistance transductants were selected.

The kanamycin selectable marker was eliminated from the chromosome of kanamycin-resistance transductants using a FLP recombinase expression plasmid pCP20 (amp$^R$) (ATCC PTA-4455) (Cherepanov and Wackernagel, *Gene* 158:9–14 (1995)). This plasmid, which has a temperature-sensitive replication of origin, was transiently transformed into one of the kanamycin-resistant transductants by electroporation. Cells were spread onto LB agar containing 100 µg/mL Amp, and grown at 30° C. for 1 day. Colonies were picked and streaked on LB plates without Amp and incubated at 43° C. overnight (to enable curing of pCP20 from the host cells). The colonies were tested for Amp and Kan sensitivity (to test for loss of pCP20 and the Kan selectable marker) by streaking colonies onto 100 μg/mL Amp LB plates or 25 μg/mL Kan LB plates. In this manner, the WS101 (*E. coli* MG1655 $P_{T5}$-ispAdxs) strain was constructed.

Construction of Optimized Host Strain WS100 (MG1655 $P_{T5}$-dxs $P_{T5}$ idi)

P1 lysate made with the *E. coli* kan-$P_{T5}$-dxs strain was transduced into the recipient strain, *E. coli* MG1655 as described above. Sixteen kanamycin-resistance transductants were selected. The kanamycin selectable marker was eliminated from the chromosome of the transductants, using a FLP recombinase expression system as described above (i.e., pCP20), yielding *E. coli* $P_{T5}$-dxs.

In order to stack kan-$P_{T5}$-idi on the chromosome of *E. coli* $P_{T5}$-dxs, P1 lysate made from *E. coli* kan-$P_{T5}$-idi was transduced into the recipient strain, *E. coli* $P_{T5}$-dxs, as described above. Approximately 450 kanamycin-resistance transductants were selected. After transduction, the kanamycin selectable marker was eliminated from the chromosome as described above, yielding *E. coli* $P_{T5}$-dxs $P_{T5}$-idi. Correct integration of the phage T5 promoter upstream of the dxs and idi genes on the *E. coli* chromosome, and elimination of the kanamycin selectable marker, were confirmed by PCR analysis. In this manner, the WS100 (*E. coli* MG1655 $P_{T5}$-dxs $P_{T5}$-idi) strain was constructed.

Example 7

Expression of the Engineered Pathway for $C_{30}$ Dialdehyde Synthesis in Engineered *E. coli* Host Strains Plasmids pDCQ166 and pDCQ177 (from Example 4) were co-transformed into WS100 and WS101 and transformants were selected on plates with Amp (100 μg/mL) and Kan (50 μg/mL). By visualization, WS100 transformants appeared darker-pigmented than wild type MG1655 containing the two plasmids, whereas WS101 transformants appeared lighter-pigmented. WS100 (pDCQ166/pDCQ177) and MG1655 (pDCQ166/pDCQ177) were grown in 100 mL LB with Amp and Kan overnight. Pigments from the two strains were extracted and analyzed as described previously. $C_{30}$-dialdehyde synthesis in the WS100 host was approximately 50% greater than that of the MG1655 host. On this basis, the strain WS100 (pDCQ166/pDCQ177) was thus chosen for production of the $C_{30}$-dialdehyde via fermentation.

Example 8

Fermentation Production of $C_{30}$-Dialdehyde in Engineered *E. coli* Host Strain WS100 (MG1655 $P_{T5}$-dxs $P_{T5}$-idi)

Aldehydes are known to be toxic to biological cells; thus, a fermentation strategy was designed to decrease toxicity by delaying the production of the $C_{30}$-dialdehyde until after cell mass reached a high level. Specifically, cells were initially grown with glucose feed as the carbon source to suppress carotenoid production; after accumulation of cell mass, the carbon source was switched to fructose to allow $C_{30}$-production of the aldehyde.

A seed culture of WS100 (pDCQ166/pDCQ177) was started from a 1 mL frozen glycerol stock prepared from cells grown from a single colony. The seed culture was grown in 500 mL of 2XYT medium (10 g/L yeast extract, 16 g/L tryptone, and 10 g/L NaCl) in a 2-L Erlenmeyer flask, containing 10% glucose, 100 μg/mL Amp and 50 μg/mL Kan at 35° C. in a shaker at 300 rpm for 8 h. This initial culture with an optical density of 1.9 at 600 nm was used to inoculate a Braun Biostat C stirred tank fermentor with a 10-L working volume (B. Braun Biotech International GmbH, Melsungen, Germany).

The following components were sterilized together in the fermentor vessel: 10 mL/L Modified Balch's Trace element solution (which contained 4 g/L citric acid.$H_2O$, 3 g/L $MnSO_4.H_2O$, 1 g/L NaCl, 0.1 g/L $FeSO_4.7H_2O$, 0.1 g/L $ZnSO_4.7H_2O$, 0.001 g/L $CuSO_4.5H_2O$, 0.001 g/L $H_3BO_3$, 0.001 g/L $NaMoO_4.2H_2O$), 5 g/L yeast extract, 0.2 g/L $CaCl_2.2H_2O$, 0.3 g/L ferric ammonium citrate, 2 g/L $MgSO_4.7H_2O$, 2 g/L citric acid, 7.5 g/L $KH_2PO_4$, 1.2 g/L sulfuric acid, and 0.8 mUL Mazu DF204 as an antifoaming agent. After sterilization, the pH was raised to 6.8 with 40% $NH_4OH$. The concentration of Amp was brought to 100 g/L and the concentration of Kan was brought to 50 mg/mL. A 65% glucose solution (246 g) was added post vessel sterilization to give a 20 g/L initial concentration in the fermentor.

The fermentation was started with an 8-L volume of medium as described above containing 20 g/L glucose. After 13 h, when the absorption at 600 nm of the culture was above 20, a 10% fructose bolus was added at a rate of 20 mL/min until 2 L was added. Glucose concentration was below 0.1 g/L at 17 h of fermentation. The temperature was controlled at 35° C. and the pH was maintained at 7.6 with 40% $NH_4OH$ and 20% $H_3PO_4$. Back pressure was manually controlled at 0.5 bar (7.5 psig or about 51.7 kPa). The dissolved oxygen set point was 10%. After 27 hours of fermentation, 9 L of cell culture was harvested. The cell paste was extracted and approximately 20 mg of $C_{30}$-dialdehyde was produced from the 10-L fermentation.

Example 9

Confirmation of the $C_{30}$-dialdehyde Produced by Fermentation in Engineered *E. coli* Host Strain WS100 (MG1655 $P_{T5}$-dxs $P_{T5}$-idi)

The carotenoid pigment extracted from the harvested cells (from Example 8) was subjected to HPLC analysis, $NaBH_4$ reduction and mass spectrometry analysis. HPLC analysis was performed as described in the General Methods and indicated that the absorption spectrum was 504 nm 536 nm, which is consistent with that reported for $C_{30}$-dialdehyde. The red pigment produced in the fermentation was reduced by $NaBH_4$ to a yellow pigment that had an absorption spectrum of 444 nm, 470 nm, 501 nm. This reduction experiment suggested that the carotenoid had aldehyde functional group(s).

The molecular weight of this carotenoid was also determined by LC-MS. Each sample of 50 μL was run on a Zorbax 2.1×150 mm SB-C18 LC column (Agilent Technologies, CA) with solvent program of:

0–30 min: linear gradient from 70% acetonitrile and 30% water to 100% acetonitrile;

30–45 min: 100% acetonitrile.

The mass spectrometer (Micromass Quattro LC triple quadrapole, Micromass Limited, UK) was scanned from 100 to 1000 AMU's in 0.9 sec with an 0.1 sec interscan delay in APCI (Atmospheric Pressure Chemical Ionization) mode with the corona discharge needle at 3KV and the APCI probe at 450° C. LC-MS analyses determined the molecular weight of the carotenoid to be 428, which agreed with that of diapocarotene-dialdehyde. Finally, an authentic standard of 4,4'-diapocarotene dialdehyde was synthesized by CaroteNature (Lupsingen, Switzerland). The LC retention time, absorption spectra and the molecular weight of the carotenoid produced by our fermentation all matched well with those of the synthetic standard. Based on these analyses, it was concluded that diapocarotene-dialdehyde was produced by the fermentation.

What is claimed is:

1. A method for the production of $C_{30}$-aldehyde carotenoid compounds comprising:
   (a) providing a transformed host cell comprising:
      (i) suitable levels of farnesyl pyrophosphate;
      (ii) at least one isolated nucleic acid molecule encoding an enzyme having diapophytoene synthase activity under the control of suitable regulatory sequences wherein the isolated nucleic acid molecule is selected from the group consisting of
         1) an isolated nucleic acid molecule encoding the amino acid sequence as set forth in SEQ ID NO:2;
         2) an isolated nucleic acid molecule encoding the amino acid sequence as set forth in SEQ ID NO:10; and
         3) an isolated nucleic acid molecule that hybridizes with (1) or (2) under the following hybridization conditions:0.1× SSC, 0.1% SDS, 65° C. and washed with 2×SSC, 0.1% SDS followed by 0.1× SSC, 0.1% SDS;
      (iii) at least one isolated nucleic acid molecule encoding an enzyme having diapophytoene desaturase activity under the control of suitable regulatory sequences wherein the isolated nucleic acid molecule is selected from the group consisting of;
         1) an isolated nucleic acid molecule encoding the amino acid sequence as set forth in SEQ ID NO:4;
         2) an isolated nucleic acid molecule encoding the amino acid sequence as set forth in SEQ ID NO:12; and
         3) an isolated nucleic acid molecule that hybridizes with (1) or (2) under the following hybridization conditions: 0.1×SSC, 0.1% SDS, 65° C. and washed with 2×SSC, 0.1% SDS followed by 0.1× SSC, 0.1% SDS; and
      (iv) at least one isolated nucleic acid molecule encoding an enzyme having the ability to introduce an omega-aldehyde functional group on the omega carbon of a conjugated polyene carbon skeleton under the control of suitable regulatory sequences; wherein the isolated nucleic acid molecule is selected from the group consisting of;
         1) an isolated nucleic acid molecule encoding the amino acid sequence as set forth in SEQ ID NO:8;
         2) an isolated nucleic acid molecule encoding the amino acid sequence as set forth in SEQ ID NO:14; and
         3) an isolated nucleic acid molecule that hybridizes with (1) or (2) under the following hybridization conditions: 0.1×SSC, 0.1% SDS, 65° C. and washed with 2×SSC, 0.1% SDS followed by 0.1× SSC, 0.1% SDS; and
   (b) contacting the host cell of step (a) under suitable growth conditions with an effective amount of fermentable carbon substrate whereby a $C_{30}$-aldehyde carotenoid compound is produced.

2. A method according to claim 1 wherein the $C_{30}$-aldehyde carotenoid compound is selected form the group consisting of: diaponeurosporene monoaldehyde, diapocarotene monoaldehyde, diapocarotene dialdehyde and functional derivatives thereof.

3. A method according to claim 1 wherein the suitable levels of farnesyl pyrophosphate are provided by the over-expression of heterologous upper pathway isoprenoid pathway genes.

4. A method according to claim 3 wherein said upper pathway isoprenoid genes are selected from the group consisting of D-1-deoxyxylulose-5-phosphate synthase (dxs), D-1-deoxyxylulose-5-phosphate reductoisomerase (dxr), 2C-methyl-D-erythritol cytidylyltransferase (ispD), 4-diphosphocytidyl-2-C-methylerythritol kinase (ispE), 2C-methyl-d-erythritol 2,4-cyclodiphosphate synthase (ispF), CTP synthase (pyrG), lytB, gcpE, idi, and farnesyl diphosphate synthase (ispA).

5. A method according to claim 4 wherein said over-expressed upper pathway isoprenoid genes are dxs and idi and wherein said over-expression is the result of up-regulating the promoter activity upstream of each gene.

6. A method according to claim 1 wherein the host cell is selected from the group consisting of bacteria, yeast, filamentous fungi, algae, and green plants.

7. The method according to claim 6, wherein the transformed host cell is selected from the group consisting of *Aspergillus, Trichoderma, Saccharomyces, Phaffia, Pichia, Candida, Rhodotorula, Rhodosporidium, Hansenula, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Methylobacterium, Alcaligenes, Synechocystis, Synechococcus, Anabaena, Thiobacillus, Methanobacterium, Klebsiella, Myxococcus*, and *Staphylococcus*.

8. The method according to claim 7, wherein the transformed host cell is *Escherichia coli*.

9. The method according to claim 6, wherein the transformed host cell is selected from the group consisting of soybean, rapeseed pepper, sunflower cotton corn, tobacco alfalfa wheat barley oats sorghum rice *Arabidopsis*, cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees, marigold, and forage grasses.

10. The method according to claim 6, wherein the transformed host cell is selected from the group consisting of *Spirulina, Haemotacoccus*, and *Dunalliela*.

* * * * *